(12) United States Patent
Giliyar et al.

(10) Patent No.: US 11,304,960 B2
(45) Date of Patent: *Apr. 19, 2022

(54) STEROIDAL COMPOSITIONS

(76) Inventors: Chandrashekar Giliyar, Salt Lake City, UT (US); Nachiappan Chidambaram, Sandy, UT (US); Mahesh V. Patel, Salt Lake City, UT (US); Srinivasan Venkateshwaran, Salt Lake City, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 12/350,930

(22) Filed: Jan. 8, 2009

(65) Prior Publication Data

US 2010/0173882 A1    Jul. 8, 2010

(51) Int. Cl.

| | | |
|---|---|---|
| A61K 31/569 | (2006.01) | |
| A61K 9/48 | (2006.01) | |
| A61K 31/568 | (2006.01) | |
| A61K 9/00 | (2006.01) | |
| A61K 47/10 | (2017.01) | |
| A61K 47/14 | (2017.01) | |
| A61K 47/44 | (2017.01) | |

(52) U.S. Cl.
CPC .......... *A61K 31/569* (2013.01); *A61K 9/0053* (2013.01); *A61K 9/4858* (2013.01); *A61K 9/4866* (2013.01); *A61K 9/4875* (2013.01); *A61K 31/568* (2013.01); *A61K 47/10* (2013.01); *A61K 47/14* (2013.01); *A61K 47/44* (2013.01)

(58) Field of Classification Search
CPC ............................ A61K 31/569; A61K 9/0053
USPC ....................................................... 514/178
See application file for complete search history.

(56) References Cited

U.S. PATENT DOCUMENTS

| | | | |
|---|---|---|---|
| 2,680,749 A | 5/1954 | Cawley et al. | |
| 2,742,487 A | 4/1956 | Robledano | |
| 3,097,139 A | 7/1963 | Sonne | |
| 3,097,144 A | 7/1963 | Banker | |
| 3,164,520 A | 1/1965 | Huber | |
| 3,266,991 A | 8/1966 | Wettstein et al. | |
| 3,510,561 A | 5/1970 | Koh | |
| 4,098,802 A | 7/1978 | van der Vies | |
| 4,147,783 A * | 4/1979 | van der Vies | ....... A61K 9/0056 514/171 |
| 4,156,719 A | 5/1979 | Sezaki et al. | |
| 4,177,188 A | 12/1979 | Hansen et al. | |
| 4,196,188 A | 4/1980 | Besins | |
| 4,220,599 A | 9/1980 | van der Vies | |
| 4,239,754 A | 12/1980 | Sache et al. | |
| 4,388,307 A | 6/1983 | Cavanak | |
| 4,439,432 A | 3/1984 | Peat | |
| 4,572,915 A | 2/1986 | Crooks | |
| 4,579,730 A | 4/1986 | Kidron et al. | |
| 4,628,052 A | 12/1986 | Peat | |
| 4,628,098 A | 12/1986 | Nohara et al. | |
| 4,654,327 A | 3/1987 | Teng | |
| 4,656,161 A | 4/1987 | Herr | |
| 4,689,333 A | 8/1987 | Nohara et al. | |
| 4,695,450 A | 9/1987 | Bauer | |
| 4,703,042 A | 10/1987 | Bodor | |
| 4,713,246 A | 12/1987 | Begum et al. | |
| 4,717,569 A | 1/1988 | Harrison et al. | |
| 4,717,596 A | 1/1988 | Barbee et al. | |
| 4,719,239 A | 1/1988 | Muller et al. | |
| 4,727,109 A | 2/1988 | Schmidt et al. | |
| 4,731,384 A | 3/1988 | Dell | |
| 4,795,327 A | 1/1989 | Gaylord et al. | |
| 4,832,952 A | 5/1989 | Hersh et al. | |
| 4,834,965 A | 5/1989 | Martani et al. | |
| 4,849,227 A | 7/1989 | Cho | |
| 4,867,984 A | 9/1989 | Patel | |
| 4,874,795 A * | 10/1989 | Yesair | .................... A61K 47/12 514/725 |
| 4,880,634 A | 11/1989 | Speiser | |
| 4,895,726 A | 1/1990 | Curtet et al. | |
| 4,897,269 A | 1/1990 | Mezei | |
| 4,900,734 A | 2/1990 | Maxson et al. | |
| 4,925,672 A | 5/1990 | Gremm | |
| 4,944,949 A | 7/1990 | Story | |
| 4,961,890 A | 10/1990 | Boyer | |
| 4,963,540 A | 10/1990 | Maxson et al. | |
| 4,994,439 A | 2/1991 | Longenecker et al. | |
| 5,014,656 A | 5/1991 | Leptich et al. | |

(Continued)

FOREIGN PATENT DOCUMENTS

| | | |
|---|---|---|
| CN | 101217963 | 7/2008 |
| DE | 10108614 A1 | 9/2002 |

(Continued)

OTHER PUBLICATIONS

Beatch, G.N. et al., "Ventricular Fibrillation, an Uncontrolled Arrhythmia Seeking New Targets," Drug Dev. Res. 55:45-52 (2002).

Goncharova et al., "Preparation of Testosterone Esters," Pharmaceutical Chemistry Journal 7(7):427-428 (1973).

Houwing, N.S. et al., "Pharmacokinetic Study in Women of Three Different Doses of a New Formulation of Oral Testosterone Undecanoate, Andriol Testocaps," Pharmacotherapy 23( 10): 1257-1265 (2003).

(Continued)

*Primary Examiner* — Marcos L Sznaidman

(74) *Attorney, Agent, or Firm* — Michael R. Schramm; David W. Osborne; Thorpe North and Western, LLP

(57) ABSTRACT

Provided herein are steroid containing compositions suitable for providing therapeutically effective amounts of at least one steroid to individuals. Also provided herein are compositions comprising testosterone and/or testosterone derivatives suitable for providing therapeutically effective and safe amounts of testosterone over periods of time. Further provided are methods of treating andro- and/or testosterone deficiency in individuals by administering to the individuals compositions described herein.

2 Claims, 3 Drawing Sheets

(56) References Cited

U.S. PATENT DOCUMENTS

| | | |
|---|---|---|
| 5,023,108 A | 6/1991 | Bagaria et al. |
| 5,026,560 A | 6/1991 | Makino et al. |
| 5,035,891 A | 7/1991 | Runkel et al. |
| 5,045,321 A | 9/1991 | Makino et al. |
| 5,071,643 A | 12/1991 | Yu et al. |
| 5,091,187 A | 2/1992 | Haynes |
| 5,091,188 A | 2/1992 | Haynes |
| 5,093,132 A | 3/1992 | Makino et al. |
| 5,120,710 A | 6/1992 | Liedtke |
| 5,140,021 A | 8/1992 | Maxson et al. |
| 5,145,684 A | 9/1992 | Liversidge |
| 5,152,997 A | 10/1992 | Ebert et al. |
| 5,206,219 A | 4/1993 | Desai |
| 5,244,925 A | 9/1993 | Wretlind |
| 5,252,339 A | 10/1993 | Cristofori et al. |
| 5,270,005 A | 12/1993 | Raible |
| 5,270,055 A | 12/1993 | Moest |
| 5,300,529 A | 4/1994 | Narayanan |
| 5,340,589 A | 8/1994 | Stetsko et al. |
| 5,342,625 A | 8/1994 | Hauer et al. |
| 5,350,741 A | 9/1994 | Takada |
| 5,364,632 A | 11/1994 | Benita et al. |
| 5,374,446 A | 12/1994 | Ferenz et al. |
| 5,376,688 A | 12/1994 | Morton et al. |
| 5,380,535 A | 1/1995 | Geyer et al. |
| 5,384,133 A | 1/1995 | Boyes et al. |
| 5,389,382 A | 2/1995 | List |
| 5,403,593 A | 4/1995 | Royce |
| 5,433,959 A | 7/1995 | Makino et al. |
| 5,444,041 A | 8/1995 | Owen |
| 5,500,224 A | 3/1996 | Vranckx et al. |
| 5,532,002 A | 7/1996 | Story |
| 5,539,000 A | 7/1996 | Leonard |
| 5,543,393 A | 8/1996 | Kim et al. |
| 5,545,628 A | 8/1996 | DeBoeck et al. |
| 5,560,931 A | 10/1996 | Eickhoff et al. |
| 5,571,533 A | 11/1996 | Santus et al. |
| 5,571,536 A | 11/1996 | Eickhoff et al. |
| 5,573,783 A | 11/1996 | Desieno et al. |
| 5,589,455 A | 12/1996 | Woo |
| 5,589,513 A | 12/1996 | Magyar et al. |
| 5,593,971 A | 1/1997 | Tschollar et al. |
| 5,614,491 A | 3/1997 | Walch et al. |
| 5,616,330 A | 4/1997 | Kaufman et al. |
| 5,622,721 A | 4/1997 | Dansereau et al. |
| 5,624,687 A | 4/1997 | Yano et al. |
| 5,626,869 A | 5/1997 | Nyqvist et al. |
| 5,629,021 A | 5/1997 | Wrigh |
| 5,633,015 A | 5/1997 | Gilis |
| 5,633,226 A | 5/1997 | Owen |
| 5,635,520 A | 6/1997 | Uda |
| 5,639,474 A | 6/1997 | Woo |
| 5,639,478 A | 6/1997 | Makino et al. |
| 5,639,724 A | 6/1997 | Cavanak |
| 5,645,856 A | 7/1997 | Lacy et al. |
| 5,646,109 A | 7/1997 | Owen |
| 5,653,987 A | 8/1997 | Modi et al. |
| 5,656,277 A | 8/1997 | Berlati et al. |
| 5,656,289 A | 8/1997 | Cho et al. |
| 5,665,379 A | 9/1997 | Herslof et al. |
| 5,681,584 A | 10/1997 | Savastano et al. |
| 5,686,105 A | 11/1997 | Kelm et al. |
| 5,688,761 A | 11/1997 | Owen et al. |
| 5,698,155 A | 12/1997 | Grosswald et al. |
| 5,707,648 A | 1/1998 | Yiv |
| 5,714,477 A | 2/1998 | Einarsson |
| 5,717,477 A | 2/1998 | Einarsson |
| 5,726,181 A | 3/1998 | Hausheer et al. |
| 5,731,355 A | 3/1998 | Jones et al. |
| 5,736,161 A | 4/1998 | Garces et al. |
| 5,741,512 A | 4/1998 | Hauer et al. |
| 5,741,822 A | 4/1998 | Yesair |
| 5,747,066 A | 5/1998 | Pittrof et al. |
| 5,756,450 A | 5/1998 | Hahn et al. |
| 5,759,997 A | 6/1998 | Cavanak |
| 5,766,629 A | 6/1998 | Cho et al. |
| 5,767,069 A | 6/1998 | Ko et al. |
| 5,795,883 A | 8/1998 | Hesch et al. |
| 5,798,333 A | 8/1998 | Sherman |
| 5,811,120 A | 9/1998 | Gibson et al. |
| 5,817,320 A | 10/1998 | Stone |
| 5,827,536 A | 10/1998 | Laruelle |
| 5,846,971 A | 12/1998 | Sangekar et al. |
| 5,853,748 A | 12/1998 | New |
| 5,855,905 A | 1/1999 | Oettel et al. |
| 5,858,398 A | 1/1999 | Cho |
| 5,858,401 A | 1/1999 | Bhalani et al. |
| 5,866,159 A | 2/1999 | Hauer et al. |
| 5,874,418 A | 2/1999 | Stella et al. |
| 5,880,148 A | 3/1999 | Edgar et al. |
| 5,883,109 A | 3/1999 | Gregg et al. |
| 5,891,469 A | 4/1999 | Amselem |
| 5,891,845 A | 4/1999 | Myers |
| 5,916,589 A | 6/1999 | Hauer et al. |
| 5,922,355 A | 7/1999 | Parikh et al. |
| 5,948,825 A | 9/1999 | Takahashi et al. |
| 5,962,014 A | 10/1999 | Hauer et al. |
| 5,962,017 A | 10/1999 | Hauer et al. |
| 5,976,574 A | 11/1999 | Gordon |
| 5,981,479 A | 11/1999 | Ko et al. |
| 5,981,586 A | 11/1999 | Pershadsingh |
| 5,989,583 A | 11/1999 | Amselem |
| 5,993,880 A | 11/1999 | Frost et al. |
| 6,007,840 A | 12/1999 | Hauer et al. |
| 6,008,192 A | 12/1999 | Al-Razzak et al. |
| 6,013,665 A | 1/2000 | DeMichele et al. |
| 6,017,560 A | 1/2000 | Makino et al. |
| 6,022,852 A | 2/2000 | Klokkers et al. |
| 6,024,978 A | 2/2000 | Hauer et al. |
| 6,027,747 A | 2/2000 | Terracol et al. |
| 6,042,847 A | 3/2000 | Kerc et al. |
| 6,046,177 A | 4/2000 | Stella et al. |
| 6,057,339 A | 5/2000 | Gregg |
| 6,066,653 A | 5/2000 | Gregg et al. |
| 6,074,670 A | 6/2000 | Stamm et al. |
| 6,086,376 A | 7/2000 | Moussa et al. |
| 6,096,338 A | 8/2000 | Lacy et al. |
| 6,123,962 A | 9/2000 | Makino et al. |
| 6,160,007 A | 12/2000 | DeMichele et al. |
| 6,174,547 B1 | 1/2001 | Dong et al. |
| 6,180,138 B1 | 1/2001 | Engh et al. |
| 6,189,486 B1 | 2/2001 | Lindholm |
| 6,193,985 B1 | 2/2001 | Sonne |
| 6,221,395 B1 | 4/2001 | Maggi et al. |
| 6,224,840 B1 | 5/2001 | Kim et al. |
| 6,228,399 B1 | 5/2001 | Parikh et al. |
| 6,228,400 B1 | 5/2001 | Lee et al. |
| 6,248,363 B1 | 6/2001 | Patel et al. |
| 6,255,100 B1 | 7/2001 | Ko et al. |
| 6,267,985 B1 | 7/2001 | Chen et al. |
| 6,294,192 B1 | 9/2001 | Patel et al. |
| 6,296,876 B1 | 10/2001 | Odidi et al. |
| 6,303,662 B1 | 10/2001 | Nagahama et al. |
| 6,306,825 B1 | 10/2001 | Cavanak |
| 6,309,663 B1 | 10/2001 | Patel et al. |
| 6,328,993 B1 | 12/2001 | Linder et al. |
| 6,328,994 B1 | 12/2001 | Shimizu et al. |
| 6,340,471 B1 | 1/2002 | Kershman et al. |
| 6,342,246 B2 | 1/2002 | Johnson et al. |
| 6,361,796 B1 | 3/2002 | Rudnic et al. |
| 6,368,634 B1 | 4/2002 | Remon |
| 6,379,705 B1 | 4/2002 | Mendes et al. |
| 6,383,471 B1 | 5/2002 | Chen et al. |
| 6,383,510 B1 | 5/2002 | Linder et al. |
| 6,383,517 B1 | 5/2002 | Qiu et al. |
| 6,391,342 B1 | 5/2002 | Henriksen et al. |
| 6,432,445 B1 | 8/2002 | Ambuhl et al. |
| 6,444,225 B1 | 9/2002 | Sherman |
| 6,447,806 B1 | 9/2002 | Gassmann et al. |
| 6,451,339 B2 | 9/2002 | Patel et al. |
| 6,455,518 B2 | 9/2002 | Zenke et al. |
| 6,458,373 B1 | 10/2002 | Lambert et al. |
| 6,458,383 B2 | 10/2002 | Chen et al. |
| 6,465,016 B2 | 10/2002 | Parikh et al. |

(56) References Cited

U.S. PATENT DOCUMENTS

| | | | |
|---|---|---|---|
| 6,468,559 B1 | 10/2002 | Chen et al. | |
| 6,475,519 B1 | 11/2002 | Armin et al. | |
| 6,503,894 B1 | 1/2003 | Dudley et al. | |
| 6,531,139 B1 | 3/2003 | Gao et al. | |
| 6,569,463 B2 | 5/2003 | Patel et al. | |
| 6,589,552 B2 | 7/2003 | Stamm et al. | |
| 6,589,562 B1 | 7/2003 | Shefer et al. | |
| 6,623,755 B2 | 9/2003 | Chen et al. | |
| 6,630,134 B1 | 10/2003 | Klein | |
| 6,652,880 B1 | 11/2003 | Aylwin et al. | |
| 6,665,880 B2 | 12/2003 | Poppe | |
| 6,667,048 B1 | 12/2003 | Lambert et al. | |
| 6,692,766 B1 | 2/2004 | Rubinstein et al. | |
| 6,720,001 B2 | 5/2004 | Chen et al. | |
| 6,761,903 B2 | 7/2004 | Chen et al. | |
| 6,881,745 B2 | 4/2005 | Hayes et al. | |
| 6,887,493 B2 | 5/2005 | Shefer et al. | |
| 6,913,244 B1 | 7/2005 | Atkinson et al. | |
| 6,923,988 B2 | 8/2005 | Patel et al. | |
| 6,977,083 B1 | 12/2005 | Huebler et al. | |
| 6,982,281 B1 | 1/2006 | Chen et al. | |
| 7,025,979 B2 | 4/2006 | Neischlag et al. | |
| 7,374,779 B2 | 5/2008 | Chen et al. | |
| 7,658,944 B2 | 2/2010 | Holm et al. | |
| 8,241,664 B2 * | 8/2012 | Dudley | A61K 9/06 424/456 |
| 8,778,922 B2 | 7/2014 | Chandrashekar et al. | |
| 8,865,695 B2 | 10/2014 | Chandrashekar et al. | |
| 2001/0018069 A1 | 8/2001 | Johnson et al. | |
| 2002/0006443 A1 | 1/2002 | Curatolo et al. | |
| 2002/0013304 A1 | 1/2002 | Wilson et al. | |
| 2002/0058066 A1 | 5/2002 | Tomohira et al. | |
| 2002/0068693 A1 | 6/2002 | Jeng et al. | |
| 2002/0102301 A1 | 8/2002 | Schwartz | |
| 2002/0103139 A1 | 8/2002 | Weisspapir et al. | |
| 2002/0183296 A1 | 12/2002 | Dudley et al. | |
| 2003/0022875 A1 | 1/2003 | Wilson et al. | |
| 2003/0072798 A1 | 4/2003 | Schwarz et al. | |
| 2003/0077297 A1 | 4/2003 | Chen et al. | |
| 2003/0082215 A1 | 5/2003 | Lemut et al. | |
| 2003/0104048 A1 | 6/2003 | Patel et al. | |
| 2003/0175329 A1 | 9/2003 | Azarnoff | |
| 2003/0180352 A1 | 9/2003 | Patel et al. | |
| 2003/0181431 A1 | 9/2003 | Hodgen | |
| 2003/0186892 A1 | 10/2003 | Taneja | |
| 2003/0228358 A1 | 12/2003 | Perlman et al. | |
| 2003/0235595 A1 | 12/2003 | Chen et al. | |
| 2003/0236236 A1 | 12/2003 | Chen et al. | |
| 2004/0002445 A1 | 1/2004 | Taneja | |
| 2004/0048896 A1 | 3/2004 | Phillips | |
| 2004/0120994 A1 | 6/2004 | Theobald | |
| 2004/0127476 A1 | 7/2004 | Kershman et al. | |
| 2005/0031693 A1 | 2/2005 | Babcock et al. | |
| 2005/0070516 A1 | 3/2005 | Wilson | |
| 2005/0080075 A1 | 4/2005 | Nichols et al. | |
| 2005/0096296 A1 | 5/2005 | Fikstad et al. | |
| 2005/0096365 A1 | 5/2005 | Fikstad et al. | |
| 2005/0100608 A1 | 5/2005 | Ebert | |
| 2005/0171193 A1 | 8/2005 | Chen et al. | |
| 2005/0176692 A1 | 8/2005 | Amory et al. | |
| 2005/0209345 A1 | 9/2005 | Charman | |
| 2005/0220825 A1 | 10/2005 | Funke et al. | |
| 2005/0287203 A1 | 12/2005 | De Nijs et al. | |
| 2005/0287212 A1 | 12/2005 | Dong et al. | |
| 2006/0003002 A1 | 1/2006 | Fikstad et al. | |
| 2006/0034937 A1 | 2/2006 | Patel | |
| 2006/0051406 A1 | 3/2006 | Parmar | |
| 2006/0106004 A1 | 5/2006 | Brody et al. | |
| 2006/0142257 A1 | 6/2006 | Nieschlag | |
| 2006/0172014 A1 | 8/2006 | Curd | |
| 2007/0110777 A1 | 5/2007 | Joabsson et al. | |
| 2007/0134336 A1 | 6/2007 | Worle et al. | |
| 2007/0232548 A1 | 10/2007 | Taneja | |
| 2008/0020053 A1 | 1/2008 | Persson et al. | |
| 2008/0217692 A1 | 9/2008 | Anderson et al. | |
| 2008/0317844 A1 | 12/2008 | Dudley et al. | |
| 2008/0317850 A1 | 12/2008 | Hewitt et al. | |
| 2009/0074859 A1 | 3/2009 | Patel | |
| 2010/0136105 A1 | 6/2010 | Chen et al. | |
| 2010/0137271 A1 | 6/2010 | Chen et al. | |
| 2010/0173882 A1 | 7/2010 | Giliyar et al. | |
| 2011/0039814 A1 | 2/2011 | Huatan et al. | |
| 2011/0142945 A1 | 6/2011 | Chen et al. | |
| 2011/0160168 A1 | 6/2011 | Dhingra | |
| 2011/0251167 A1 | 10/2011 | Dudley et al. | |
| 2012/0135074 A1 | 5/2012 | Chandrashekar | |
| 2012/0244215 A1 | 9/2012 | Giliyar et al. | |
| 2012/0322780 A1 | 12/2012 | Giliyar et al. | |
| 2013/0052263 A1 | 2/2013 | Fikstad et al. | |
| 2014/0178466 A1 | 6/2014 | Giliyar et al. | |
| 2014/0179652 A1 | 6/2014 | Giliyar et al. | |
| 2015/0064243 A1 | 3/2015 | Chen et al. | |

FOREIGN PATENT DOCUMENTS

| | | |
|---|---|---|
| EP | 0036145 B1 | 5/1985 |
| EP | 0184942 B1 | 8/1990 |
| EP | 0537070 | 4/1993 |
| EP | 0724877 B1 | 6/2000 |
| EP | 0 904 064 B1 | 10/2001 |
| EP | 1103252 B1 | 3/2003 |
| EP | 1624855 A1 | 8/2006 |
| EP | 1879456 A1 | 1/2008 |
| EP | 2000130 A1 | 12/2008 |
| FR | 2647346 | 11/1990 |
| FR | 2758459 | 7/1998 |
| GB | 1 264 677 | 2/1972 |
| GB | 2098865 A1 | 12/1982 |
| GB | 2 228 198 A | 8/1990 |
| JP | 01139526 A1 | 6/1989 |
| JP | Hei 01-139526 | 6/1989 |
| JP | 5194209 | 8/1993 |
| JP | Hei 07-041422 | 2/1995 |
| JP | 09241152 A1 | 9/1997 |
| JP | Hei 09-241152 | 9/1997 |
| JP | Hei 11049664 | 2/1999 |
| JP | 11152227 | 6/1999 |
| JP | 2001-508445 | 6/2001 |
| JP | 2002-510311 | 4/2002 |
| JP | 2002-520377 | 7/2002 |
| JP | 2003-500368 | 1/2003 |
| JP | 07041422 A1 | 2/2005 |
| JP | 2008-540451 | 11/2008 |
| WO | WO82/01649 | 5/1982 |
| WO | WO-1982-01649 | 5/1982 |
| WO | WO84/02076 | 6/1984 |
| WO | WO88/00059 | 1/1988 |
| WO | WO-1992-18147 | 10/1992 |
| WO | WO-1993-02664 | 2/1993 |
| WO | WO93/06921 | 4/1993 |
| WO | WO-1993-25192 | 12/1993 |
| WO | WO-1994-08610 | 4/1994 |
| WO | WO94/25068 | 11/1994 |
| WO | WO-1995-01785 | 1/1995 |
| WO | WO-1995-01786 | 1/1995 |
| WO | WO-1995-24893 | 9/1995 |
| WO | WO95/34287 | 12/1995 |
| WO | WO96/17597 | 6/1996 |
| WO | WO97/04749 | 2/1997 |
| WO | WO97/40823 | 11/1997 |
| WO | WO97/48382 | 12/1997 |
| WO | WO98/00116 | 1/1998 |
| WO | WO98/30205 | 7/1998 |
| WO | WO98/33512 | 8/1998 |
| WO | WO-1998-38984 | 9/1998 |
| WO | WO-1998-50077 | 11/1998 |
| WO | WO-1998-56357 | 12/1998 |
| WO | WO99/00111 | 1/1999 |
| WO | WO99/29300 | 6/1999 |
| WO | WO99/40904 | 8/1999 |
| WO | WO99/48498 | 9/1999 |
| WO | WO-1999-44584 | 9/1999 |
| WO | WO00/03753 | 1/2000 |
| WO | WO00/16749 | 3/2000 |

(56) References Cited

FOREIGN PATENT DOCUMENTS

| | | |
|---|---|---|
| WO | WO00/25772 | 5/2000 |
| WO | WO00/37057 | 6/2000 |
| WO | WO-2000-50007 A1 | 8/2000 |
| WO | WO00/57859 | 10/2000 |
| WO | WO00/57918 | 10/2000 |
| WO | WO-2000-59482 A1 | 10/2000 |
| WO | WO-2000-59512 A1 | 10/2000 |
| WO | WO00/72825 | 12/2000 |
| WO | WO00/76482 | 12/2000 |
| WO | WO-2001-01960 A1 | 1/2001 |
| WO | WO-2001-12155 A1 | 2/2001 |
| WO | WO01/21154 | 3/2001 |
| WO | WO-2001-28555 A1 | 4/2001 |
| WO | WO-2001-37808 A1 | 5/2001 |
| WO | WO01/49262 | 7/2001 |
| WO | WO-2002-39983 A2 | 5/2002 |
| WO | WO-2003-068186 A1 | 8/2003 |
| WO | WO-2004-087052 A2 | 10/2004 |
| WO | WO-2004-105694 A2 | 12/2004 |
| WO | WO-2005-041929 A1 | 5/2005 |
| WO | WO-2006-013369 A2 | 2/2006 |
| WO | WO-2006-113505 A2 | 10/2006 |
| WO | WO-2006-119498 A2 | 11/2006 |
| WO | WO-2007-018943 A2 | 2/2007 |
| WO | WO-2010-081032 | 7/2010 |
| WO | WO-2011-082384 A2 | 7/2011 |
| WO | WO-2011-129812 A1 | 10/2011 |
| WO | WO-2012-075081 A2 | 7/2012 |

OTHER PUBLICATIONS

Hutchison, K. "Digestible Emulsions and Micoremulsions for Optimum Oral Delivery of Hydrophobic Drugs," Bulletin Technique Gattefosse 87:67-74 (1994).
Langer, "New Methods of Drug Delivery," Science 249:1527-1533 (1990).
Merck Index (12$^{th}$ ed), "Fenofibrate" (Monograph 4019), Merck & Co., Inc., 1996, p. 675.
Merck Index (11$^{th}$ ed) "Vitamin E" and "Vitamin E Acetate", Monographs 9931 and 9932, Merck & Co., Inc., 1989, p. 1579-1580.
Nieschlag et al., "Plasma Androgen Levels in Men after Oral Administration of Testosterone or Testosterone Undecanoate," Acta Endocrinol. 79(2):366-374 (1975) (Abstract).
Osol, ed., Remington's Pharmaceutical Sciences (15$^{th}$ ed), 1975, Mack Publishing Co., pp. 327-339, 1452-1456.
Saudek et al., "A preliminanry trial of the programmable implantable medicatio system for insulin delivery," N. Eng. J. Med. 321:574-579 (1989).
Schott, "Comments on Hydrophile-Lipophile Balance Systems," J. Pharm. Sci. 79(1):87-88 (1990).
Schnabel et al., "The effect of food composition on serum testosterone levels after oral administration of Andriol Testocaps," Clinical Endocrinology 66(4):570-585 (2007).
Sefton, "Implantable pumps," CRC Crit. Rev. Biomed. Eng. 14(3):201-240 (1987).
Shanghai Pi Chemicals Ltd. "Material Safety Data Sheet: Testosterone Undecanoate," Online 2007, retrieved Jun. 3, 2009 from http://www.pipharm.com/products./msds/msds-13457.pdf.
Stedman's Medical Dictionary (22$^{nd}$ Ed.), "Surfactants" 1972, Williams and Wilkins Co., p. 1225.
Stedman's Medical Dictionary (22$^{nd}$ Ed.), "Dehydro-e-epiandrosterone", "Dehydroisoandrosterone" and "Steroid", Williams and Wilkins, 1973, p. 329 and 1195-1197.
Tauber, U. et al., "Absolute bioavailability of testosterone after oral administration of testosterone-undecanoate and testosterone," Eur. J. Drug. Metabolism and Pharmacokinetics 11(2):145-149 (1986).
Wilson, C.G. and O'Mahony, B., "The Behaviour of Fats and Oils in the Upper G.I. Tract," Bulletin Technique Gattefosse 90:13-18 (1997).

Zhi et al., "Effects of dietary fat on drug absorption," Clin. Pharmacol. & Ther. 58:487-491 (1995).
Supplementary EP Search Report for EP04753162 dated Apr. 13, 2010.
PCT/US04/16286 Search Report dated May 8, 2006.
Leichtnam et al., "Testosterone Hormone Replacement Therapy: State-of-the-Art and Emerging Technology," Pharma. Res. 23(6):1117-1132 (2006).
PCT/US10/20538 Search Report and Written Opinion dated Sep. 13, 2010.
Alvarez, F. J. and Stella, V. J., "The Role of Calcium Ions and Bile Salts on the Pancreatic Lipase-Catalyzed Hydrolysis of Triglyceride Emulsions Stabilized with Lecithin", Pharmaceutical Research, 6(6), 449-457 (1989).
Aungst (2000), "Intestinal Permeation Enhancers," Journal of Pharmaceutical Sciences 89(4):429-442.
Baluom et al. (1998), "The Importance of Intestinal Residence Time of Absorption Enhancer on Drug Absorption and Implication on Formulative Considerations," International Journal of Pharmaceutics 176:21-30.
Bates, T. R. and Sequeira, J. A., "Bioavailability of Micronized Griseofulvin from Corn Oil-in-Water Emulsion, Aqueous Suspension, and Commercial Tablet Dosage Forms in Humans", Journal of Pharmaceutical Sciences, 64(5), 793-797 (1975).
Bernkop-Schnurch (1998), "The Use of Inhibitory Agents to Overcome the Enzymatic Barrier to Perorally Administered Therapeutic Peptides and Proteins," Journal of Controlled Release 52:1-16.
Charman, W. N., Porter, C.J.H., Mithani, S., and Bressman, J.B., "Physicochemical and Physiological Mechanisms for the Effects of Food on Drug Absorption: The Role of Lipids and pH", Journal of Pharmceutical Sciences, 86(3), 269-282 (1997).
Gennaro, A. R., Remington's Pharmaceutical Sciences, Chapter 20, 293-300 (1985).
Horter, D. and Dressman, J.B., "Influence of Physicochemical Properties on Dissolution of Drugs in the Gastrointestinal Tract", Advanced Drug Delivery Reviews 25, 3-14 (1997).
Humberstone, A. J. and Charman, W. N. "Lipid-based Vehicles for the Oral Delivery of Poorly Water Soluble Drugs", Advanced Drug Delivery Reviews, 103-128 (1997).
Johnson, L. R., "Gastrointestinal Physiology", Department of Physiology, University of Texas Medical School, Houston, Texas, 25-26, 93, 106, 133-134, 136-137 (1997).
Julien, R.M., A Primer of Drug Action (Ninth Edition), 2001, p. 5-6.
LeCluyse et al. (1997), "In Vitro Models for Selection of Development Candidates. Permeability Studies to Define Mechanisms of Absorption Enhancement," Advanced Drug Delivery Reviews 23:163-183.
MacGregor, K. J et al., "Influence of Lipolysis on Drug Absorption From the Gastro-intestinal Tract", Advanced Drug Delivery Reviews 25, 33-46 (1997).
Muranishi (1977), "Potential Absorption of Heparin from the Small Intestine and the Large Intestine in the Presence of Monoolein Mixed Micelles," Chem. Pharm. Bull. 24(5): 1159-1161.
Muranishi (1990), "Absorption Enhancers," Critical Reviews in Therapeutic Drug Carrier Systems 7(1):1-33.
Pouton, C. W., "Formulation of Self-Emulsifying Drug Delivery Systems", Advanced Drug Delivery Reviews 25, 47-58 (1997).
Reymond, J. and Sucker, H., "In Vitro Model for Ciclosporin Intestinal Absorption in Lipid Vehicles", Pharmaceutical Research, 5(10), 677-679.
Tarr, D. T. and Yalkowsky, S. H. "Enhanced Intestinal Absorption of Cyclosporine in Rats Through the Reduction of Emulsion Droplet Size", Pharmaceutical Research, 6(1), 40-43 (1989).
Treat, et al., "Liposomes in the Therapy of Infectious Diseases and Cancer", Lopez-Berestein and Fidler (eds.), Liss, New York, (1989), 353-365.
Winne, D., "Dependence of Intestinal Absorption in Vivo on the Unstirred Layer", Archives of Pharmacology, 304, 175-181 (1978).
Office Action dated Sep. 29, 2009 in co-pending U.S. Appl. No. 12/326,711.
Office Action dated Mar. 30, 2011 in co-pending U.S. Appl. No. 12/326,711.

(56) References Cited

OTHER PUBLICATIONS

Final Office Action dated Nov. 9, 2010 in co-pending U.S. Appl. No. 12/326,711.
Final Office Action dated Sep. 16, 2011 in co-pending U.S. Appl. No. 12/326,711.
Office Action dated Sep. 2, 2008 in U.S. Appl. No. 11/196,805.
PCT International Search Report and Written Opinion of the international searching authority dated Feb. 16, 2007 in connection with PCT/US2006/027159 filed on Jul. 12, 2006.
Office Action dated Jun. 9, 2009 in co-pending U.S. Appl. No. 11/122,788.
Final Office Action dated Dec. 9, 2009 in co-pending U.S. Appl. No. 11/122,788.
PCT International Search Report and Written Opinion of the international searching authority dated Jul. 12, 2007 in connection with PCT/US2006/017445 filed on May 4, 2006.
Supplementary European Search Report dated Mar. 11, 2010 in connection with EP06759173.5 (EP1879456).
Office Action dated Jul. 13, 2005 in U.S. Appl. No. 10/764,016.
Office Action dated Dec. 19, 2006 in U.S. Appl. No. 10/764,016.
Office Action dated Sep. 7, 2007 in U.S. Appl. No. 10/764,016.
Office Action dated Apr. 24, 2008 in U.S. Appl. No. 10/764,016.
Final Office Action dated Apr. 20, 2006 in U.S. Appl. No. 10/764,016.
Final Office Action dated Feb. 23, 2009 in U.S. Appl. No. 10/764,016.
Shackleford et al., Contribution of Lymphatically Transported Testosterone Undecanoate to the Systemic Exposure of Testosterone after Oral Administration of Two Andriol Formulations in Conscious Lymph Duct-Cannulated Dogs. The Journal of Pharmacology and Experimental Therapeutics. vol. 306, No. 3 (2003).
Office Action dated Mar. 4, 2014 in U.S. Appl. No. 13/592,258.
Office Action dated Mar. 10, 2014 in U.S. Appl. No. 12/625,284.
"Emulsion", IUPAC Compendium of Chemical Terminology $2^{nd}$ Ed., 1997.
"Hydroxy Acid" and "Vitamin E", *Stedman's Medical Dictionary* ($22^{nd}$ Ed), The Williams and Wilkins Company, 1973, p. 595 and 1400, Baltimore.
"*Liposomes in the Therapy of Infectious Disease and Cancer*." 1989, LopezBerestein and Fidler (Eds)., pp. 353-365, Liss, New York.
Addo et al., "Non-polar extracts of serum from males contain covert radioimmunoassayable testosterone." *Steroids*, Sep. 1989, 54(3): 257-69.
Andriol® Testocaps™ Consumer Medicine Information, Sep. 2003.
Atkinson et al. "Long Term experience with testosterone replacement through scrotal skin." *Testosterone: Action, Deficiency and Substitution* (Nieschlag, E. and Behre, HM, eds.) 1998, Springer-Verlag, Berlin pp. 365-388.
Bhargava et al. "Using microemulsions for drug delivery." *Pharmaceutical Technology*, Mar. 1987, pp. 46-53.
Burbello et al., Sovremennye lekarstvennyesredstva S-Pb "Neva", 2004, p. 567.
Cantrill, J.A. "Which Testosterone Replacement Therapy?" *Clinical Endocrinol* (1984) 21: 97-107.
Charman, W. N., Porter, C.J.H., Mithani, S., and Bressman, J.B., "Physicochemical and Physiological Mechanisms for the Effects of Food on Drug Absorption: The Role of Lipids and pH", Journal of Pharuceutical Sciences, 86(3), 269-282 (1997).
Constantinides, P., "Lipid Microemulsions for Improving Drug Dissolution and Oral Absorption: Physical and Biopharmaceutical Aspects." *Pharmaceutical Research*, 1995, , 12(11):1561-1572.
EP10729592.5 Extended Search Report dated Aug. 27, 2012.
Final Office Action dated Mar. 28, 2011 in co-pending U.S. Appl. No. 12/350,930.
Frey et al., "Bioavailability of Oral testosterone in Males," Eur. J. Pharmacol. 16, 345-349 (1979).
Gooren, Ljg "A ten year safety study of the oral androgen testosterone undecanoate." *J. Androl.*, 1994, 15: 212-215.
Graham-Smith et al., "The Oxford Reference-book in Clinical Pharmacology and Pharmacotherapy," *M. Meditsina Publishers*, 2000, pp. 25, 136-137 (incl Eng version).

Javanbakht et al., "Pharmacokinetics of a novel testosterone matrix transdermal system in healthy, premenopausal women and women infected with the human immunodeficiency virus." Journal of Clinical Endocrinology & Metabolism, 2000: 85(7):2395-401.
Kalinchenko, S. Yu "Testosteron-korol' gormonov I gormon korolei." The Journal "Sex and Life", 2004, pp. 12-22 [online] [retrieved on Mar. 26, 2010 13:27]. Retrieved front the Internet: URL: http://www/laz.med.ru/interesting/publications/testosteron.html.
Maisey et al., Clinical Efficacy of Testosterone Undecanoate in Male Hypogonadism, *Clinical Endocrinology*, 1981, , vol. 14, pp. 625-629.
McAuley et al. "Oral Administration of Micronized Progesterone: a Review and More Experience." *Pharmacotherapy*, May 1996, 16(3):453-457.
Meiner and Tonascia, "Clinical Trials: Design, Conduct, and Analysis," *Monographs in Epidemiology and Biostatistics*, 1986, vol. 8.
Merck Index, "Alpha Tocopherol", Monograph 09571, Merck & Co. 2001-2004.
Merck Index, "Carvedilol", Monograph 01888, Merck & Co. 2001-2004.
Merck Index, "Risperidone", Monograph 08316, Merck & Co. 2001-2004.
Merck Index, "Ziprasidone", Monograph 10224, Merck & Co. 2001-2004.
Merck Index, $12^{th}$ Ed., "Amiodarone", Monograph 504, Merck & Co. 1996, p. 84.
Merriam-Webster Dictionary [Online]. "Granule". [Retrieved Dec. 17, 2009], Retrieved from the Internet: <URL: http://www.mw.com/dictionary/granule>.
Mittal and Mukerjee, "The Wide World of Micelles." *International Business Machines Corporation and School of Pharmacy*, University of Wisconsin, Madison, 1976, vol. 1 Wisconsin; pp. 1-21.
Noguchi T. et al., "The effect of drag lipophilicity and lipid vehicles on the lympathics absorption of various testosterone esters." *International Journal of Pharmaceutics*, 1985, 24:173-184.
Office Action dated Apr. 20, 2009 in co-pending U.S. Appl. No. 10/444,935.
Office Action dated Apr. 29, 2011 in co-pending U.S. Appl. No. 10/444,935.
Office Action dated Aug. 4, 2010 in co-pending U.S. Appl. No. 10/444,935.
Office Action dated Feb. 8, 2008 in co-pending U.S. Appl. No. 10/444,935.
Office Action, dated Jan. 11, 2010 in co-pending U.S. Appl. No. 10/444,935.
Office Action dated Jul. 24, 2008 in U.S. Appl. No. 10/764,016.
Office Action dated Jul. 6, 2005 in co-pending U.S. Appl. No. 10/444,935.
Office Action dated Mar. 7, 2006 in co-pending U.S. Appl. No. 10/444,935.
Office Action dated Nov. 2, 2006 in co-pending U.S. Appl. No. 10/444,935.
Office Action dated Nov. 29, 2010 in co-pending U.S. Appl. No. 12/350,930.
Office Action dated Oct. 28, 2008 in co-pending U.S. Appl. No. 10/444,935.
PCT/US2010/030788 International Search Report dated Dec. 1, 2010.
Remington: The Science and Practice of Pharmacy (19th Ed.) 1995, "Surfactant Properties in Solution and Micelle Formation," pp. 272-276.
Supplementary European Search Report for EP 10173114.9 dated Apr. 14, 2011.
Swerdoff, et al "Long term pharmaceokinetics of transdermal testosterone gel in hypogonadal men." J. Clin. Endocrinol. Metab. 2000, 85:4500-4510.
Tenover, JL, "The Androgen-Deficient Aging Male : Current Treatment Options." Reviews in Urology, 2003, vol. 5, Suppl. 1, S22-S28.
Tso, et al., "Intestinal Absorption and Lymphatic Transport of a High γ-Linolenic Acid Canola Oil in Lymph Fistula Sprague-Dawlwy Rats." *American Society for Nutritional Sciences*, 2002, pp. 218-221.

(56) References Cited

OTHER PUBLICATIONS

Wang, et al. "Long-term testosterone gel (AndroGel®) treatment maintains beneficial effects on sexual function and mood, lean and fat mass and bone mineral density in hypogonadal men." *J. Clin. Metab.*, 2004, 89:2085-2098.
Yassin et al. "Long-acting testosterone undecanoate for parenteral testosterone therapy." Therapy, Future Drugs, 2006, 3(6):709-721.
Yin et al., "Dietary Fat Modules Testosterone Pharmacokinetics of a New Self-Emulsifying Formulation of Oral Testosterone Undercanoate in Hypogonadal Men." *Submitted Journal of Andrology*, submitted Mar. 23, 2012, published ahead of print on Jul. 12, 2012.
Yin et al., "Reexamination of Pharmacokinetics of Oral Testosterone Undercanoate in Hypogonadal Men with a New Self-Emulsifying Formulation." *Journal of Andrology*, 2012, 33( 2):190-201.
Office action dated Jan. 4, 2012 for U.S. Appl. No. 12/625,284.
Office action dated Jan. 26, 2013 for U.S. Appl. No. 13/592,258.
Office action dated Jan. 27, 2012 for U.S. Appl. No. 12/625,309.
Office action dated Feb. 13, 2013 for U.S. Appl. No. 12/625,309.
Office action dated Mar. 19, 2013 for U.S. Appl. No. 13/592,258.
Office action dated Jul. 24, 2012 for U.S. Appl. No. 12/625,284.
Office action dated Aug. 6, 2012 for U.S. Appl. No. 12/625,309.
Office action dated Oct. 26, 2012 for U.S. Appl. No. 13/592,258.
Office action dated Dec. 1, 2011 for U.S. Appl. No. 10/444,935.
Hong, B.S., et al., Recent trends in the treatment of testosterone deficiency syndrome. International Journal of Urology, (2007) 14; 981-985.
Office Action dated Aug. 6, 2013 in for U.S. Appl. No. 13/592,258.
Office Action dated Sep. 23, 2013 in for U.S. Appl. No. 10/444,935.
Perchersky, A.V., et al. "Androgen administration in middle-aged and ageing men: effects of oral testosterone undecanoate on dihydrotestosterone, oestradiol and prostate volume." International Journal of Andrology, 25: 119-125 (2002).
U.S. Appl. No. 13/663,352 Office Action dated Jan. 10, 2014.
Yassin et al., "Testosterone undecanoate for parenteral testosterone therapy", Therapy, Future drugs, 3/6, pp. 709-721 Nov. 2006.
Bagchus et al. (2003), "Important Effect of Food on the Bioavailability of Oral Testosterone Undecanoate," Pharmacotherapy 23(3): 319-325.
Merck Index, 12th Ed., "Shellac", Monograph 8623, Merck & Co. 1996, p. 1457.
Merck Index, 12th Ed., "Testosterone", Monograph 9322, Merck & Co. 1996, p. 1569.
Moellering RC. "Vancomycin: A 50-Year Reassessment". Clinical Infectious Diseases. 2006; 42:S3-S4.
Office Action dated May 6, 2014 in U.S. Appl. No. 11/122,788.
Office Action dated Jul. 8, 2014 in U.S. Appl. No. 14/191,249.
Office Action dated Jul. 8, 2014 in U.S. Appl. No. 14/191,278.
Office Action dated Jul. 23, 2014 in U.S. Appl. No. 13/663,352.
U.S. Appl. No. 14/191,249 Final Office Action dated Nov. 20, 2014.
U.S. Appl. No. 12/625,284 Final Office Action dated Dec. 8, 2014.
U.S. Appl. No. 14/535,536 Office Action dated Feb. 5, 2015.
U.S. Appl. No. 11/122,788 Final Office Action dated Feb. 11, 2015.
Andriol® Testocaps®; "Testosterone Undecanoate;" Product Information; (Jun. 2011); 8 pages; RA 1410 OS S6 ref. 4.0.
Nieschlag; "Testosterone Treatment Comes of Age: New Options for Hypogonadal Men;" Clinical Endocrinology; (2006); pp. 275-281; vol. 65; <doi: 10.1111/j.1365-2265.2006.02618.x >.
Notice to Declare Interference: *Claras Therapeutics, Inc.* (Junior Party U.S. Appl. No. 16/818,779) v. *Lipocine, Inc.* (Senior Party U.S. Appl. No. 16/818,779); Patent Interference No. 106,128 (DK); filed Jan. 4, 2021; 9 pages.
Junior Party Clarus' Motion 2 [*Claras Therapeutics, Inc.* (Junior Party U.S. Appl. No. 16/818,779) v. *Lipocine, Inc.* (Senior Party U.S. Appl. No. 16/818,779); Patent Interference No. 106,128 (DK)]; filed Mar. 26, 2021; 32 pages.
Junior Party Clarus' Motion 3 [*Claras Therapeutics, Inc.* (Junior Party U.S. Appl. No. 16/818,779) v. *Lipocine, Inc.* (Senior Party U.S. Appl. No. 16/818,779); Patent Interference No. 106,128 (DK)]; filed Mar. 26, 2021; 26 pages.
Junior Party Claras' Motion 4 [*Claras Therapeutics, Inc.* (Junior Party U.S. Appl. No. 16/818,779) v. *Lipocine, Inc.* (Senior Party U.S. Appl. No. 16/818,779); Patent Interference No. 106,128 (DK)]; filed Mar. 26, 2021; 31 pages.

\* cited by examiner

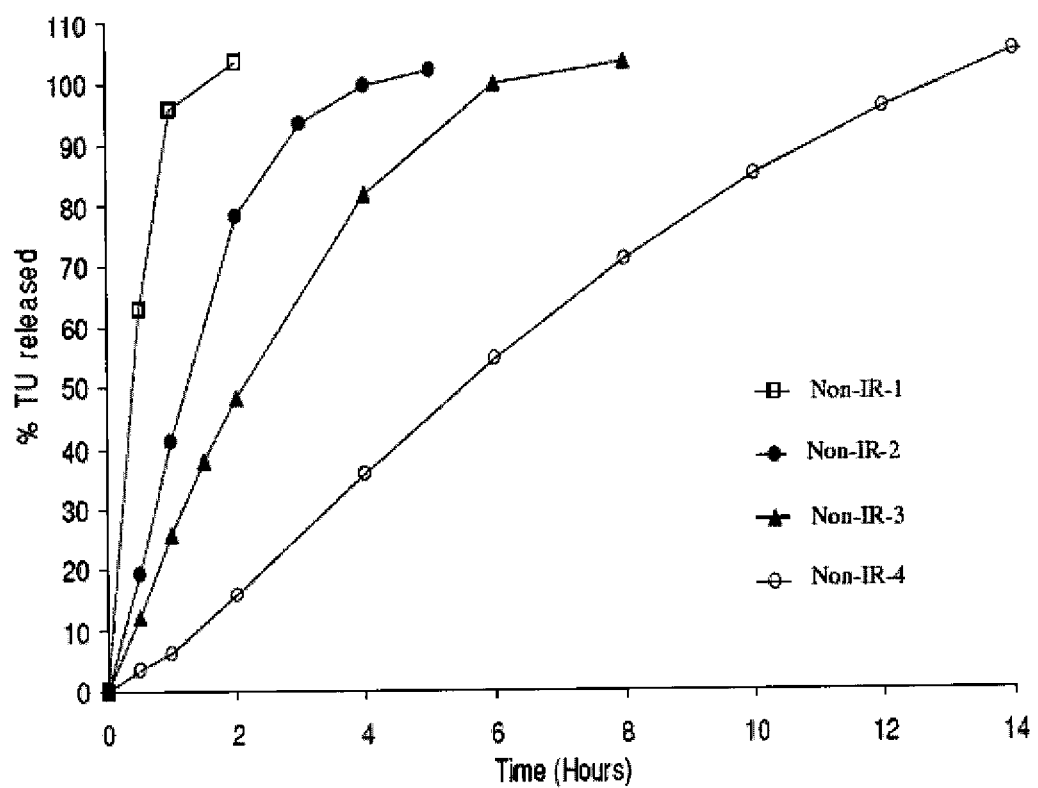

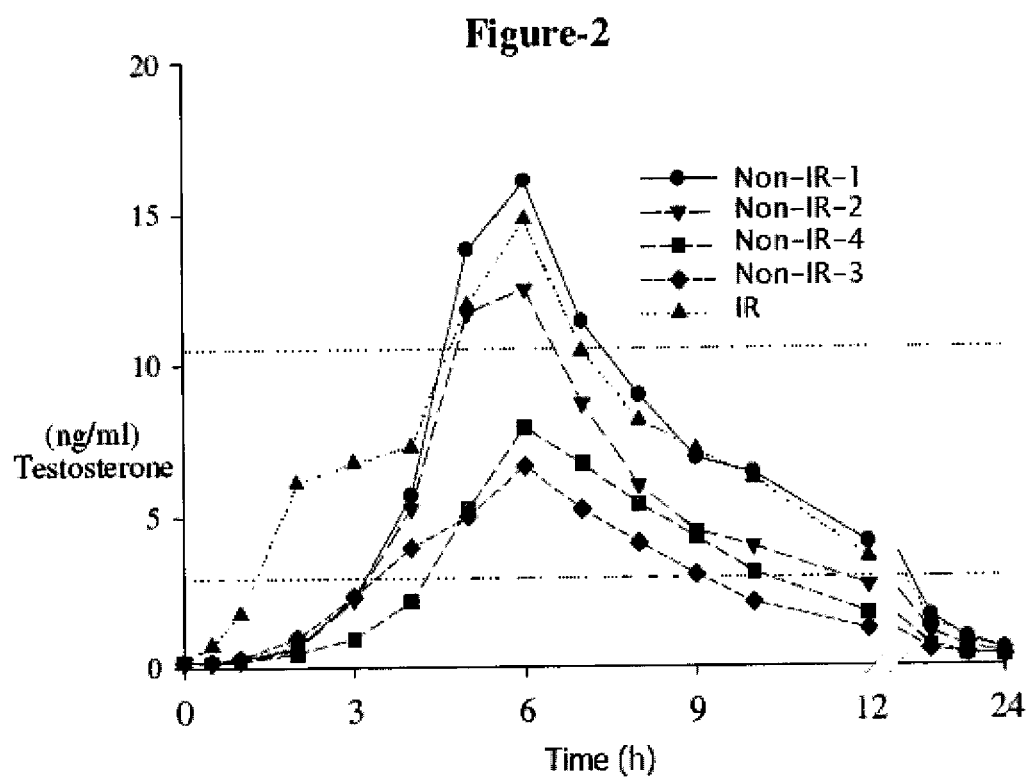

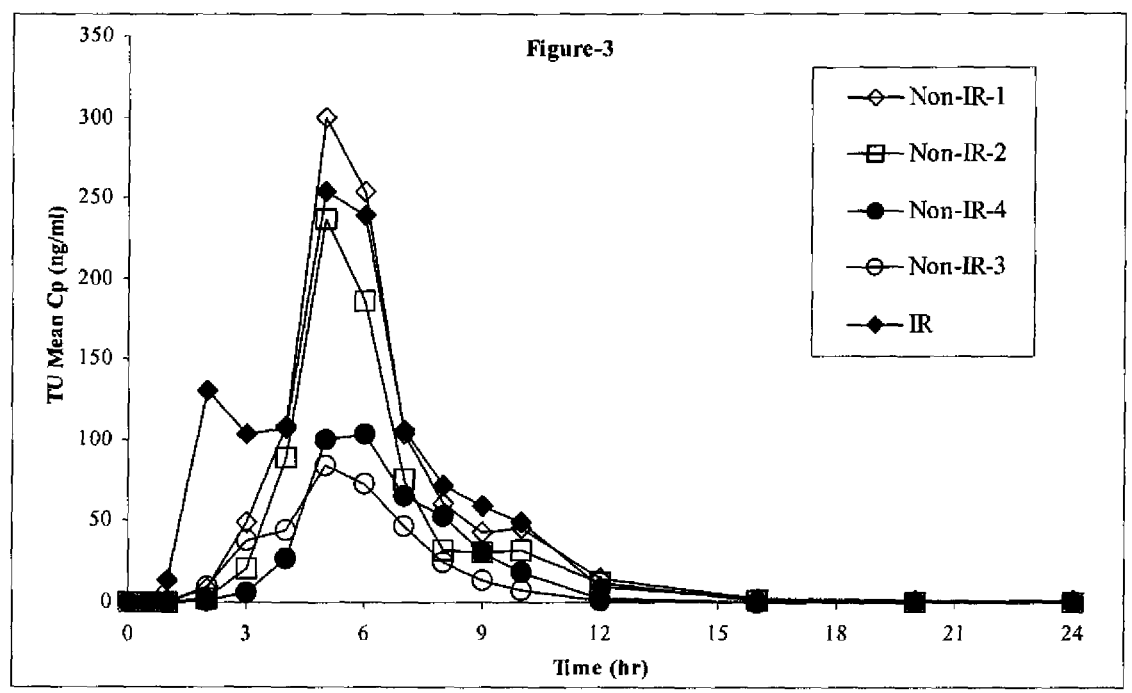
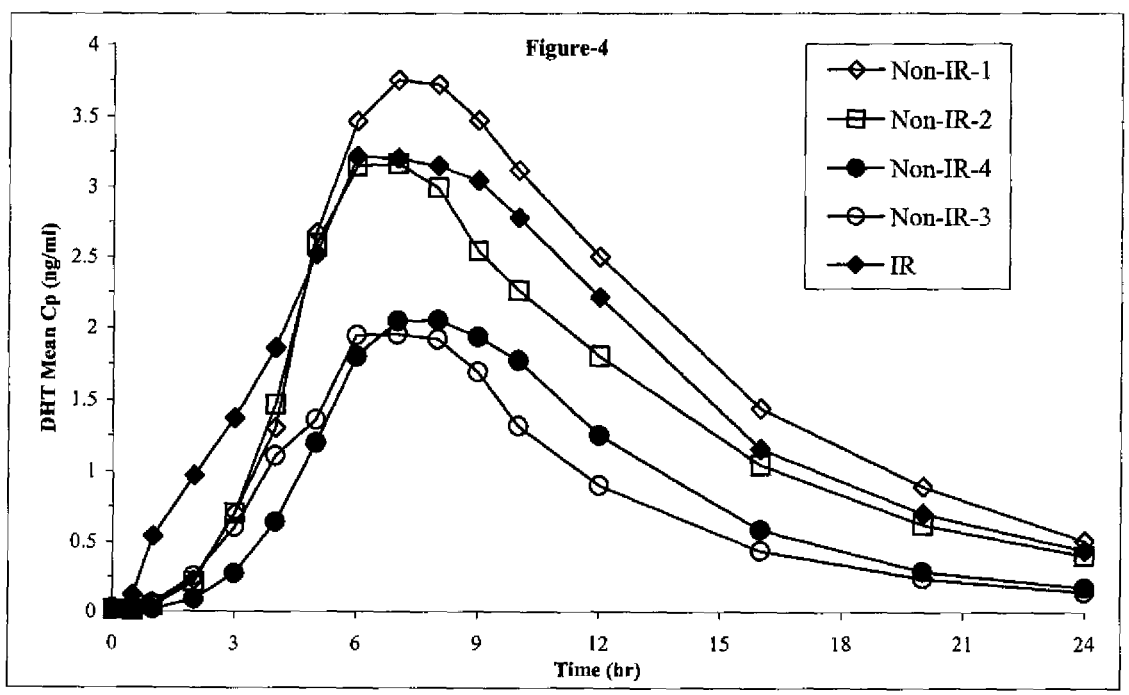

__

STEROIDAL COMPOSITIONS

BACKGROUND OF THE INVENTION

Testosterone is an androgenic compound crucial for human health. Certain embodiments of the invention described herein generally relate to compositions for the administration of testosterone, testosterone analogs, other steroids and related compounds.

SUMMARY OF THE INVENTION

Provided in certain embodiments herein is a delayed release oral dosage form comprising a therapeutically effective amount of one or more testosterone alkyl ester and at least one pharmaceutically acceptable carrier, wherein a single dose of the delayed release oral dosage form provides a mean plasma $C_{max}$ of testosterone that is at least 5%, at least 10% or at least 15% lower than the mean plasma $C_{max}$ of testosterone that is provided by a single dose of an immediate release oral dosage form having an identical amount of the testosterone alkyl ester. In some embodiments, provided herein is a delayed release oral dosage form, wherein a single dose of the delayed release oral dosage form provides a mean plasma $C_{max}$ of testosterone alkyl ester that is at least 5%, at least 10% or at least 15% lower than the mean plasma $C_{max}$ of testosterone alkyl ester that provided by a single dose of an immediate release oral dosage form having an identical amount of the testosterone alkyl ester. In certain embodiments, a single dose of the delayed release oral dosage form described herein provides a mean plasma $C_{max}$ of that is at least 5% lower than the mean plasma $C_{max}$ of dihydrotestosterone provided by a single dose of an immediate release oral dosage form having an identical amount of the testosterone alkyl ester. In some embodiments, a delayed release oral dosage form described herein provides a mean plasma $C_{max}$ at steady state of testosterone alkyl ester that is at least 5%, at least 10% or at least 15% lower than the mean plasma $C_{max}$ of testosterone alkyl ester at steady state provided by an immediate release oral dosage form having an identical amount of the testosterone allkyl ester. In certain embodiments, a delayed release oral dosage form described herein provides a fluctuation index of testosterone at steady state that is at least 5%, or at least 10% lower than a fluctuation index of testosterone at steady state of an immediate release oral dosage form having an identical amount of the testosterone alkyl ester. In some embodiments, a delayed release oral dosage form described herein provides a fluctuation index of testosterone alkyl ester at steady state that is at least 5%, or at least 10% lower than a fluctuation index of testosterone alkyl ester at steady state of an immediate release oral dosage form having an identical amount of the testosterone alkyl ester. In some embodiments, a single dose of the delayed release oral dosage form provides a mean plasma concentration of testosterone provided 1 hour after oral administration of the delayed release oral dosage form that is at least 20% lower than a mean plasma concentration of testosterone provided 1 hour after oral administration of a single dose of an immediate release oral dosage form having an identical amount of the testosterone alkyl ester.

Provided in certain embodiments herein is a pharmaceutical composition comprising a therapeutically effective amount of one or more testosterone alkyl ester and at least one pharmaceutically acceptable carrier. In some embodiments, a single dose of a pharmaceutical composition described herein provides a mean plasma $C_{max}$ of testosterone that is about 15 ng/mL or less; or about 19 ng/mL or less upon oral administration. In certain embodiments, a single dose of a pharmaceutical composition described herein provides a mean plasma $C_{max}$ of dihydrotestosterone that is about 4.5 ng/mL, or about 3.6 ng/mL or less upon oral administration. In some embodiments, a pharmaceutical composition described herein provides a testosterone mean plasma $C_{max}$ at steady state of about 1300 ng/dL or less. In certain embodiments, a pharmaceutical composition described herein provides a testosterone mean plasma $C_{min}$ at steady state of about 200 ng/dL or more. In some embodiments a pharmaceutical composition provides with administration to an individual a ratio of the testosterone equivalent dose from the alkyl ester, to a mean steady state testosterone $C_{max}$, the ratio being about $500 \times 10^6$ mL or less. In certain embodiments, the difference between the mean plasma $C_{max}$ of testosterone at steady state and mean plasma $C_{min}$ of testosterone at steady state provided by a pharmaceutical composition described herein is about 11 ng/mL or less, or about 16 ng/mL or less. In some embodiments, the difference between the mean plasma $C_{max}$ at steady state and mean plasma $C_{min}$ at steady state of testosterone alkyl ester provided by a pharmaceutical composition described herein is about 275 ng/mL or less; or about 200 ng/mL or less. In certain embodiments, a single dose of a pharmaceutical composition described herein provides a mean plasma concentration of testosterone after 1 hour that is about 150 ng/dL or less upon oral administration. In some embodiments, a single dose of a pharmaceutical composition described herein provides a mean plasma concentration of testosterone after 2 hours that is about 500 ng/dL or less upon oral administration.

In certain embodiments, a pharmaceutical composition described herein releases about 50% or less of the testosterone alkyl ester after 1 hour and/or about 80% or less of the testosterone alkyl ester after about 30 minutes in an aqueous medium. In some embodiments, a pharmaceutical composition described herein releases about 20% or less of the testosterone alkyl ester after 30 minutes in an aqueous medium. In certain embodiments, a pharmaceutical composition described herein releases less than 95% of the testosterone alkyl ester after 3 hours in an aqueous medium. In some embodiments, a pharmaceutical composition described herein releases more than 80% of the testosterone alkyl ester within 12 hours in an aqueous medium. In some instances, the aqueous medium is present in a USP Type-II (paddle) apparatus with conditions at 37±0.5° C. and at 100 rpm. In more specific instances, the aqueous medium is about 1 L of DI water having 8% w/v of Triton X-100.

In certain embodiments, described herein is a delayed release oral dosage form comprising a testosterone alkyl ester (e.g., testosterone alkyl ester formulated in solid PEG). In some embodiments, a pharmaceutical composition described herein is a delayed release oral dosage form. In certain embodiments, the delayed release oral dosage form is formulated in any suitable manner. In some embodiments, a single dose of a delayed release oral dosage form described herein provides a mean plasma $C_{max}$ of testosterone that is at least about 5%, at least 10% or at least 15% lower than the mean plasma $C_{max}$ of testosterone that is provided by a single dose of an immediate release oral dosage form having an identical amount of the testosterone alkyl ester. In certain embodiments, a single dose of a delayed release oral dosage form described herein provides a mean plasma $C_{max}$ of the testosterone alkyl ester that is at least about 5%, at least 10% or at least 15% lower than the mean plasma $C_{max}$ of testosterone alkyl ester that is provided by a single dose of an immediate release oral dosage form having an identical amount of the testosterone alkyl ester. In some embodiments, a single dose of a delayed release oral dosage form described herein provides a mean plasma $C_{max}$ of that is at least 5% lower than the mean plasma $C_{max}$ of dihydrotestosterone provided by a single dose of an immediate release oral dosage form having an identical amount of the testosterone alkyl ester. In certain embodiments, a delayed release oral dosage form described herein provides a mean plasma $C_{max}$ at steady state of testosterone alkyl ester that is at least about 5%, at least 10% or at least 15% lower than the mean plasma $C_{max}$ of testosterone alkyl ester at steady state provided by an immediate release oral dosage form having an identical amount of the testosterone alkyl ester. In some embodiments, a delayed release oral dosage form described herein provides a fluctuation index of testosterone at steady state that is at least 10% lower than a fluctuation index of testosterone at steady state of an immediate release oral dosage form having an identical amount of the testosterone alkyl ester. In certain embodiments, a delayed release oral dosage form described herein provides a fluctuation index of testosterone alkyl ester at steady state that is at least 10% lower than a fluctuation index of testosterone alkyl ester at steady state of an immediate release oral dosage form having an identical amount of the testosterone alkyl ester. In some embodiments, a single dose of a delayed release oral dosage form described herein provides a mean plasma concentration of testosterone provided 1 hour after oral administration of the delayed release oral dosage form that is at least 20% lower than a mean plasma concentration of testosterone provided 1 hour after oral administration of a single dose of an immediate release oral dosage form having an identical amount of the testosterone alkyl ester.

In some embodiments, the one or more testosterone alkyl ester provided in any pharmaceutical composition or oral dosage form described herein is or comprises testosterone undecanoate. In certain embodiments, any pharmaceutical composition or oral dosage form described herein comprises about 10 mg to about 400 mg, or about 10 mg to about 1000 mg of testosterone alkyl ester. In some embodiments, any pharmaceutical composition or oral dosage form described herein comprises about 10 mg to about 300 mg of testosterone alkyl ester. In certain embodiments, any pharmaceutical composition or oral dosage form described herein comprises about 10 mg to about 240 mg of testosterone alkyl ester. In some embodiments, any pharmaceutical composition or oral dosage form described herein comprises about 10 mg to about 150 mg of testosterone alkyl ester. In some embodiments, any pharmaceutical composition or oral dosage form described herein comprises about 120 mg of testosterone alkyl ester.

In certain embodiments, the at least one pharmaceutically acceptable carrier of any pharmaceutical composition or oral dosage form described herein comprises at least one hydrophilic carrier. In some embodiments, the at least one pharmaceutically acceptable carrier of any pharmaceutical composition or oral dosage form described herein comprises at least one lipophilic carrier. In certain embodiments, the at least one pharmaceutically acceptable carrier of any pharmaceutical composition or oral dosage form described herein comprises at least one viscosity enhancer or solidifying agent. In some embodiments, the at least one hydrophilic carrier comprises a hydrophilic triglyceride. In specific embodiments, the hydrophilic triglyceride is a polyoxylated castor oil, or a polyoxylated hydrogenated castor oil.

Provided in some embodiments herein is a method of treating androgen deficiency in an individual in need thereof by administering to the individual any oral dosage form or pharmaceutical composition described herein. In some embodiments, a pharmaceutical composition or oral dosage form described herein is administered b.i.d. In certain embodiments, a pharmaceutical composition or oral dosage form described herein is administered with a meal.

Provided in certain embodiments herein is an oral testosterone undecanoate therapy that provides to a human in need of androgen therapy by orally delivering to the human a composition comprising a therapeutically effective amount of testosterone undecanoate. In some embodiments, the oral testosterone undecanoate therapy provides in a human (e.g., a male human) a mean $C_{max}$ of testosterone that is less than about 15 ng/mL; or less than about 19 ng/mL after a single administration of the composition. In certain embodiments, the oral testosterone undecanoate therapy provides to a human (e.g., a male human) a mean plasma $C_{max}$ of dihydrotestosterone that is about 3.6 ng/mL or less; or about 4.5 ng/mL or less after a single administration of the composition. In some embodiments, the oral testosterone undecanoate therapy provides to a human (e.g., a male human) a testosterone mean plasma $C_{max}$ at steady state of about 1300 ng/dL or less. In certain embodiments, the oral testosterone undecanoate therapy provides to a human (e.g., a male human) a testosterone mean plasma $C_{min}$ at steady state of about 200 ng/dL or more. In some embodiments, the oral testosterone undecanoate therapy provides to a human (e.g., a male human) a mean $C_{max}$ of testosterone at steady state to dose ratio of about 15 or less. In specific embodiments, the ratio is 15 or less, or 13 or less. In some embodiments provided herein is a pharmaceutical composition that provides with administration to an individual a ratio of a testosterone $C_2$-$C_{13}$ alkyl ester dose, in mg, to a mean steady state testosterone $C_{max}$, in mg/mL, the ratio of testosterone equivalent dose from the testosterone alkyl ester to a mean steady state testosterone $C_{max}$, the ratio being about $500 \times 10^6$ mL or less (e.g., with b.i.d. or q.d. administration to an otherwise testosterone deficient individual). In certain embodiments, the oral testosterone undecanoate therapy provides to a human (e.g., a male human) a difference between a mean plasma $C_{max}$ of testosterone at steady state and mean plasma $C_{min}$ of testosterone at steady state of about 11 ng/mL or less, or about 16 ng/mL or less. In some embodiments, the oral testosterone undecanoate therapy provides to a human (e.g., a male human) a difference between a mean plasma $C_{max}$ at steady state and mean plasma $C_{min}$ at steady state of testosterone alkyl ester of about 200 ng/mL or less; or about 275 ng/mL or less. In certain instances, when a mean plasma concentration is utilized, the value is obtained from a statistically significant population of individuals.

Provided in certain embodiments herein is a pharmaceutical composition comprising (i) a therapeutically effective amount of one or more testosterone $C_2$-$C_{13}$ alkyl ester; and (ii) at least one pharmaceutically acceptable carrier; the pharmaceutical composition releasing about 80% or less of the testosterone $C_2$-$C_{13}$ alkyl ester after 30 minutes in an medium. In certain instances, the aqueous medium comprises 8% w/v octoxynol-9 in water at about 37° C. In some embodiments, any aqueous medium described herein is 1 L deionized water comprising 8% w/v Triton X-100 (e.g., octylphenol ethylene oxide condensate; octoxynol-9; t-octylphenoxypolyethoxyethanol; t-oct-$C_6H_4$—$(OCH_2CH_2)_xOH$, x=9-10; CAS No. 9002-93-1; Triton X-100 was a registered trademark formerly owned by Rohm and Haas Co., but now owned by Union Carbide) at 37±0.5° C. and subjected to a paddle method at 100 rpm and 37±0.5° C. for the designated period of time (USP App 2). In some embodiments, the testosterone $C_2$-$C_{13}$ alkyl ester is testosterone undecanoate. In certain embodiments, the pharmaceutical composition comprises about 10 mg to about 1000 mg of testosterone $C_2$-$C_{13}$ alkyl ester.

In some embodiments, a single dose of any pharmaceutical composition provided herein provides a mean plasma $C_{max}$ of testosterone that is about 15 ng/mL or less; or about 19 ng/mL or less upon oral administration (e.g., to a testosterone deficient individual). In certain embodiments, a single dose of any pharmaceutical composition provided herein provides a mean plasma $C_{max}$ of dihydrotestosterone that is about 4.5 ng/mL or less; or about 3.6 ng/mL or less upon oral administration (e.g., to a testosterone deficient individual). In some embodiments, any pharmaceutical composition provided herein provides a testosterone mean plasma $C_{max}$ at steady state of about 1300 ng/dL or less with oral administration (e.g., with b.i.d. or q.d. administration to an otherwise testosterone deficient individual). In certain embodiments, any pharmaceutical composition provided herein provides a testosterone mean plasma $C_{min}$ at steady state of about 200 ng/dL or more with oral administration (e.g., with b.i.d. or q.d. administration to an otherwise testosterone deficient individual). In some embodiments, any pharmaceutical composition provided herein provides with administration to an individual (e.g., oral administration) a ratio of testosterone equivalent dose from the testosterone alkyl ester to a mean a mean steady state testosterone $C_{max}$, the ratio being about 500×10$^6$ mL, or less (e.g., with b.i.d. or q.d. administration to an otherwise testosterone deficient individual).

In some embodiments, the difference between the mean plasma $C_{max}$ of testosterone at steady state and mean plasma $C_{min}$ of testosterone at steady state is about 11 ng/mL or less, or about 16 ng/mL or less (e.g., with b.i.d. or q.d. administration to an otherwise testosterone deficient individual). In some embodiments, the difference between the mean plasma $C_{max}$ at steady state and mean plasma $C_{min}$ at steady state of testosterone $C_2$-$C_{13}$ alkyl ester is about 200 ng/mL or less; or about 275 ng/mL or less (e.g., with b.i.d. or q.d. administration to an otherwise testosterone deficient individual). In some embodiments, a single dose of any pharmaceutical composition provided herein provides a mean plasma concentration of testosterone after 1 hour that is about 150 ng/dL or less upon oral administration. In certain embodiments, a single dose of any pharmaceutical composition provided herein provides a mean plasma concentration of testosterone after 2 hours that is about 500 ng/dL or less upon oral administration.

In certain embodiments, the at least one pharmaceutically acceptable carrier of any pharmaceutical composition provided herein comprises at least one hydrophilic carrier. In specific embodiments, the hydrophilic carrier is a hydrophilic triglyceride. In more specific embodiments, the hydrophilic triglyceride is a polyoxylated castor oil, or a polyoxylated hydrogenated castor oil. In some embodiments, any pharmaceutical composition provided herein consists essentially of a lipophilic carrier or combination of lipophilic carriers. In certain embodiments, any pharmaceutical composition provided herein comprises a lipophilic carrier and less than 10% w/w or less than 5% w/w of a hydrophilic carrier.

Provided in certain embodiments herein is a delayed release oral dosage form comprising (i) a therapeutically effective amount of one or more testosterone $C_2$-$C_{13}$ alkyl ester; and (ii) at least one pharmaceutically acceptable carrier; wherein a single dose of the delayed release oral dosage form provides a mean plasma $C_{max}$ of testosterone that is at least 5% lower; or at least 10% lower than the mean plasma $C_{max}$ of testosterone that is provided by a single dose of an immediate release oral dosage form having an identical amount of the testosterone $C_2$-$C_{13}$ alkyl ester. In some embodiments, the testosterone $C_2$-$C_{13}$ alkyl ester is testosterone undecanoate. In certain embodiments, the pharmaceutical composition comprises about 10 mg to about 1000 mg of testosterone $C_2$-$C_{13}$ alkyl ester.

In some embodiments, a single dose of any delayed release oral dosage form provided herein provides a mean plasma $C_{max}$ of the that is at least 5%, at least 10% or at least 15% lower than the mean plasma $C_{max}$ of testosterone $C_2$-$C_{13}$ alkyl ester that is provided by a single dose of an immediate release oral dosage form having an identical amount of the testosterone $C_2$-$C_{13}$ alkyl ester. In some embodiments, a single administration to a human of a dose of the delayed release oral dosage form provides a ratio of testosterone equivalent dose from the $C_2$-$C_{13}$ alkyl ester present in the dose of the delayed release oral dosage form to mean plasma testosterone $C_{max}$ provided by the single administration of the dose of the delayed oral release dosage form, the ratio being about 500×10$^6$ mL or less. In certain embodiments, a single dose of any delayed release oral dosage form provided herein provides a mean plasma $C_{max}$ of that is at least 5% lower than the mean plasma $C_{max}$ of dihydrotestosterone provided by a single dose of an immediate release oral dosage form having an identical amount of the testosterone $C_2$-$C_{13}$ alkyl ester. In some embodiments, a single administration to a human a dose of the delayed release oral dosage form provides a ratio of testosterone equivalent dose from the $C_2$-$C_{13}$ alkyl ester to mean plasma dihydroxytestosterone $C_{max}$ provided by the single administration of the dose of the delayed oral release dosage form, the ratio being about 350×10$^6$ mL or less. In some embodiments, any delayed release oral dosage form provided herein provides a mean plasma $C_{max}$ at steady state of testosterone $C_2$-$C_{13}$ alkyl ester that is at least 5% lower, or at least 10% lower than mean plasma $C_{max}$ of testosterone $C_2$-$C_{13}$ alkyl ester at steady state provided by an immediate release oral dosage form having an identical amount of the testosterone $C_2$-$C_{13}$ alkyl ester (e.g., when orally administered to a testosterone deficient individual b.i.d. or q.d.).

In certain embodiments, any delayed release oral dosage form provided herein comprises at least one pharmaceutically acceptable carrier that comprises at least one hydrophilic carrier. In specific embodiments, the hydrophilic carrier is a hydrophilic triglyceride. In more specific embodiments, the hydrophilic triglyceride is a polyoxylated castor oil, or a polyoxylated hydrogenated castor oil. In some embodiments, any delayed release oral dosage form provided herein consists essentially of a lipophilic carrier or combination of lipophilic carriers. In some embodiments, a lipophilic carrier selected from the group consisting of a monoglyceride, a diglyceride, a Vitamin E compound, a triglyceride, a fatty acid, polyoxylated fatty acid, polyoxylated triglyceride, polyoxylated vegetable oil, and a combination thereof. In certain embodiments, any delayed release oral dosage form provided herein comprises a lipophilic carrier and less than 10% w/w or less than 5% w/w of a hydrophilic carrier.

Provided in some embodiments herein is a pharmaceutical composition comprising (i) a therapeutically effective amount of one or more testosterone alkyl ester; and (ii) at least one pharmaceutically acceptable carrier; the pharmaceutical composition releasing about 60% to about 90%, about 60% to about 85%, or about 60% to about 80% of the testosterone alkyl ester after 1 hour in an aqueous medium. In certain instances, the aqueous medium comprises 8% w/v octoxynol-9 in water at about 37° C.

Provided in certain embodiments herein is a pharmaceutical composition comprising (i) a therapeutically effective amount of one or more testosterone alkyl ester; and (ii) at least one pharmaceutically acceptable carrier; the pharmaceutical composition releasing about 50% or less, about 45% or less, or about 40% or less of the testosterone alkyl ester after 6 hour in an aqueous medium. In certain instances, the aqueous medium comprises 8% w/v octoxynol-9 in water at about 37° C.

Provided in some embodiments herein is a method of treating androgen deficiency in an individual in need thereof by administering to the individual any pharmaceutical composition or dosage form described herein. In a specific embodiment, provided herein is a method of treating androgen deficiency in an individual in need thereof by administering to the individual a pharmaceutical composition comprising (i) a therapeutically effective amount of one or more testosterone $C_2$-$C_{13}$ alkyl ester; and (ii) at least one pharmaceutically acceptable carrier. In specific embodiments, the pharmaceutical composition releases about 80% or less; or 90% or less of the testosterone $C_2$-$C_{13}$ alkyl ester after 30 minutes in an aqueous medium. In some embodiments, the pharmaceutical composition releases about 50% or less of the testosterone $C_2$-$C_{13}$ alkyl ester after 1 hour in an aqueous medium. In certain embodiments, the pharmaceutical composition is administered with a meal. In some embodiments, the pharmaceutical composition is administered b.i.d. or q.d. In various embodiments, a method provided herein has a release or pharmacokinetic profile as described herein. In some embodiments, an oral testosterone undecanoate therapy described herein provides to a human a ratio of a testosterone equivalent dose from the testosterone $C_2$-$C_{13}$ alkyl ester to mean steady state testosterone $C_{max}$, the ratio being about 500×10$^6$ mL or less.

Also provided in some embodiments herein is an oral testosterone undecanoate therapy that provides to a human in need of androgen therapy by orally delivering to the human a composition comprising a therapeutically effective amount of testosterone undecanoate. In some embodiments, the therapy provides to the human a mean $C_{max}$ of testosterone that is less than about 15 ng/mL, or less than about 19 ng/mL after a single administration of the composition. In certain embodiments, the oral testosterone undecanoate therapy provides to the human a mean plasma $C_{max}$ of dihydrotestosterone that is about 3.6 ng/mL, or less; or about 4.5 ng/mL, or less after a single administration of the composition. In some embodiments, the oral testosterone undecanoate therapy provides to the human a testosterone mean plasma $C_{max}$ at steady state of about 1300 ng/dL or less after a single administration of the composition. In certain embodiments, the oral testosterone undecanoate therapy provides to the human a testosterone mean plasma $C_{min}$ at steady state of about 200 ng/dL or more after a single administration of the composition. In some embodiments, the oral testosterone undecanoate therapy provides to the human a ratio of a testosterone equivalent dose to a mean stead state testosterone $C_{max}$ of about 500×10$^6$ mL or less after a single administration of the composition. In certain embodiments, the oral testosterone undecanoate therapy provides to the human a difference between a mean plasma $C_{max}$ of testosterone at steady state and mean plasma $C_{min}$ of testosterone at steady state of about 11 ng/mL or less; or about 16 ng/mL or less. In some embodiments, the oral testosterone undecanoate therapy provides to the human a difference between a mean plasma $C_{max}$ at steady state and mean plasma $C_{min}$ at steady state of testosterone alkyl ester of about 200 ng/mL or less.

Provided in certain embodiments herein is a pharmaceutical composition comprising (i) a therapeutically effective amount of one or more testosterone alkyl ester; and (ii) a single (e.g., one and only one) lipid component solubilizing the testosterone alkyl ester. In some embodiments, provided herein is a pharmaceutical composition comprising a therapeutically effective amount of testosterone undecanoate; the pharmaceutical composition providing an increase in testosterone alkyl ester in plasma compared to an otherwise identical pharmaceutical composition comprising a testosterone alkyl ester other than testosterone undecanoate. In certain embodiments, provided herein is a pharmaceutical composition comprising (i) a therapeutically effective amount of one or more testosterone alkyl ester; and (ii) at least one pharmaceutically acceptable carrier; the pharmaceutical composition providing, when administered as a single dose to an individual, a dose of testosterone equivalent from the testosterone alkyl ester, to mean steady state $AUC_{0-\infty}$ ratio of about 500×10$^3$ mL/h or less.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention may be obtained by reference to the following detailed description that sets forth illustrative embodiments, in which the principles of the invention, in certain embodiment, are utilized, and the accompanying drawings of which:

FIG. 1 illustrates the release profiles of Capsules 1-4 subjected to USP Apparatus 2 at 37° C. and 100 rpm FIG. 2 illustrates the mean plasma testosterone concentrations following administration of several oral dosage forms described herein and an immediate release oral dosage.

FIG. 3 illustrates the mean plasma testosterone undecanoate concentrations following administration of several oral dosage forms described herein and an immediate release oral dosage.

FIG. 4 illustrates the mean plasma dihydrotestosterone concentrations following administration of several oral dosage forms described herein and an immediate release oral dosage.

DETAILED DESCRIPTION OF THE INVENTION

Provided herein are pharmaceutical compositions and methods of using the same. In some embodiments, the pharmaceutical compositions are formulated for oral delivery as an oral dosage form. In certain embodiments, a pharmaceutical composition described herein comprises a steroidal compound and at least one pharmaceutically acceptable carrier. In some embodiments, a pharmaceutical composition described herein is an oral dosage form comprising a steroidal compound and at least one pharmaceutically acceptable carrier. In specific embodiments, the steroidal compound is a steroidal androgen (e.g., testosterone, dihydrotestosterone, analogs, or prodrugs thereof). In certain embodiments, analogs or prodrugs of testosterone include, e.g., esters of testosterone. In specific embodiments, the esters of testosterone include, e.g., alkyl (e.g., straight chain, branched, cyclic, unsaturated, partially saturated, fully saturated and the like) esters of testosterone. Specifically, alkyl esters of testosterone include, by way of non-limiting example, lower alkyl esters (e.g., testosterone $C_2$-$C_{13}$ alkyl esters such as testosterone propionate, testosterone enthanate, or testosterone undecanoate), or higher alkyl esters (e.g., testosterone $C_{14+}$ alkyl esters such as testosterone palmitate). In further embodiments, the alkyl esters of testosterone include, by way of non-limiting example, cycloalkylalkyl esters (e.g., testosterone cypionate), cycloalkyl esters, and alkylcycloalkyl esters. In more specific embodiment, the testosterone alkyl ester is testosterone undecanoate. In certain embodiments, alkyl groups of the alkyl esters and/or other positions of the steroidal compound (e.g., testosterone alkyl ester, such as testosterone undecanoate) described herein are optionally substituted, e.g., with one or more halogen, hydroxy group, amino group, or the like, or combinations thereof.

In various embodiments, the pharmaceutical compositions are formulated for androgen (e.g., testosterone) therapy. In certain instances, the androgen therapy is an androgen (e.g., testosterone) replacement therapy. In some embodiments, the androgen replacement therapy is utilized to treat individuals suffering from androgen deficiency (e.g., postmenopausal women, menopausal women, sexually dysfunctional women, andropausal men, hypogonadal men, and the like) or treat individuals in need of increased androgen levels. In some embodiments, the androgen (e.g., testosterone) replacement therapy is utilized for the treatment of individuals diagnosed with or exhibiting symptoms of androgen (e.g., testosterone) deficiency including, e.g., in aging men.

Provided in certain embodiments herein are pharmaceutical compositions that provide a plasma $C_{max}$ of testosterone that is less than 1500 ng/dL in at least 85% of a population of individuals (following administration of a single dose and/or in the steady state) when administered to a population of individuals (e.g., adult and/or pubescent human males). In some embodiments a pharmaceutical composition described herein provides a plasma $C_{max}$ of testosterone that is less than 1800 ng/dL in at least 95% of a population of individuals (following administration of a single dose and/or in the steady state) when administered to a population of individuals (e.g., adult and/or pubescent human males). In some embodiments the oral dosage forms provide a plasma $C_{max}$ of testosterone that is less than 2500 ng/dL in all individuals (following administration of a single dose and/or in the steady state) when administered to a population of individuals (e.g., adult and/or pubescent human males). In some embodiments, the individuals are adult humans. In specific embodiments, the adult humans are adult hypogonadal or otherwise androdeficient male humans.

In certain instances, normal human male testes produce four to eight milligrams of testosterone daily and human females produce less. Within certain contexts of the invention described herein, it will be generally recognized by those of skill in the art that the physiological "normal" range of total testosterone in men is about 250 to about 1,100 nanograms per deciliter (ng/dL) and in healthy women is about 11 ng/dL to about 78 ng/dL. Journal of Clinical Endocrinology & Metabolism, 85(7):2395-401.

Provided in some embodiments herein are pharmaceutical compositions that provide a $C_{min}$ that is about 10 ng/dL or greater and a $C_{max}$ that is about 100 ng/dL or less in at least 50%, at least 60%, at least 70%, at least 80%, at least 90%, at least 95% of adult female humans (e.g., postmenopausal or otherwise androdeficient female humans) when administered to a population of adult female humans (following administration of a single dose and/or in the steady state). Provided in some embodiments herein are pharmaceutical compositions that provide a $C_{min}$ that is about 12 ng/dL or greater and a $C_{max}$ that is about 82 ng/dL or less in at least 50%, at least 60%, at least 70%, at least 80%, at least 90%, at least 95% of adult female humans (e.g., postmenopausal or otherwise androdeficient female humans) when administered to a population of adult female humans (following administration of a single dose and/or in the steady state).

In some enibodirnents, the pharmaceutical composition provided herein is a delayed release oral dosage form comprising a steroidal compound and at least one pharmaceutically acceptable carrier. In certain instances, the delayed release oral dosage forms release the active in an aqueous medium (e.g., water, gastric fluid, or an aqueous solution with a pH of about 5.8) at a rate slower than an immediate or fast release oral dosage form (e.g., as measured by the amount of active found in the aqueous medium). In some embodiments, delayed release oral dosage forms comprise a steroidal compound, at least one hydrophilic carrier. In further embodiments, delayed release oral dosage forms comprise a steroidal compound, at least one hydrophilic carrier, and at least one lipidic and/or lipophilic carrier. In still further embodiments, the delayed release oral dosage form comprises at least one steroidal compound, at least one hydrophilic carrier, at least one lipidic and/or lipophilic carrier, and at least one viscosity enhancer or solidifying agent. In still further embodiments, the delayed release oral dosage form comprises at least one steroidal compound and at least one viscosity enhancer or solidifying agent. In some embodiments, a pharmaceutical composition provided herein is formulated, e.g., with the viscosity enhancing agent or solidifying agent, to provide a solid, a semi-solid, a gel, a jelly, a paste, or the like. In specific embodiments, the delayed release oral dosage form is a capsule (e.g., a hard- or soft-gel capsule, a tablet or other solid dosage form). In some embodiments, the delayed release dosage form provided herein comprises the active (e.g., one or more testosterone alkyl ester such as testosterone undecanoate) in different release fractions (e.g., an immediate release portion and a delayed release portion). In specific embodiments, pharmaceutical compositions or dosage forms provided herein comprise one or more of an immediate release portions or fractions, fast release portions or fractions, or combinations thereof and an enteric-release portion or fraction, sustained-release portion or fraction, controlled-release portion or fraction, extended-release portion or fraction, pulsatile-release portion or fraction, timed-release portion or fraction, or combinations thereof.

Pharmaceutical Compositions

In certain embodiments, provided herein is a pharmaceutical composition comprising at least one steroidal compound (e.g., testosterone, dihydrotestosterone, estradiol, or analogs or prodrugs thereof) and at least one pharmaceutically acceptable carrier. In specific embodiments, the steroidal compound is a steroidal androgen (e.g., testosterone, dihydrotestosterone, or prodrugs thereof). In some embodiments, the steroidal compound is an alkylated, hydroxy-alkylated and/or hydroxy-alkoylated natural steroid (e.g., testosterone alkyl ester, dihydrotestosterone alkyl ester, estradiol alkyl ester, or the like). In certain embodiments, analogs or prodrugs of testosterone include, e.g., esters of testosterone. In specific embodiments, the esters of testosterone include, e.g., alkyl (e.g., straight chain, branched, cyclic, unsaturated, partially saturated, fully saturated and the like) esters of testosterone. Specifically, alkyl esters of testosterone include, by way of non-limiting example, lower alkyl esters (e.g., testosterone $C_2$-$C_{13}$ alkyl esters such as testosterone propionate, testosterone enthanate, or testosterone undecanoate), or higher alkyl esters (e.g., testosterone $C_{14+}$ alkyl esters such as testosterone palmitate). In further embodiments, the alkyl esters of testosterone include, by way of non-limiting example, cycloalkylalkyl esters (e.g., testosterone cypionate), cycloalkyl esters, and alkylcycloalkyl esters. In more specific embodiments, the testosterone alkyl ester is testosterone undecanoate. In some embodiments, the at least one steroidal compound comprises (1) a testosterone lower alkyl ester (e.g., testosterone propionate, testosterone enthanate, or testosterone undecanoate); and (2) a testosterone higher alkyl ester (e.g., testosterone palmitate). Generally, as used herein, a pharmaceutical composition comprising a steroidal compound includes the disclosure of a pharmaceutical composition comprising one or more steroidal compounds.

In certain embodiments, any pharmaceutical composition described herein comprises a therapeutically effective amount of at least one steroidal compound (e.g., a testosterone alkyl ester, such as testosterone undecanoate). In some embodiments, a therapeutically effective amount of a steroidal compound (e.g., a testosterone alkyl ester, such as testosterone undecanoate) is divided into one or more oral dosage form. In some embodiments, the one or more of the oral dosage forms described herein collectively comprise a therapeutically effective amount of a testosterone alkyl ester (e.g., testosterone undecanoate). Thus, in some embodiments, the therapeutically effective amount of a steroidal compound (e.g., a testosterone alkyl ester, such as testosterone undecanoate) within a pharmaceutical composition described herein may vary when the pharmaceutical composition is administered in combination with another therapy. Furthermore, therapeutically effective amounts of a formulation may depend on the specific formulation within which the at least one steroidal compound is found. For example, in some embodiments, more than one steroidal compound is present in a pharmaceutical composition described herein. Thus, when there is a combination of steroidal compounds, in certain instances one or both of the steroidal compounds present has a therapeutically effective amount that is lower than is required when the steroidal compounds are administered separately or alone. In some embodiments, a pharmaceutical composition described herein further comprises an adjuvant, which, in certain instances, allows for a lower amount of a steroidal compound to be utilized as a therapeutically effective amount.

In certain embodiments, a pharmaceutical composition described herein comprises about 1 mg to about 1.5 g, about 10 mg to about 1000 mg, or about 10 mg to about 200 mg of a steroidal compound (e.g., a testosterone alkyl ester, such as testosterone undecanoate). In specific embodiments, a pharmaceutical composition described herein comprises about 10 mg to about 50 mg, about 15 mg to about 40 mg, about 20 mg, to about 30 mg, or about 25 mg of steroidal compound (e.g., a testosterone alkyl ester, such as testosterone undecanoate). In other embodiments, a pharmaceutical composition described herein comprises about 70 mg to about 150 mg, about 80 mg to about 140 mg, about 90 mg to about 140 mg, about 100 mg to about 130 mg, about 110 mg to about 130 mg, or about 120 mg of a steroidal compound (e.g., a testosterone alkyl ester, such as testosterone undecanoate). In some embodiments, a pharmaceutical composition described herein comprises about 0.1 mg to about 5 mg of a steroidal compound (e.g., a testosterone alkyl ester such as testosterone undecanoate) per kg of an individual to whom the oral dosage form is to be administered. In certain embodiments, a pharmaceutical composition described herein comprises an amount of a steroidal compound (e.g., a testosterone alkyl ester, such as testosterone undecanoate) sufficient to provide about 1 mg to about 1 g, about 5 mg to about 500 mg, about 10 mg to about 300 mg, or about 20 to about 250 mg of a steroidal compound (e.g., a testosterone alkyl ester, such as testosterone undecanoate) to an individual upon once a day, twice a day, three times a day, or four times a day oral administration.

In some embodiments, the at least one pharmaceutically acceptable carrier is any carrier suitable for delivering an efficacious amount of a steroidal compound, e.g., a testosterone alkyl ester, to an individual. In some embodiments, the at least one pharmaceutically acceptable carrier is or comprises a hydrophilic carrier (e.g., a hydrophilic surfactant or hydrophilic additive). In certain embodiments, the at least one pharmaceutically acceptable carrier is a lipophilic carrier (e.g., a lipophilic surfactant or lipophilic additive). In some embodiments, the at least one pharmaceutically acceptable carrier is a hydrophilic carrier (e.g., a hydrophilic surfactant or hydrophilic additive) and a lipophilic carrier (e.g., a lipophilic surfactant or lipophilic additive). In certain embodiments, the hydrophilic carrier is a hydrophilic triglyceride. In specific embodiments, the hydrophilic triglyceride is a polyoxylated castor oil, or a polyoxylated hydrogenated castor oil. In some embodiments, any pharmaceutical composition provided herein consists essentially of a lipophilic carrier or combination of lipophilic carriers. In certain embodiments, any pharmaceutical composition provided herein comprises a lipophilic carrier and less than 10% w/w, less than 5% w/w or is substantially free of a hydrophilic carrier. In certain embodiments, any pharmaceutical composition provided herein comprises a lipophilic carrier and less than 10% w/w, less than 5% w/w or is substantially free of a hydrophilic carrier. In some embodiments, the pharmaceutical composition comprising a carrier (e.g., a hydrophilic carrier and/or a lipophilic carrier), the pharmaceutical composition is a solid, a semi-solid, a gel, a jelly, a paste, or the like. In certain embodiments, e.g., wherein a pharmaceutical composition comprising a hydrophilic carrier and/or a lipophilic carrier, a viscosity enhancing agent or a solidifying agent is utilized to afford a pharmaceutical composition that is a solid, a semi-solid, a gel, a jelly, a paste, or the like. Thus, in certain embodiments, the at least one pharmaceutically acceptable carrier is a hydrophilic carrier (e.g., a hydrophilic surfactant or hydrophilic additive) and a viscosity enhancing or solidifying agent. In certain embodiments, the at least one pharmaceutically acceptable carrier is a lipophilic carrier (e.g., a lipophilic surfactant or lipophilic additive) and a viscosity enhancing or solidifying agent. In some embodiments, the at least one pharmaceutically acceptable carrier is or comprises a hydrophilic carrier (e.g., a hydrophilic surfactant or hydrophilic additive), a lipophilic carrier (e.g., a lipophilic surfactant or lipophilic additive), and a viscosity enhancing or solidifying agent. In some embodiments, the at least one pharmaceutically acceptable carrier is or comprises an amphiphilic or zwitterionic carrier (e.g., a ampiphilic surfactant or ampiphilic additive). In certain embodiments, the pharmaceutically acceptable carrier is any carrier suitable for achieving one or more of the pharmacokinetic and/or pharmacodynamic profiles set forth herein.

Additives useful herein include chemical substances that are generally pharmacologically inactive. Further, the additive may be solid, liquid or semi-solid in nature at about ambient room temperature. Furthermore, the additive may be hydrophilic or lipophilic. In certain instances, a "hydrophilic additive" is a substance that has at least one polar side group in its chemical structure which will attract water; whereas a "lipophilic additive" exhibits a tendency to repel water.

In some embodiments, the hydrophilic or lipophilic additive is contained within the components forming a composition and/or pharmaceutical dosage form thereof. In certain embodiments, the hydrophilic or lipophilic additive is in an encapsulation coat in compositions. Alternatively, the additives can be comprised in the pharmaceutical composition but not as part of the composition itself. Specific, non-limiting examples of additives are described below.

Suitable additives include any additive that can facilitate the processes involving the preparation of a pharmaceutical composition and/or dosage form described herein. In some instances, such additives include those commonly utilized to facilitate the processes involving the preparation of a composition and/or a pharmaceutical dosage form described herein. These processes include agglomeration, air suspension chilling, air suspension drying, balling, coacervation, comminution, compression, pelletization, cryopelletization, encapsulation, extrusion, granulation, homogenization, inclusion complexation, lyophilization, nanoencapsulation, melting, mixing, molding, pan coating, solvent dehydration, sonication, spheronization, spray chilling, spray congealing, spray drying, or other processes known in the art. In certain instances, the additive is optionally pre-coated or encapsulated. Suitable additives are optionally utilized to influence the drug release from the composition and/or pharmaceutical dosage form.

Suitable additives utilized in various embodiments described herein include, by way of non-limiting example, adsorbing agents, anti-adherents, anticoagulants, antifoaming agents, antioxidants, anti-caking agents, anti-static agents, binders, bile acids, bufferants, bulking agents, chelating agents, coagulants, colorants, co-solvent, opaquants, congealing agents, coolants, cryoprotectants, diluents, dehumidifying agents, desiccants, desensitizers, disintegrants, dispersing agents, enzyme inhibitors, glidants, fillers, hydrating agent, super disintegrants, gums, mucilages, hydrogen bonding agents, enzymes, flavorants, humectants, humidifying agents, lubricant oils, ion-exchange resins, lubricants, plasticizers, pH modifying agents, preservatives, solidifying agent, solvents, solubilizers, spreading agent sweeteners, stabilizers, surface area enhancing agents, suspending agent, thickeners, viscosity increasing agents, waxes and mixtures thereof.

Some non-limiting examples of the hydrophilic or lipophilic additives suitable for the current invention are as follows:

Alcohols and/or Polyols (e.g. ethanol, isopropanol, butanol, benzyl alcohol, ethylene glycol, propylene glycol, glycerol, sorbitol, mannitol, dimethyl isosorbide, polyethylene glycol, fatty acid alcohol, vinyl alcohol polypropylene glycol, polyvinylalcohol, tocopherols, cellulose cyclodextrins, other derivatives, forms, mixtures thereof, or the like); ethers of polyethylene glycols having an average molecular weight of about 200 to about 20,000 (e.g. tetrahydrofurfuryl alcohol PEG ether, methoxy PEG, or the like); Amides (e.g. 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide, polyvinylpyrrolidone and the like.); Esters (e.g. ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other additives known in the art, such as dimethyl acetamide, dimethyl isosorbide, N-methyl pyrrolidones, monooctanoin, diethylene glycol monoethyl ether, or the like); Amino acids (e.g. P-aminobenzamidine, sodium glycocholate) mesylate; Amino acids and modified amino acids (e.g. aminoboronic acid derivatives and n-acetylcysteine; Peptides and modified peptides (e.g. bacitracin, phosphinic acid dipeptide derivatives, pepstatin, antipain, leupeptin, chymostatin, elastin, bestatin, phoshporamindon, puromycin, cytochalasin potatocarboxy peptidase inhibitor, amastatin, or the like); Polypeptide protease inhibitors; Mucoadhesive polymers (e.g. polyacrylate derivatives, chitosan, cellulosics, chitosan-EDTA, chitosan-EDTA-antipain, polyacrylic acid, carboxymethyl cellulose etc.); or the like; or combinations thereof.

Some more examples of suitable additives for compositions and/or dosage forms described herein include, by way of non-limiting example, talc, magnesium stearate, silica (e.g. fumed silica, micronized silica, magnesium aluminum silicate etc.) and/or derivatives, polyethylene glycols, surfactants, waxes, oils, cetyl alcohol, polyvinyl alcohol, stearic acid, stearic acid salts, stearic acid derivatives, starch, hydrogenated vegetable oils, hydrogenated castor oils, sodium benzoate, sodium acetate, leucine, PEG, alkyl sulfate salts; acetylated monoglycerides; long-chain alcohols; silicone derivatives; butylated hydroxy toluene (BHT), butylated hydroxyl anisole (BHA), gallic acid, propyl gallate, ascorbic acid, ascorbyl palmitate, 4-hydroxymethyl-2,6-ditert-butyl phenol, dry starch, dry sugars, polyvinyl pyrrolidones, starch paste, methacrylic copolymers, bentonite, sucrose, polymericcellulose derivatives, shellac, sugar syrup; corn syrup; polysaccharides, acacia, tragacanth, guar gum, xanthan gums; alginates; gelatin; gelatin hydrolysate; agar; sucrose; dextrose; PEG, vinyl pyrrolidone copolymers, poloxamers; pregelatinized starch, sorbitol, glucose); acetic acid, hydrochloric acid, hydrobromic acid, hydriodic acid, sulfuric acid, nitric acid, boric acid, phosphoric acid, acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid, vinegar, pharmaceutically acceptable bases, such as an amino acid, an amino acid ester, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide, diisopropylethylamine, ethanolamine, ethylenediamine, triethanolamine, triethylamine, triisopropanolamin; salt of a pharmaceutically acceptable cation and an anion; EDTA and EDTA salts; titanium dioxide, food dyes, lakes, natural vegetable colorants, iron oxides, silicates, sulfates, magnesium hydroxide and aluminum hydroxide; halogenated hydrocarbons, trichloroethane, trichloroethylene, dichloromethane, fluorotrichloromethane, diethylether, trehelose, phosphates, citric acid, tartaric acid, gelatin, dextran and mannitol, lactose, mannitol, sodium chloride, potassium chloride, spray-dried lactose, hydrolyzed starches, directly compressible starch, microcrystalline cellulose, cellulosic derivatives, sorbitol, sucrose, sucrose-based materials, calcium sulfate, dibasic calcium phosphate, dextrose, croscarmellose sodium, starch, starch derivatives, clays, gums, cellulose, cellulose derivates, alginates, crosslinked polyvinylpyrrolidone, sodium starch glycolate and microcrystalline cellulose, magnesium oxide, magnesium carbonates; desensitizers, spray-dried flavors, essential oils, ethyl vanillin, styrene/divinyl benzene copolymers, quaternary ammonium compounds, polyethylene glycol, citrate esters (such as triethyl citrate, acetyl triethyl citrate, acetyltributyl citrate), acetylated monoglycerides, glycerin, triacetin, propylene glycol, phthalate esters (e.g., diethyl phthalate, dibutyl phthalate), castor oil, sorbitol and dibutyl sebacate, ascorbic acid, boric acid, sorbic acid, benzoic acid, and salts thereof, parabens, phenols, benzyl alcohol, and quaternary ammonium compounds; alcohols, ketones, esters, chlorinated hydrocarbons water; sweeteners, (e.g. maltose, sucrose, glucose, sorbitol, glycerin and dextrins, aspartame, saccharine, saccharine salts, glycyrrhizin), viscosity modifiers, sugars, polyvinylpyrrolidone, cellulosics, polymers, gums and/or alginates.

Additives can also be materials such as proteins (e.g., collagen, gelatin, Zein, gluten, mussel protein, lipoprotein); carbohydrates (e.g., alginates, carrageenan, cellulose derivatives, pectin, starch, chitosan); gums (e.g., xanthan gum, gum arabic); spermaceti; natural or synthetic waxes; carnuaba wax; fatty acids (e.g., stearic acid, hydroxystearic acid); fatty alcohols; sugars; shellacs, such as those based on sugars (e.g., lactose, sucrose, dextrose) or starches; polysaccharide-based shellacs (e.g., maltodextrin and maltodextrin derivatives, dextrates, cyclodextrin and cyclodextrin derivatives); cellulosic-based polymers (e.g., ethyl cellulose, methyl cellulose, microcrystalline cellulose, sodium carboxymethyl cellulose, hydroxypropylmethyl cellulose, ethyl cellulose, hydroxypropyl cellulose, HPMC acid succinates, cellulose acetate, cellulose nitrate, cellulose acetate butyrate, cellulose acetate trimellitate, carboxymethylethyl cellulose, hydroxypropylmethyl cellulose phthalate), shellacs; inorganics, such as dicalcium phosphate, hydroxyapitite, tricalcium phosphate, talc and titania; polyols, such as mannitol, xylitol and sorbitol; polyethylene glycol esters; and polymers, such as alginates, poly(lactide coglycolide), gelatin, crosslinked gelatin, and agar-agar.

It should be appreciated that there is considerable overlap between the above-listed additives in common usage, since a given hydrophilic or lipophilic additive is often classified differently by different practitioners in the field, or is commonly used for any of several different or overlapping functions. Thus, the above-listed hydrophilic or lipophilic additives should be taken as merely exemplary, and not limiting, of the types of additives that can be included in compositions of the present invention. In certain embodiments, the amounts of such additives are optionally adjusted and/or determined by one skilled in the art, according to the particular properties desired.

In certain embodiments, the at least one pharmaceutically acceptable carrier comprises at least one hydrophilic carrier (e.g., hydrophilic surfactant). In some embodiments, the hydrophilic carrier is a polyoxylated glyceride (e.g., mono-, di-, or tri-glyceride), a polyoxylated vegetable oil, a polyoxylated hydrogenated vegetable oil, a polyoxylated fatty acid (mono-, or di-substituted), combinations thereof, or the like. In certain embodiments, the at least one pharmaceutically acceptable carrier comprises or further comprises a lipophilic carrier. Lipophilic carriers are selected from, by way of non-limiting example, a lipophilic surfactant, a vegetable oil (e.g., castor oil), a fatty acid, a fatty alcohol, a glyceride (e.g., mono-, di-, or tri-glyceride), a hydrogenated vegetable oil, a Vitamin E compound (e.g., d,1-α-tocopherol), a triglyceride, a fatty acid, polyoxylated fatty acid, polyoxylated triglyceride, polyoxylated vegetable oil, or combinations thereof. In some embodiments, polyoxylated compounds include polyethoxylated compounds.

In certain embodiments, the at least one hydrophilic carriers make up about 1% to about 99% w/w, about 2% to about 80% w/w, about 2% to about 50% w/w, or about 10% to about 40% w/w of any pharmaceutical composition described herein. In some embodiments, lipophilic carriers make up about 1% w/w to about 99% w/w, about 2% to about 80% w/w, about 10% w/w to about 80% w/w, about 30% w/w, to about 80% w/w, or about 40% to about 80% w/w of any phanmaceutical composition described herein.

In specific embodiments, provided herein is a pharmaceutical composition (e.g., a delayed release dosage form) comprising a hydrophilic carrier. In more specific embodiments, the hydrophilic carrier is or comprises a polyoxylated vegetable oil (e.g., a polyoxylated, hydrogenated vegetable oil). In still more specific embodiments, a polyoxylated vegetable oil is a polyoxylated castor oil (e.g., a polyoxylated, hydrogenated castor oil). In certain embodiments, the lipidic and/or lipophilic carrier is not a $C_6$-$C_{18}$ fatty acid. In some embodiments, the lipophilic carrier is a $C_{20+}$ fatty acid. In some embodiments, the lipidic and/or lipophilic carrier is not a fatty acid or an unmodified (e.g., non-polyoxylated) vegetable oil. In more specific embodiments, the lipidic and/or lipophilic carrier is not oleic acid or castor oil. In certain specific embodiments provided herein is a pharmaceutical composition (e.g., a delayed release dosage form) comprising an ampiphilic carrier. In more specific embodiments, the ampiphilic carrier is or comprises a zwitterionic choline (e.g., phosphatidylcholine). In some specific embodiments, provided herein is a pharmaceutical composition (e.g., a delayed release dosage form) comprising a lipophilic carrier. In more specific embodiments, the lipophilic carrier is or comprises, by way of non-limiting example, a mono-, di- or triglyceride (e.g., glycerol monolinoleate).

In some embodiments, the at least one pharmaceutically acceptable carrier comprises at least one hydrophilic carrier, and at least one lipidic and/or lipophilic carrier. In further embodiments, the at least one pharmaceutically acceptable carrier comprises at least one hydrophilic carrier, at least one lipidic and/or lipophilic carrier, and at least one viscosity enhancer or solidifying agent. In some embodiments, the solidifying agent is a polyethylene glycol (e.g., a high molecular weight polyethylene glycol, such as PEG 8000). In specific embodiments, a pharmaceutical composition described herein comprises, along with a steroidal agent (e.g., a testosterone alkyl ester), a hydrogenated and polyoxylated castor oil and a polyethylene glycol. In more specific embodiments, the pharmaceutical composition comprising a hydrogenated and polyoxylated castor oil and a polyethylene glycol further comprises an additional lipidic and/or lipophilic carrier. In some embodiments, the additional lipidic and/or lipophilic carrier is a monoglyceride, a diglyceride, a Vitamin E compound, or a combination thereof.

In certain embodiments, pharmaceutical compositions described herein include oral dosage forms or delayed release oral dosage forms of any of Tables A to Q. In Tables A to Q, approximate weight percentages of the compositions formulated into the capsules are provided. In specific embodiments, the steroidal compound of any of Capsules A1 to Q2 comprises an alkyl ester testosterone (e.g., testosterone undecanoate). In certain instances, provided in the tables are non-limiting grades and/or sources of components utilized. Disclosure provided in Tables A to Q is not limited to the grades and/or sources described.

TABLE A

| Component | Capsule A1 % w/w | Capsule A2 % w/w |
| --- | --- | --- |
| Steroidal Compound (~10-1000 mg) | 1-50 | 10-30 |
| Hydrophilic Carrier | 1-90 | 10-30 |
| Lipophilic Carrier | 1-90 | 40-70 |
| Solidifying Agent (additive) | 1-20 | 5-10 |

TABLE B

| Component | Capsule B1 % w/w | Capsule B2 % w/w |
| --- | --- | --- |
| Testosterone undecanoate (~10-1000 mg) | 1-50 | 15 |
| Polyoxyl 40 Hydrogenated Castor Oil, NF | 1-50 | 16 |
| Glycerol Monolinoleate, NF (Maisine 35-1) | 30-90 | 63 |
| Polyethylene Glycol 8000, USP | 1-20 | 6 |

TABLE C

| Component | Capsule C1 % w/w | Capsule C2 |
| --- | --- | --- |
| Testosterone undecanoate (~10-1000 mg) | 1-50 | 25 |
| Polyoxyl 35 Castor Oil, NF | 1-50 | 21 |
| Vitamin E, USP (d,1-α-tocopherol) | 30-90 | 48 |
| Polyethylene Glycol 8000, USP | 1-20 | 6 |

TABLE D

| Component | Capsule D1 % w/w | Capsule D2 % w/w |
| --- | --- | --- |
| Steroidal Compound (~10-1000 mg) | 15 | 10-30 |
| Lauryl macrogol glyceride (Gelucire 44/14) | 51 | 20-90 |
| Stearoyl macrogol glyceride (Gelucire 50/13) | 34 | 10-90 |

TABLE E

| Component | Capsule E1 % w/w | Capsule E2 % w/w |
| --- | --- | --- |
| Steroidal Compound (~10-1000 mg) | 20 | 10-30 |
| C8-C18 macrogol glyceride (Gelucire 43/01) | 35 | 10-70 |
| Polyglyceryl-3-oleate (Caprol 3GO) | 45 | 5-60 |

TABLE F

| Component | Capsule F1 % w/w | Capsule F2 % w/w |
| --- | --- | --- |
| Steroidal Compound (~10-1000 mg) | 15 | 10-25 |
| Lauryl macrogol glyceride (Gelucire 44/14) | 40 | 5-80 |
| Vitamin E | 30 | 2-60 |
| Hypromellose (Methocel K100 M LV, CR) | 15 | 5-25 |

TABLE G

| Component | Capsule G1 % w/w | Capsule G2 % w/w |
| --- | --- | --- |
| Steroidal Compound (~10-1000 mg) | 15 | 10-30 |
| PEG-40 hydrogenated Castor Oil (Cremophor ® RH40) | 60 | 5-80 |
| Polyethylene glycol 8000 | 15 | 5-40 |
| Hypromellose (Methocel K100 M LV, CR) | 10 | 5-25 |

TABLE H

| Component | Capsule H1 % w/w | Capsule H2 % w/w |
| --- | --- | --- |
| Steroidal Compound (~10-1000 mg) | 15 | 10-30 |
| Corn Glycerides (Maisine 35-1) | 60 | 5-90 |
| Polyethylene glycol 8000 | 20 | 5-70 |

TABLE I

| Component | Capsule I1 % w/w | Capsule I2 % w/w |
| --- | --- | --- |
| Steroidal Compound (~10-1000 mg) | 25 | 10-30 |
| PEG-40 hydrogenated Castor Oil (Cremophor ® RH40) | 15 | 5-80 |
| Vitamin E | 20 | 2-60 |
| Corn Glycerides (Maisine 35-1) | 30 | 5-50 |
| Polyethylene Glycol 8000 | 10 | 5-20 |

TABLE J

| Component | Capsule J1 % w/w | Capsule J2 % w/w |
| --- | --- | --- |
| Steroidal Compound (~10-1000 mg) | 15 | 10-30 |
| Hydrogenated vegetable oil | 50 | 2-80 |
| Polyethylene glycol 8000 | 35 | 2-80 |

TABLE K

| Component | Capsule K1 % w/w | Capsule K2 % w/w |
| --- | --- | --- |
| Steroidal Compound (~10-1000 mg) | 50 | 30-60 |
| Corn Glycerides (Maisine 35-1) | 50 | 30-60 |

TABLE L

| Component | Capsule L1 % w/w | Capsule L2 % w/w |
|---|---|---|
| Steroidal Compound (~10-1000 mg) | 40 | 30-60 |
| Fish Oil | 50 | 30-60 |
| Vitamin E | 10 | 3-15 |

TABLE M

| Component | Capsule M1 % w/w | Capsule M2 % w/w |
|---|---|---|
| Steroidal Compound (~10-1000 mg) | 40 | 30-60 |
| Omega-3-acid esters | 50 | 30-60 |
| Polyethylene glycol 8000 | 5 | 3-15 |

TABLE N

| Component | Capsule N1 % w/w | Capsule N2 % w/w |
|---|---|---|
| Testosterone undecanoate | 5-30 | 10-20 |
| Polyoxyl 40 Hydrogenated Castor Oil, NF | 5-30 | 10-20 |
| Glyceryl Monolinoleate, NF (Maisine 35-1) | 50-90 | 55-70 |
| Polyethylene Glycol 8000, USP | 1-15 | 3-8 |

TABLE O

| Component | Capsule O1 % w/w | Capsule O2 % w/w |
|---|---|---|
| Testosterone undecanoate | 10-40 | 20-30 |
| Polyoxyl 35 Castor Oil, NF | 10-30 | 15-25 |
| Vitamin E, USP (d,1-α-tocopherol) | 30-70 | 40-55 |
| Polyethylene Glycol 8000, USP | 1-15 | 3-8 |

TABLE P

| Component | Capsule P1 % w/w | Capsule P2 % w/w |
|---|---|---|
| Testosterone undecanoate | 10-40 | 20-25 |
| Vitamin E Polyethylene Glycol Succinate, NF | 10-40 | 20-25 |
| Vitamin E, USP (d,1-tocopherol) | 15-60 | 30-40 |
| Polyethylene Glycol 8000, USP | 1-10 | 2-6 |
| Hypromellose (100 cP, K100 Premium LV) | 5-40 | 15-25 |

TABLE Q

| Component | Capsule Q1 % w/w | Capsule Q2 % w/w |
|---|---|---|
| Testosterone undecanoate | 10-40 | 20-25 |
| Vitamin E Polyethylene Glycol Succinate, NF | 10-40 | 20-25 |
| Vitamin E, USP (d,1-tocopherol) | 15-60 | 30-40 |
| Polyethylene Glycol 8000, USP | 1-10 | 2-6 |
| Hypromellose (4,000 cP, K4M) | 5-40 | 15-25 |

In certain embodiments, any pharmaceutical composition described herein, e.g., a pharmaceutical composition of any of Tables A to Q can be prepared by (i) combining and heating all ingredients until a molten mixture is obtained (e.g., 50-70° C.); and (ii) encapsulating an amount of molten mixture comprising a select dose (e.g., a therapeutically effective amount or a partial dose of a therapeutically effective amount) of steroidal compound to obtain an oral dosage form. In certain instances, the molten mixture is spray-congealed to obtain beads. In some instances, the molten mixture is sprayed onto inert cores (e.g., sugar spheres) to obtain coated cores. In certain embodiments, such beads, cores, or similar forms are encapsulated or otherwise formulated to provide an oral dosage form. In some instances, the molten mixture is admixed, uniformly dispersed, or granulated over a carrier and compressed into a tablet dosage form. In certain embodiments, prior to compression, the molten mixture/carrier composition is further mixed with one or more pharmaceutical aid including, by way of non-limiting example, glidants, lubricants, binders, or the like. In some embodiments, the carrier is a therapeutically inert carrier such as, by way of non-limiting example, microcrystalline cellulose, starch, lactose, or the like.

In some embodiments, compositions described herein (e.g., compositions set forth in Tables K to M), are optionally filled into a delayed release capsule or shell, or are otherwise coated or encapsulated with a delayed release coat.

Pharmacokinetics and Pharmacodynamics

Provided in certain embodiments herein are androgen therapies (e.g., testosterone undecanoate therapies), pharmaceutical compositions and oral dosage forms that provide a plasma $C_{max}$ of testosterone that is less than 1500 ng/dL in at least 85% of a population of individuals (following administration of a single dose and/or in the steady state) when administered to a population of individuals. In some embodiments the androgen therapies (e.g., testosterone undecanoate therapies), pharmaceutical compositions or oral dosage forms provide a plasma $C_{max}$ of testosterone that is less than 1800 ng/dL in at least 95% of a population of individuals (following administration of a single dose and/or in the steady state) when administered to a population of individuals (e.g., adult and/or pubescent human males). In some embodiments the androgen therapies (e.g., testosterone undecanoate therapies), pharmaceutical compositions or oral dosage forms provide a plasma $C_{max}$ of testosterone that is less than 2500 ng/dL in all or substantially all individuals (following administration of a single dose and/or in the steady state) when administered to a population of individuals (e.g., adult and/or pubescent human males). In some embodiments, the androgen therapies (e.g., testosterone undecanoate therapies), pharmaceutical compositions and oral dosage forms provides a plasma $C_{max}$ of testosterone that is less than 1500 ng/dL in at least 85% and less than 1800 ng/dL in at least 95% of a population of individuals (following administration of a single dose and/or in the steady state) when administered to a population of individuals (e.g., adult and/or pubescent human males). In certain embodiments, the androgen therapies (e.g., testosterone undecanoate therapies), pharmaceutical compositions and oral dosage forms provides a plasma $C_{max}$ of testosterone that is less than 1500 ng/dL in at least 85%, less than 1800 ng/dL in at least 95%, and less than 2500 ng/dL in at least 99% of a population of individuals (following administration of a single dose and/or in the steady state) when administered to a population of individuals (e.g., adult and/or pubescent human males). In some embodiments, the androgen therapies (e.g., testosterone undecanoate therapies), pharmaceutical compositions and oral dosage forms provides a plasma $C_{max}$ of testosterone that is less than 1500 ng/dL in at least 85%, and less than 2500 ng/dL in at least 99% of a population of individuals (following administration of a single dose and/or in the steady state) when administered to a population of individuals (e.g., adult and/or pubescent human males). In some embodiments, the androgen therapies (e.g., testosterone undecanoate therapies), pharmaceutical compositions and oral dosage forms provides a plasma $C_{max}$ of testosterone that is less than 1800 ng/dL in at least 95%, and less than 2500 ng/dL in at least 99% of a population of individuals (following administration of a single dose and/or in the steady state) when administered to a population of individuals (e.g., adult and/or pubescent human males). In some embodiments, as used in any description herein, individuals are adult humans. In specific embodiments, the adult humans are adult male humans. In certain embodiments, the individuals are adult hypogonadal adult male humans. Plasma concentrations described herein are optionally obtained by administering a composition described herein to human males, e.g., hypogonadal human males. In other instances, plasma concentration are optionally obtained by administering the composition to testosterone deficient human subjects (e.g., postmenopausal women) who provide a population representative of the effects of testosterone therapy on individuals with low levels of testosterone. Clin. Endocrinology 2007, 66(4):570-85.

Provided in some embodiments herein are pharmaceutical compositions that provide a $C_{min}$ that is about 10 ng/dL or greater and a $C_{max}$ that is about 100 ng/dL or less in at least 50%, at least 60%, at least 70%, at least 80%, at least 90%, at least 95% of adult female humans (e.g., postmenopausal or otherwise androdeficient female humans) when administered to a population of adult female humans (following administration of a single dose and/or in the steady state). Provided in some embodiments herein are pharmaceutical compositions that provide a $C_{min}$ that is about 12 ng/dL or greater and a $C_{max}$ that is about 82 ng/dL or less in at least 50%, at least 60%, at least 70%, at least 80%, at least 90%, at least 95% of adult female humans (e.g., postnenopausal or otherwise androdeficient female humans) when administered to a population of adult female humans (following administration of a single dose and/or in the steady state). In some embodiments, the adult female humans are sexually dysfunctional adult female humans. In certain embodiments, the adult female humans are postmenopausal female humans.

Pharmaceutical compositions and oral dosage forms described herein are formulated, in various embodiments, to achieve the pharmacokinetic and pharmacodynamic profiles herein in any suitable manner. In certain instances, the desired pharmacokinetic and/or pharmacodynamic profile described herein are obtained via the modification of dosage form, the at least one pharmaceutically acceptable carrier, the amount of steroidal compound (e.g., a testosterone alkyl ester, such as testosterone undecanoate) present, combinations thereof, or the like. In certain embodiments, the population of individuals is one, one or more, two or more, or a statistically significant number of individuals.

Provided in certain embodiments herein are androgen therapies (e.g., testosterone undecanoate therapies), pharmaceutical compositions or oral dosage forms described herein that provide or are formulated to provide a plasma concentration of testosterone at steady state that is between about 200 ng/dL and 1300 ng/dL in at least 75%, at least 80%, at least 85%, at least 90%, at least 95%, or at least 99% of a population of individuals when administered to the population of individuals. In some embodiments androgen therapies (e.g., testosterone undecanoate therapies), pharmaceutical compositions or oral dosage forms described herein provide or are formulated to provide a plasma concentration of testosterone at steady state that is between about 200 ng/dL and 1100 ng/dL in at least 75%, at least 80%, at least 85%, at least 90%, at least 95%, or at least 99% of a population of individuals when administered to the population of individuals. In certain embodiments pharmaceutical compositions or oral dosage forms described herein provide or are formulated to provide a plasma concentration of testosterone at steady state that is between about 300 ng/dL and 1000 ng/dL in at least 50%, at least 60%, at least 70%, at least 75%, at least 80%, at least 85%, at least 90%, at least 95%, or at least 99% of a population of individuals when administered to the population of individuals.

In some embodiments, a pharmaceutical composition or oral dosage form described herein (e.g., for use in a steroidal, such as testosterone undecanoate, therapy) is formulated such that a single administration of the pharmaceutical composition or oral dosage form provides a mean plasma $C_{max}$ of testosterone that is about 19 ng/mL or less, about 18 ng/mL or less, about 17 ng/mL or less, about 16 ng/mL or less, about 15 ng/mL or less, about 14 ng/mL or less, about 5 ng/mL to about 19 ng/mL, about 5 ng/mL to about 18 ng/mL, about 5 ng/mL to about 17 ng/mL, about 5 ng/mL to about 16 ng/mL, about 5 ng/mL to about 15 ng/mL, about 5 ng/mL to about 14 ng/mL, about 7 ng/mL to about 19 ng/mL, about 7 ng/mL to about 18 ng/mL, about 7 ng/mL to about 17 ng/mL, about 7 ng/mL to about 16 ng/mL, about 7 ng/mL to about 15 ng/mL, about 7 ng/mL to about 14 ng/mL, about 10 ng/mL to about 19 ng/mL, about 10 ng/mL to about 18 ng/mL, about 10 ng/mL to about 17 ng/mL, about 10 ng/mL to about 16 ng/mL, about 10 ng/mL to about 15 ng/mL, or about 10 ng/mL to about 14 ng/mL. In specific embodiments, an oral dosage form described herein is formulated such that a single administration of the oral dosage form provides a mean plasma $C_{max}$ of testosterone that is about 15 ng/mL or less, about 19 ng/mL or less, about 5 ng/mL to about 19 ng/mL, or about 5 ng/mL to about 15 ng/mL. In certain embodiments, a pharmaceutical composition or oral dosage form described herein is formulated such that a single administration of the pharmaceutical composition or oral dosage form provides a mean plasma $C_{max}$ of dihydrotestosterone that is about 4.5 ng/mL or less, about 4.3 ng/mL or less, about 4.2 ng/mL or less, about 4.1 ng/mL or less, about 4 ng/mL or less, about 3.9 ng/mL or less, about 3.8 ng/mL or less, about 3.7 ng/mL or less, about 3.6 ng/mL or less, about 3.5 ng/mL or less, about 1.5 ng/mL to about 4.5 ng/mL, about 1.5 ng/mL to about 3.9 ng/mL, about 1.5 ng/mL to about 3.8 ng/mL, about 1.5 ng/mL to about 3.7 ng/mL, about 1.5 about 3.6 ng/mL, about 1.5 ng/mL to about 3.5 ng/mL, about 2.0 ng/mL to about 4.5 ng/mL, about 2.0 ng/mL to about 3.9 ng/mL, about 2.0 ng/mL to about 3.8 ng/mL, about 2.0 ng/mL to about 3.7 ng/mL, about 2.0 ng/mL to about 3.6 ng/mL, about 2.0 ng/mL to about 3.5 ng/mL, about 2.5 ng/mL to about 3.9 ng/mL, about 2.5 ng/mL to about 3.8 ng/mL, about 2.5 ng/mL to about 3.7 ng/mL, about 2.5 ng/mL to about 3.6 ng/mL, or about 2.5 ng/mL to about 3.5 ng/mL. In specific embodiments, a pharmaceutical composition or oral dosage form described herein is formulated such that a single administration of the pharmaceutical composition or oral dosage form provides a mean plasma $C_{max}$ of dihydrotestosterone that is about 3.6 ng/mL or less upon oral administration. In certain embodiments, a pharmaceutical composition or oral dosage form described herein is formulated such that a single administration of the pharmaceutical composition or oral dosage form provides a mean plasma $C_{max}$ of testosterone alkyl ester (e.g., testosterone undecanoate) that is about 400 ng/mL or less, about 380 ng/mL or less, about 360 ng/mL or less, about 340 ng/mL or less, about 320 ng/mL or less, about 300 ng/mL or less, or about 280 ng/mL or less, about 100 ng/mL to about 400 ng/mL, about 100 ng/mL to about 380 ng/mL, about 100 ng/mL to about 360 ng/mL, about 100 ng/mL to about 340 ng/mL, about 100 ng/mL to about 320 ng/mL, about 100 ng/mL to about 300 ng/mL, about 100 ng/mL to about 280 ng/mL, about 150 ng/mL to about 400 ng/mL, about 150 ng/mL to about 380 ng/mL, about 150 ng/mL to about 360 ng/mL, about 150 ng/mL to about 340 ng/mL, about 150 ng/mL to about 320 ng/mL, about 150 ng/mL to about 300 ng/mL, about 150 ng/mL to about 280 ng/mL, about 200 ng/mL to about 400 ng/mL, about 200 ng/mL to about 380 ng/mL, about 200 ng/mL to about 360 ng/mL, about 200 ng/mL to about 340 ng/mL, about 200 ng/mL to about 320 ng/mL, about 200 ng/mL to about 300 ng/mL, or about 200 ng/mL to about 280 ng/mL. In specific embodiments, a pharmaceutical composition or oral dosage form described herein is formulated such that a single administration of the pharmaceutical composition or oral dosage form provides a mean plasma $C_{max}$ of testosterone undecanoate that is about 380 ng/mL or less upon oral administration. In some embodiments, a pharmaceutical composition or oral dosage form described herein (e.g., for use in a steroidal, such as testosterone undecanoate, therapy) is formulated such that a single administration of the pharmaceutical composition or oral dosage form provides a mean plasma $C_{max}$ of testosterone that is about 5 ng/mL to about 15 ng/mL, a mean plasma $C_{max}$ of dihydrotestosterone that is about 1.5 ng/mL to about 3.8 ng/mL, and a mean plasma $C_{max}$ of testosterone alkyl ester (e.g., testosterone undecanoate) that is about 100 ng/mL to about 380 ng/mL. In certain embodiments, a pharmaceutical composition or oral dosage form described herein (e.g., for use in a steroidal, such as testosterone undecanoate, therapy) is formulated such that a single administration of the pharmaceutical composition or oral dosage form provides a mean plasma $C_{max}$ of testosterone that is about 5 ng/mL to about 19 ng/mL, a mean plasma $C_{max}$ of dihydrotestosterone that is about 1.5 ng/mL to about 4.5 ng/mL, and a mean plasma $C_{max}$ of testosterone alkyl ester (e.g., testosterone undecanoate) that is about 100 ng/mL to about 380 ng/mL.

In some embodiments, provided herein is a pharmaceutical composition or oral dosage form formulated such that it provides a mean plasma concentration of testosterone that is about 200 ng/dL or less, about 150 ng/dL or less, about 100 ng/dL or less, or about 75 ng/dL or less, about 5 ng/dL to about 200 ng/dL, about 5 ng/dL to about 150 ng/dL, about 5 ng/dL to about 100 ng/dL, about 5 ng/dL to about 75 ng/dL, about 10 ng/dL to about 200 ng/dL, about 10 ng/dL to about 150 ng/dL, about 10 ng/dL to about 100 ng/dL, about 10 ng/dL to about 75 ng/dL, about 15 ng/dL to about 200 ng/dL, about 15 ng/dL, to about 150 ng/dL, about 15 ng/dL to about 100 ng/dL, or about 15 ng/dL to about 75 ng/dL 1 hour after a single oral administration. In certain embodiments, provided herein is a pharmaceutical composition or oral dosage form formulated such that it provides a mean plasma concentration of testosterone that is about 500 ng/dL or less, about 400 ng/dL or less, about 300 ng/dL or less, about 200 ng/dL or less, about 150 ng/dL or less, about 5 ng/dL to about 500 ng/dL, about 5 ng/dL to about 400 ng/dL, about 5 ng/dL to about 300 ng/dL, about 5 ng/dL to about 200 ng/dL, about 5 ng/dL to about 150 ng/dL, about 10 ng/dL to about 500 ng/dL, about 10 ng/dL to about 400 ng/dL, about 10 ng/dL to about 300 ng/dL, about 10 ng/dL to about 200 ng/dL, about 10 ng/dL to about 150 ng/dL, about 15 ng/dL to about 500 ng/dL, about 15 ng/dL to about 400 ng/dL, about 15 ng/dL to about 300 ng/dL, about 15 ng/dL to about 200 ng/dL, about 15 ng/dL to about 150 ng/dL 2 hour after a single oral administration. In some embodiments, provided herein is a pharmaceutical composition or oral dosage form formulated such that it provides a mean plasma concentration of testosterone that is about 5 ng/dL to about 150 ng/dL 1 hour after a single oral administration, and about 10 ng/dL to about 500 ng/dL 2 hours after a single oral administration.

In certain embodiments, pharmaceutical compositions described herein comprise or are formulated into one or more oral dosage form described herein. Therefore, in some embodiments, in order to arrive at the targeted plasma concentration (e.g., at a specific concentration at a given time, $C_{max}$, $C_{min}$, or the like), a plurality of oral dosage forms described herein are optionally administered. Furthermore, as used herein, a mean plasma concentration (e.g., at a specific concentration at a given time, $C_{max}$, $C_{min}$, or the like) is the mean of a plurality of concentration values obtained from the plasma of a plurality of individuals following oral administration of an oral dosage form described herein to the plurality of individuals. In some embodiments, the individuals are adult humans. In specific embodiments, the adult humans are adult male humans. In certain embodiments, the individuals are adult hypogonadal or otherwise androdeficient adult male humans. In some embodiments, the individuals are postmenopausal or otherwise androdeficient adult female humans. Furthermore, it is noted that concentrations of testosterone alkyl ester described herein include the concentration of the one or more testosterone alkyl ester administered.

In some embodiments, provided herein is a pharmaceutical composition or oral dosage form that releases or is formulated to release about 90% or less, about 80% or less, about 70% or less, about 60% or less, about 55% or less, about 50% or less, about 45% or less, about 40% or less, about 35% or less, about 5% to about 90%, about 5% to about 80%, about 5% to about 70%, about 5% to about 60%, about 5% to about 55%, about 5% to about 50%, about 5% to about 45%, about 5% to about 40%, about 5% to about 35%, about 20% to about 90%, about 20% to about 80%, about 20% to about 70%, about 20% to about 60%, about 20% to about 55%, about 20% to about 50%, about 20% to about 45%, about 20% to about 40%, or about 20% to about 35% of the testosterone alkyl ester (e.g., testosterone undecanoate) after 1 hour in an aqueous medium (e.g., in 1 L deionized water comprising 8% w/v Triton X-100). In certain embodiments, provided herein is a pharmaceutical composition or oral dosage form that releases or is formulated to release about 90% or less, about 80% or less, about 70% or less, about 60% or less, about 50% or less, about 40% or less, about 30% or less, about 20% or less, about 2% to about 90%, about 2% to about 80%, about 2% to about 70%, about 2% to about 60%, about 2% to about 50%, about 2% to about 40%, about 2% to about 30%, about 2% to about 20%, about 10% to about 90%, about 10% to about 80%, about 10% to about 70%, about 10% to about 60%, about 10% to about 50%, about 10% to about 40%, about 10% to about 30%, or about 10% to about 20% of the testosterone alkyl ester (e.g., testosterone undecanoate) after 30 minutes in an aqueous medium (e e.g., in 1 L deionized water comprising 8% w/v Triton X-100). In some embodiments, provided herein is a pharmaceutical composition or oral dosage form that releases or is formulated to release about 99% or less, about 98% or less, about 97% or less, about 96% or less, about 95% or less, about 90% or less, about 10% to about 99%, about 10% to about 98%, about 10% to about 97%, about 10% to about 96%, about 10% to about 95%, about 10% to about 90%, about 40% to about 99%, about 40% to about 98%, about 40% to about 97%, about 40% to about 96%, about 40% to about 95%, about 40% to about 90%, about 70% to about 99%, about 70% to about 98%, about 70% to about 97%, about 70% to about 96%, about 70% to about 95%, or about 70% to about 90% of the testosterone alkyl ester (e.g., testosterone undecanoate) after 3 hour in an aqueous medium (e.g., in 1 L deionized water comprising 8% w/v Triton X-100). In some embodiments, provided herein is a pharmaceutical composition or oral dosage form that releases or is formulated to release more than 80% of the testosterone alkyl ester (e.g., testosterone undecanoate) within 12, 10, 8, 6, 5, 4, 3, or 2 hours in an aqueous medium (e.g., in 1 L deionized water comprising 8% w/v Triton X-100). In specific embodiments, provided herein is a pharmaceutical composition or oral dosage form that releases or is formulated to release about 20% or less of the testosterone alkyl ester after 30 minutes, 50% or less of the testosterone alkyl ester (e.g., testosterone undecanoate) after 1 hour and about 95% or less of the testosterone alkyl ester after 3 hours in an aqueous medium (e.g., in 1 L deionized water comprising 8% w/v Triton X-100). In some embodiments, provided herein is a pharmaceutical composition or oral dosage form that releases or is formulated to release about 5% to about 60% of the testosterone alkyl ester (e.g., testosterone undecanoate) after 1 hour, about 2% to about 40% of the testosterone alkyl ester after 30 minutes, and about 10% to about 95% of the testosterone alkyl ester after 2 hours in an aqueous medium (e.g., in 1 L deionized water comprising 8% w/v Triton X-100). In certain specific embodiments, provided herein is a pharmaceutical composition or oral dosage form that releases or is formulated to release about 50% or less of the testosterone alkyl ester (e.g., testosterone undecanoate) after 1 hour, and 80% or less of the testosterone alkyl ester (e.g., testosterone undecanoate) within 2-12 hours (or after 12 hours, 10 hours, 8 hours, 6 hours, 5 hours, 4 hours, 3 hours, or 2 hours) in an aqueous medium (e.g., in 1 L deionized water comprising 8% w/v Triton X-100). In certain instances, the aqueous medium is 1 L deionized water comprising 8% w/v Triton X-100 (e.g., octylphenol ethylene oxide condensate; octoxynol-9; t-octylphenoxypolyethoxyethanol; t-oct-$C_6H_4$—$(OCH_2CH_2)_xOH$, x=9-10; CAS No. 9002-93-1; Triton X-100 was a registered trademark formerly owned by Rohm and Haas Co., but now owned by Union Carbide) at 37±0.5° C. and the pharmaceutical composition or oral dosage form is deposited therein and subjected to a paddle method at 100 rpm and 37±0.5° C. for the designated period of time (USP App 2).

In some embodiments, provided herein is a pharmaceutical composition or oral dosage form that provides or is formulated to provide a testosterone (e.g., in human males, adult human males, pubescent human males, or the like) mean plasma $C_{max}$ at steady state of about 1550 ng/dL or less, about 1500 ng/dL or less, about 1450 ng/dL or less, about 1400 ng/dL or less, about 1310 ng/dL or less, about 1300 ng/dL or less. In some embodiments, provided herein is a pharmaceutical composition or oral dosage form that provides or is formulated to provide a testosterone (e.g., in human males, adult human males, pubescent human males, or the like) mean plasma $C_{min}$ at steady state of about 100 ng/dL or more, about 150 ng/dL or more, about 200 ng/dL or more, about 250 ng/dL or more, or about 300 ng/dL or more. In specific embodiments, provided herein is a pharmaceutical composition or oral dosage form that provides or is formulated to provide a testosterone (e.g., in human males, adult human males, pubescent human males, or the like) mean plasma $C_{min}$ at steady state of about 200 ng/dL or more. In certain embodiments, provided herein is a pharmaceutical composition or oral dosage form that provides or is formulated to provide a testosterone (e.g., in human males, adult human males, pubescent human males, or the like) mean plasma concentration that ranges at steady state from about 100 ng/dL to about 1500 ng/dL, about 150 ng/dL to about 1400 ng/dL, about 200 ng/dL to about 1300 ng/dL or about 250 ng/dL to about 1200 ng/dL. In specific embodiments, provided herein is a pharmaceutical composition or oral dosage form that provides or is formulated to provide a testosterone (e.g., in human males, adult human males, pubescent human males, or the like) mean plasma concentration that ranges at steady state from about 200 ng/dL to about 1300 ng/dL.

In some embodiments, provided herein is a pharmaceutical composition or oral dosage form that provides or is formulated to provide a testosterone (e.g., in human females, adult human females, post menopausal human females, or the like) mean plasma $C_{max}$ at steady state of about 110 ng/dL or less, 100 ng/dL or less, about 95 ng/dL or less, about 90 ng/dL or less, about 85 ng/dL or less, or about 82 ng/dL or less. In some embodiments, provided herein is a pharmaceutical composition or oral dosage form that provides or is formulated to provide a testosterone (e.g., in human females, adult human females, post menopausal human females, or the like) mean plasma $C_{min}$ at steady state of about 3 ng/dL or more, about 5 ng/dL or more, about 8 ng/dL or more, about 10 ng/dL or more, or about 12 ng/dL or more. In specific embodiments, provided herein is a pharmaceutical composition or oral dosage form that provides or is formulated to provide a testosterone (e.g., in human females, adult human females, post menopausal human females, or the like) mean plasma $C_{min}$ at steady state of about 8 ng/dL or more. In certain embodiments, provided herein is a pharmaceutical composition or oral dosage form that provides or is formulated to provide a testosterone (e.g., in human males, adult human females, pubescent human fumales, postmenopausal human females, or the like) mean plasma concentration that ranges at steady state from about 5 ng/dL to about 110 ng/dL, about 8 ng/dL to about 100 ng/dL, about 10 ng/dL to about 90 ng/dL or about 12 ng/dL to about 82 ng/dL. In specific embodiments, provided herein is a pharmaceutical composition or oral dosage form that provides or is formulated to provide a testosterone (e.g., in human females, adult human females, post menopausal human females, or the like) mean plasma concentration that ranges at steady state from about 10 ng/dL to about 90 ng/dL.

Provided in certain embodiments herein is a pharmaceutical composition or oral dosage form that provides or is formulated to provide upon oral administration to an individual (e.g., an androgen deficient human male) a testosterone equivalent (e.g., mass of testosterone that can be derived from a testosterone alkyl ester (e.g., $C_2$-$C_{13}$)) dose to mean steady state testosterone $C_{max}$ ratio of about $500 \times 10^6$ mL or less. In some embodiments, a testosterone equivalent dose to mean steady state testosterone $C_{max}$ ratio is about $500 \times 10^6$ mL, or less; about $4 \times 10^5$ mL, or more; about $6 \times 10^5$ mL, or more; about $8 \times 10^5$ mL, or more; about $1 \times 10^6$ mL, or more; about $3 \times 10^6$ mL, or more; about $4 \times 10^6$ mL, or more; about $5 \times 10^6$ mL, or more; about $6 \times 10^6$ mL, or more; about $500 \times 10^6$ mL, or less; $400 \times 10^6$ mL or less; $300 \times 10^6$ mL, or less; $250 \times 10^6$ mL, or less; $200 \times 10^6$ mL, or less; $150 \times 10^6$ mL, or less; $100 \times 10^6$ mL, or less; about $25 \times 10^5$ mL, or more; about 100×10$^5$ mL, or more; about 250×10$^5$ mL, or more; about 500×10$^5$ mL, or more; about 4×10$^5$ mL to about 500×10$^6$ mL; about 4×10$^5$ mL to about 400×10$^6$ mL; about 4×10$^5$ mL to about 300×10$^6$ mL; about 4×10$^5$ mL to about 250×10$^6$ mL; about 4×10$^5$ mL to about 200×10$^6$ mL; about 4×10$^5$ mL to about 150×10$^6$ mL; about 20×10$^5$ mL to about 500×10$^6$ mL; about 20×10$^5$ mL to about 400×10$^6$ mL; about 20×10$^5$ mL to about 300×10$^6$ mL; about 20×10$^5$ mL to about 250×10$^6$ mL; about 20×10$^5$ mL to about 200×10$^6$ mL; about 20×10$^5$ mL to about 150×10$^6$ mL; about 50×10$^5$ mL to about 500×10$^6$ mL; about 50×10$^5$ mL to about 400×10$^6$ mL; about 50×10$^5$ mL to about 300×10$^6$ mL; about 50×10$^5$ mL to about 250×10$^6$ mL; about 50×10$^5$ mL to about 200×10$^6$ mL; about 50×10$^5$ mL to about 150×10$^6$ mL; about 200×10$^5$ mL to about 500×10$^6$ mL; about 200×10$^5$ mL to about 400×10$^6$ mL; about 200×10$^5$ mL to about 300×10$^6$ mL; about 200×10$^5$ mL to about 250×10$^6$ mL; about 200×10$^5$ mL to about 200×10$^6$ mL; about 200×10$^5$ mL to about 150×10$^6$ mL; or the like. In some embodiments, a single dose of any oral dosage form or pharmaceutical composition described herein provides, upon oral administration to an individual (e.g., an androgen deficient human male), a ratio testosterone equivalent dose to mean plasma testosterone $C_{max}$ that is about 500×10$^6$ mL or less. In some embodiments, a single administration provides a testosterone equivalent dose to mean testosterone $C_{max}$ ratio that is about 500×10$^6$ mL, or less; about 4×10$^5$ mL, or more; 500×10$^6$ mL, or less; 400×10$^6$ mL, or less; 300×10$^6$ mL, or less; 250×10$^6$ mL, or less; 200×10$^6$ mL, or less, 150×10$^6$ mL, or less; 100×10$^6$ mL, or less; about 25×10$^5$ mL, or more; about 100×10$^5$ mL, or more; about 250×10$^5$ mL, or more; about 500×10$^5$ mL, or more; about 4×10$^5$ mL to about 500×10$^6$ mL; about 4×10$^5$ mL to about 400×10$^6$ mL; about 4×10$^5$ mL to about 300×10$^6$ mL; about 4×10$^5$ mL to about 250×10$^6$ mL; about 4×10$^5$ mL to about 200×10$^6$ mL; about 4×10$^5$ mL to about 150×10$^6$ mL; about 20×10$^5$ mL to about 500×10$^6$ mL; about 20×10$^5$ mL to about 400×10$^6$ mL; about 20×10$^5$ mL to about 300×10$^6$ mL; about 20×10$^5$ mL to about 250×10$^6$ mL; about 20×10$^5$ mL to about 200×10$^6$ mL; about 20×10$^5$ mL to about 150×10$^6$ mL; about 50×10$^5$ mL to about 500×10$^6$ mL; about 50×10$^5$ mL to about 400×10$^6$ mL; about 50×10$^5$ mL to about 300×10$^6$ mL; about 50×10$^5$ mL to about 250×10$^6$ mL; about 50×10$^5$ mL to about 200×10$^6$ mL; about 50×10$^5$ mL to about 150×10$^6$ mL; about 200×10$^5$ mL to about 500×10$^6$ mL; about 200×10$^5$ mL to about 400×10$^6$ mL; about 200×10$^5$ mL to about 300×10$^6$ mL; about 200×10$^5$ mL to about 250×10$^6$ mL; about 200×10$^5$ mL to about 200×10$^6$ mL; about 200×10$^5$ mL to about 150×10$^6$ mL; or the like. In some embodiments, a single administration provides a testosterone equivalent dose to mean dihydroxytestosterone $C_{max}$ ratio that is about 350×10$^6$ mL, or less; about 20×10$^5$ mL, or more; 500×10$^6$ mL, or less; 400×10$^6$ mL, or less; 300×10$^6$ mL, or less; 250×10$^6$ mL, or less; 200×10$^6$ mL, or less; 150×10$^6$ mL, or less; 100×10$^6$ mL, or less; about 25×10$^5$ mL, or more; about 100×10$^5$ mL, or more; about 250×10$^5$ mL, or more; about 500×10$^5$ mL, or more; about 20×10$^5$ mL to about 500×10$^6$ mL; about 20×10$^5$ mL to about 400×10$^6$ mL; about 20×10$^5$ mL to about 300×10$^6$ mL; about 20×10$^5$ mL to about 250×10$^6$ mL; about 20×10$^5$ mL to about 200×10$^6$ mL; about 20×10$^5$ mL to about 150×10$^6$ mL; about 50×10$^5$ mL to about 500×10$^6$ mL; about 50×10$^5$ mL to about 400×10$^6$ mL; about 50×10$^5$ mL to about 300×10$^6$ mL; about 50×10$^5$ mL to about 250×10$^6$ mL; about 50×10$^5$ mL to about 200×10$^6$ mL; about 50×10$^5$ mL to about 150×10$^6$ mL; about 200×10$^5$ mL to about 500×10$^6$ mL; about 200×10$^5$ mL to about 400×10$^6$ mL; about 200×10$^5$ mL to about 300×10$^6$ mL; about 200×10$^5$ mL to about 250×10$^6$ mL; about 200× 10$^5$ mL to about 200×10$^6$ mL; about 200×10$^5$ mL to about 150×10$^6$ mL; or the like. In certain instances, a steroid equivalent dose (e.g., testosterone equivalent dose) of a composition or dosage form described herein is the amount of steroid compound (e.g., testosterone) present (e.g., the steroidal portion of a steroidal compound, such as a testosterone alkyl ester) in the composition or dosage form and can be determined by calculating, e.g., (mass testosterone/mass testosterone alkyl ester)*amount of testosterone alkyl ester in the composition or dosage form.

Provided in certain embodiments herein is a pharmaceutical composition or oral dosage form that provides or is formulated to provide a difference between the mean plasma $C_{max}$ of testosterone at steady state and mean plasma $C_{min}$ of testosterone at steady state that is about 20 ng/mL or less, about 19 ng/mL or less, about 18 ng/mL or less, about 17 ng/mL or less, about 16 ng/mL or less, about 15 ng/mL or less, about 14 ng/mL or less, about 13 ng/mL or less, about 12 ng/mL or less, about 11 ng/mL or less, about 10.8 ng/mL or less, about 2 to about 20 ng/mL, about 2 to about 18 ng/mL, about 2 to about 16 ng/mL, about 2 to about 15 ng/mL, about 2 to about 14 ng/mL, about 2 to about 13 ng/mL, about 2 to about 12 ng/mL, about 2 to about 11 ng/mL, about 5 to about 15 ng/mL, about 5 to about 14 ng/mL, about 5 to about 13 ng/mL, about 5 to about 12 ng/mL, or about 5 to about 11 ng/mL. In specific embodiments, the pharmaceutical composition or oral dosage form provides or is formulated to provide a difference between the mean plasma $C_{max}$ of testosterone at steady state and mean plasma $C_{min}$ of testosterone at steady state that is about 11 ng/mL or less. Furthermore, in some embodiments, provided herein is a pharmaceutical composition or oral dosage form provided herein provides or is formulated to provide a difference between the mean plasma $C_{max}$ and the mean $C_{min}$ of testosterone alkyl ester (e.g., testosterone undecanoate) is about 275 ng/mL or less, about 260 ng/mL or less, about 250 ng/mL or less, about 240 ng/mL or less, about 230 ng/mL or less, about 225 ng/mL or less, about 220 ng/mL or less, about 210 ng/mL or less, about 200 ng/mL or less, about 190 ng/mL or less, or about 180 ng/mL or less. In specific embodiments, provided herein is a pharmaceutical composition or oral dosage form provided herein provides or is formulated to provide a difference between the mean plasma $C_{max}$ and mean plasma $C_{min}$ of testosterone alkyl ester (e.g., testosterone undecanoate) is about 200 ng/mL or less. In specific embodiments, provided herein is a pharmaceutical composition or oral dosage form provided herein provides or is formulated to provide a difference between the mean plasma $C_{max}$ and mean plasma $C_{min}$ of testosterone alkyl ester (e.g., testosterone undecanoate) is about 275 ng/mL or less.

In some embodiments, provided herein is a pharmaceutical composition or oral dosage form that is formulated such that it provides, following a single oral administration, a mean plasma AUC$_{0-\infty}$ concentration of testosterone of about 120 ng·h/mL or less, about 110 ng·h/mL or less, about 100 ng·h/mL or less, about 90 ng·h/mL or less, about 80 ng·h/mL or less, about 70 ng·h/mL or less, about 60 ng·h/mL or less, about 20 ng·h/mL to about 110 ng·h/mL, about 20 ng·h/mL to about 100 ng·h/mL, about 20 ng·h/mL to about 90 ng·h/mL, about 20 ng·h/mL to about 80 ng·h/mL, about 20 ng·h/mL to about 70 ng·h/mL, about 20 ng·h/mL to about 60 ng·h/mL, about 30 ng·h/mL to about 110 ng·h/mL, about 30 ng·h/mL to about 100 ng·h/mL, about 30 ng·h/mL to about 90 ng·h/mL, about 30 ng·h/mL to about 80 ng·h/mL, about 30 ng·h/mL to about 70 ng·h/mL, about 30 ng·h/mL to about 60 ng·h/mL, about 40 ng·h/mL to about 110 ng·h/mL, about 40 ng·h/mL to about 100 ng·h/mL, about 40 ng·h/mL to about 90 ng·h/mL, about 40 ng·h/mL to about 80 ng·h/mL, about 40 ng·h/mL to about 70 ng·h/mL, about 40 ng·h/mL to about 60 ng·h/mL, about 50 ng·h/mL to about 110 ng·h/mL, about 50 ng·h/mL to about 100 ng·h/mL, about 50 ng·h/mL to about 90 ng·h/mL, about 50 ng·h/mL to about 80 ng·h/mL, about 50 ng·h/mL to about 70 ng·h/mL, about 60 ng·h/mL to about 110 ng·h/mL, about 60 ng·h/mL to about 100 ng·h/mL, about 60 ng·h/mL to about 90 ng·h/mL, or about 60 ng·h/mL to about 80 ng·h/mL. In certain embodiments, provided herein is a pharmaceutical composition or oral dosage form that is formulated such that, following a single oral administration, it provides a mean plasma $AUC_{0-\infty}$ concentration of dihydrotestosterone of about 50 ng·h/mL or less, about 45 ng·h/mL or less, about 40 ng·h/mL or less, about 35 ng·h/mL or less, about 30 ng·h/mL or less, about 25 ng·h/mL or less, about 20 ng·h/mL or less, about 10 ng·h/mL to about 50 ng·h/mL, about 10 ng·h/mL to about 45 ng·h/mL, about 10 ng·h/mL to about 40 ng·h/mL, about 10 ng·h/mL to about 35 ng·h/mL, about 10 ng·h/mL to about 30 ng·h/mL, about 10 ng·h/mL to about 25 ng·h/mL, about 10 ng·h/mL to about 20 ng·h/mL, about 15 ng·h/mL to about 50 ng·h/mL, about 15 ng·h/mL to about 45 ng·h/mL, about 15 ng·h/mL to about 40 ng·h/mL, about 15 ng·h/mL to about 35 ng·h/mL, about 15 ng·h/mL to about 30 ng·h/mL, about 15 ng·h/mL to about 25 ng·h/mL, about 20 ng·h/mL to about 50 ng·h/mL, about 20 ng·h/mL to about 45 ng·h/mL, about 20 ng·h/mL to about 40 ng·h/mL, about 20 ng·h/mL to about 35 ng·h/mL, or about 20 ng·h/mL to about 30 ng·h/mL. In some embodiments, provided herein is a pharmaceutical composition or oral dosage form that is formulated such that, following a single oral administration, it provides a mean plasma $AUC_{0-\infty}$ concentration of testosterone alkyl ester (e.g., the one or more testosterone alkyl ester compounds, such as testosterone undecanoate, found in the composition or dosage form) of about 1200 ng·h/mL or less, about 1100 ng·h/mL or less, about 1000 ng·h/mL or less, about 900 ng·h/mL or less, about 850 ng·h/mL or less, about 800 ng·h/mL or less, about 750 ng·h/mL or less, about 100 ng·h/mL to about 1200 ng·h/mL, about 100 ng·h/mL to about 1100 ng·h/mL, about 100 ng·h/mL to about 1000 ng·h/mL, about 100 ng·h/mL to about 900 ng·h/mL, about 100 ng·h/mL to about 850 ng·h/mL, about 100 ng·h/mL to about 800 ng·h/mL, about 100 ng·h/mL to about 750 ng·h/mL, about 150 ng·h/mL to about 1200 ng·h/mL, about 150 ng·h/mL to about 1100 ng·h/mL, about 150 ng·h/mL to about 1000 ng·h/mL, about 150 ng·h/mL to about 900 ng·h/mL, about 150 ng·h/mL to about 850 ng·h/mL, about 150 ng·h/mL to about 800 ng·h/mL, about 150 ng·h/mL to about 750 ng·h/mL, about 200 ng·h/mL to about 1200 ng·h/mL, about 200 ng·h/mL to about 1100 ng·h/mL, about 200 ng·h/mL to about 1000 ng·h/mL, about 200 ng·h/mL to about 900 ng·h/mL, about 200 ng·h/mL to about 850 ng·h/mL, about 200 ng·h/mL to about 800 ng·h/mL, about 200 ng·h/mL to about 750 ng·h/mL, about 250 ng·h/mL to about 1200 ng·h/mL, about 250 ng·h/mL to about 1100 ng·h/mL, about 250 ng·h/mL to about 1000 ng·h/mL, about 250 ng·h/mL to about 900 ng·h/mL, about 250 ng·h/mL to about 850 ng·h/mL, about 250 ng·h/mL to about 800 ng·h/mL, about 250 ng·h/mL to about 750 ng·h/mL, about 300 ng·h/mL to about 1200 ng·h/mL, about 300 ng·h/mL to about 1100 ng·h/mL, about 300 ng·h/mL to about 1000 ng·h/mL, about 300 ng·h/mL to about 900 ng·h/mL, about 300 ng·h/mL to about 850 ng·h/mL, about 300 ng·h/mL to about 800 ng·h/mL, or about 300 ng·h/mL to about 750 ng·h/mL.

Provided in certain embodiments herein is any oral dosage form or pharmaceutical composition described herein that when a single dose is administered to an individual provides a testosterone equivalent dose to mean testosterone $AUC_{0-\infty}$ ratio of about $500 \times 10^3$ mL/h or less. In some embodiments, the testosterone equivalent dose to mean $AUC_{0-\infty}$ ratio is about $20 \times 10^3$ mL/h, or more; about $30 \times 10^3$ mL/h, or more; about $40 \times 10^3$ mL/h, or more; about $50 \times 10^3$ mL/h, or more; about $60 \times 10^3$ mL/h, or more; about $80 \times 10^3$ mL/h, or more; about $100 \times 10^3$ mL/h, or more; about $600 \times 10^3$ mL/h, or less; about $400 \times 10^3$ mL/h, or less; about $350 \times 10^3$ mL/h, or less; about $250 \times 10^3$ mL/h, or less; about $200 \times 10^3$ mL/h, or less; about $150 \times 10^3$ mL/h, or less; about 10 to about $600 \times 10^3$ mL/h; about 20 to about $500 \times 10^3$ mL/h; about 30 to about $450 \times 10^3$ mL/h; about 20 to about $400 \times 10^3$ mL/h; about 50 to about $300 \times 10^3$ mL/h; about 50 to about $200 \times 10^3$ mL/h; or the like.

In certain embodiments, a pharmaceutical composition or oral dosage form described herein achieves steady state upon administration in any manner suitable to achieve the steady state, e.g., once a day, twice a day, three times a day, four times a day, or the like. In specific embodiments, steady state is achieved after a period of time of b.i.d. oral administration (e.g., every 12 hours) of an oral dosage form described herein. In certain embodiments, steady state is obtained after, e.g., 2 days, 3 days, 4 days, 5 days, 6 days, 7 days, 2 weeks or longer, if or as necessary. In specific embodiments, steady state is obtained after b.i.d. oral administration for 5-7 days. Moreover, steady state plasma concentrations of testosterone, testosterone alkyl ester (e.g., testosterone undecanoate), and dihydrotestosterone are obtained, in certain instances, by administration of pharmaceutical compositions comprising about 1 mg to about 1 g, or about 10 mg to about 200 mg of a steroidal compound (e.g., a testosterone alkyl ester, such as testosterone undecanoate). In specific embodiments, a pharmaceutical composition (e.g., for administration to a human male) comprises about 10 mg to about 50 mg, about 15 mg to about 40 mg, about 20 mg, to about 30 mg, or about 25 mg of steroidal compound (e.g., a testosterone alkyl ester, such as testosterone undecanoate). In other embodiments, a pharmaceutical composition (e.g., for administration to a human male) comprises about 70 mg to about 150 mg, about 80 mg to about 140 mg, about 90 mg to about 140 mg, about 100 mg to about 130 mg, about 110 mg to about 130 mg, about 80 mg, or about 120 mg of a steroidal compound (e.g., a testosterone alkyl ester, such as testosterone undecanoate). In some embodiments, steady state of a testosterone, testosterone alkyl ester (e.g., testosterone undecanoate), and dihydrotestosterone are obtained by the administration of about 0.1 mg to about 5 mg of a steroidal compound (e.g., a testosterone alkyl ester, such as testosterone undecanoate) per kg of an individual to whom the oral dosage form is to be administered. In certain embodiments, testosterone, testosterone alkyl ester (e.g., testosterone undecanoate), and dihydrotestosterone are obtained by the oral administration of about 1 mg to about 1 g, about 5 mg to about 500 mg, about 10 mg to about 300 mg, or about 20 to about 250 mg of a steroidal compound (e.g., a testosterone alkyl ester, such as testosterone undecanoate) to an individual upon once a day, twice a day, three times a day, or four times a day. In certain embodiments, the pharmacokinetic and/or pharmacodynamic profiles described herein are obtained as a function of dose of steroidal compound and/or formulation of the pharmaceutical composition. In certain embodiments, an oral dosage form for administration to an human female comprises about 10% as much of a testosterone alkyl ester as does an oral dosage form for administration to an human male. In some embodiments, a pharmaceutical composition for delivery to an adult human female comprises about 5 mg to about 50 mg, about 5 mg to about 30 mg, about 7 mg to about 15 mg, about 8 mg to about 14 mg, about 9 mg to about 14 mg, about 10 mg to about 13 mg, about 11 mg to about 13 mg, about 8 mg, or about 12 mg of a testosterone alkyl ester, such as testosterone undecanoate.

Provided in certain embodiments herein is a pharmaceutical composition or oral dosage form that provides or is formulated to provide a delayed release dosage form. In specific embodiments, any delayed release oral dosage form described herein comprises one or more steroidal compound (e.g., one or more testosterone alkyl ester, such as testosterone undecanoate). In certain embodiments, a delayed release dosage form is one that releases about 90% or less, about 80% or less, about 70% or less, about 60% or less, about 55% or less, about 50% or less, about 45% or less, about 40% or less, about 35% or less, about 5% to about 90%, about 5% to about 80%, about 5% to about 70%, about 5% to about 60%, about 5% to about 55%, about 5% to about 50%, about 5% to about 45%, about 5% to about 40%, about 5% to about 35%, about 20% to about 90%, about 20% to about 80%, about 20% to about 70%, about 20% to about 60%, about 20% to about 55%, about 20% to about 50%, about 20% to about 45%, about 20% to about 40%, or about 20% to about 35% of the steroidal compound (e.g., a testosterone alkyl ester, such as testosterone undecanoate) after 1 hour in an aqueous medium; releases about 90% or less, about 80% or less, about 70% or less, about 60% or less, about 50% or less, about 40% or less, about 30% or less, about 20% or less, about 2% to about 90%, about 2% to about 80%, about 2% to about 70%, about 2% to about 60%, about 2% to about 50%, about 2% to about 40%, about 2% to about 30%, about 2% to about 20%, about 10% to about 90%, about 10% to about 80%, about 10% to about 70%, about 10% to about 60%, about 10% to about 50%, about 10% to about 40%, about 10% to about 30%, or about 10% to about 20% of the steroidal compound (e.g., a testosterone alkyl ester, such as testosterone undecanoate) after 30 minutes in an aqueous medium; releases about 99% or less, about 98% or less, about 97% or less, about 96% or less, about 95% or less, about 90% or less, about 10% to about 99%, about 10% to about 98%, about 10% to about 97%, about 10% to about 96%, about 10% to about 95%, about 10% to about 90%, about 40% to about 99%, about 40% to about 98%, about 40% to about 97%, about 40% to about 96%, about 40% to about 95%, about 40% to about 90%, about 70% to about 99%, about 70% to about 98%, about 70% to about 97%, about 70% to about 96%, about 70% to about 95%, or about 70% to about 90% of the steroidal compound (e.g., a testosterone alkyl ester, such as testosterone undecanoate) after 3 hour in an aqueous medium; and/or releases more than 80% of the steroidal compound (e.g., a testosterone alkyl ester, such as testosterone undecanoate) contained therein within 12, 10, 8, 6, 5, 4, 3, or 2 hours in an aqueous medium. Conversely, in some embodiments an immediate release dosage form (e.g., a fast release dosage form) comprising a steroidal compound (e.g., a testosterone alkyl ester, such as testosterone undecanoate) releases about 90% or more of the steroidal compound (e.g., a testosterone alkyl ester, such as testosterone undecanoate) contained therein within about 15 minutes of exposure to an aqueous medium. In some instances, the aqueous medium is present in a USP Type-II (paddle) apparatus with conditions at 37±0.5° C. and at 100 rpm. In more specific instances, the aqueous medium is about 1 L of DI water having 8% w/v of Triton X-100. Furthermore, in some embodiments, an immediate release dosage form of steroidal compound (e.g., a testosterone alkyl ester, such as testosterone undecanoate) is an oral dosage form (e.g., capsule) comprising the steroidal compound (e.g., a testosterone alkyl ester, such as testosterone undecanoate) formulated in a mixture of castor oil and propylene glycol laurate (e.g., a composition comprising testosterone undecanoate, castor oil and propylene glycol laurate, as currently marketed under the tradename Andriol®); or the steroidal compound (e.g., a testosterone alkyl ester, such as testosterone undecanoate) formulated in oleic acid (e.g., a composition comprising testosterone undecanoate and oleic acid, as previously marketed under the tradename Andriol®).

Furthermore, provided herein is a delayed release oral dosage form formulated such that it provides, following a single oral administration, a mean plasma concentration of testosterone that is at least 50% lower, at least 40% lower, at least 30% lower, at least 20% lower, at least 10% lower, at least 5% lower, about 50-95% lower, about 40-95% lower, about 30-95% lower, about 20-95% lower, about 50-90% lower, about 40-80% lower, about 30-80% lower, about 20-80% lower, about 40-60% lower, or about 10-95% lower measured after about 1 hour than is provided by a single dose of an immediate release oral dosage form having the same amount of steroidal compound (e.g., a testosterone alkyl ester, such as testosterone undecanoate). In specific embodiments, provided herein is a delayed release oral dosage form formulated such that it provides, following a single oral administration, a mean plasma concentration of testosterone that is at least 20% lower measured after about 1 hour than is provided by a single dose of an immediate release oral dosage form. In some embodiments, provided herein is a delayed release oral dosage form formulated such that it provides, following a single oral administration, a mean plasma concentration of testosterone that is at least 50% lower, at least 40% lower, at least 30% lower, at least 20% lower, at least 10% lower, about 50-95% lower, about 40-95% lower, about 30-95% lower, about 20-95% lower, about 40-60% lower, about 20-80% lower, about 10-60% lower, or about 10-95% lower measured after about 2 hours than is provided by a single dose of an immediate release oral dosage form. In specific embodiments, provided herein is a delayed release oral dosage form formulated such that it provides, following a single oral administration, a mean plasma concentration of testosterone that is at least 20% lower measured after about 2 hours than is provided by a single dose of an immediate release oral dosage form. In certain embodiments, provided herein is a delayed release oral dosage form formulated such that it provides, following a single oral administration, a mean plasma concentration of testosterone that is at least 50% lower, at least 40% lower, at least 30% lower, at least 20% lower, at least 10% lower, about 50-95% lower, about 40-95% lower, about 30-95% lower, about 20-95% lower, about 50-80% lower, about 40-80% lower, about 30-60% lower, about 20-50% lower, about 10-50% lower, or about 10-95% lower measured after about 3 hours than is prvided by a single dose of an immediate release oral dosage form. In specific embodiments, provided herein is a delayed release oral dosage form formulated such that it provides, following a single oral administration, a mean plasma concentration of testosterone that is at least 20% lower measured after about 3 hours than is provided by a single dose of an immediate release oral dosage form.

Provided in some embodiments herein is a delayed release oral dosage form formulated such that it provides, following a single oral administration, a mean plasma $C_{max}$ of testosterone that is at least 25% lower, at least 20% lower, at least 15% lower, at least 10% lower, at least 5% lower, about 25-95% lower, about 20-99% lower, about 15-99% lower, about 10-99% lower, about 25-50% lower, about 20-60% lower, about 15-40% lower, about 10-60lower, about 5-30% lower, or about 5-99% lower than the mean plasma $C_{max}$ of testosterone that is provided by a single dose of an immediate release oral dosage form having an identical amount of the steroidal compound (e.g., a testosterone alkyl ester, such as testosterone undecanoate) as is present in the delayed release oral dosage form. In certain embodiments, provided herein is a delayed release oral dosage form that provides or is formulated to provide, following a single oral administration, a mean plasma $C_{max}$ of the testosterone alkyl ester (e.g., testosterone undecanoate) that is at least 25% lower, at least 20% lower, at least 15% lower, at least 10% lower, at least 5% lower, about 25-95% lower, about 20-99% lower, about 15-99% lower, about 10-99% lower, about 5-99% lower, about 25-90% lower, about 20-80% lower, about 15-60% lower, about 10-60% lower, or about 5-40% lower than the mean plasma $C_{max}$ of testosterone alkyl ester that is provided by a single dose of an immediate release oral dosage form having an identical amount of the steroidal compound (e.g., a testosterone alkyl ester, such as testosterone undecanoate) as is present in the delayed release oral dosage form. In some embodiments, provided herein is a delayed release oral dosage form that provides or is formulated to provide, following oral administration, a mean plasma $C_{max}$ of dihydrotestosterone that is at least 10% lower, at least 8% lower, at least 7% lower, at least 6% lower, at least 5% lower, about 10-95% lower, about 8-99% lower, about 7-99% lower, about 6-99% lower, about 5-99% lower, about 5-15% lower, about 10-90% lower, about 8-80% lower, about 7-60% lower, about 10-60% lower, or about 5-40% lower than the mean plasma $C_{max}$ of dihydrotestosterone provided by a single dose of an immediate release oral dosage form having an identical amount of the steroidal compound (e.g., a testosterone alkyl ester, such as testosterone undecanoate) as is present in the delayed release oral dosage form.

Provided in certain embodiments herein is a delayed release oral dosage form that provides or is formulated to provide a mean plasma $C_{max}$ at steady state of testosterone alkyl ester that is at least 20% lower, at least 15% lower, at least 10% lower, at least 5% lower, about 20-95% lower, about 15-99% lower, about 10-99% lower, about 20-99% lower, about 15-99% lower, about 10-99% lower, about 5-99% lower, about 20-90% lower, about 20-80% lower, about 15-60% lower, about 10-60% lower, or about 5-40% lower than the mean plasma $C_{max}$ of steroidal compound (e.g., a testosterone alkyl ester, such as testosterone undecanoate) at steady state provided by an immediate release oral dosage form having an identical amount of the testosterone alkyl ester as is present in the delayed release oral dosage form. In some embodiments, a delayed oral dosage form comprising testosterone alkyl ester provided herein provides or is formulated to provide a mean plasma $C_{max}$ at steady state of testosterone that is at least 20% lower, at least 15% lower, at least 10% lower, at least 5% lower, about 20-95% lower, about 15-99% lower, about 10-99% lower, about 20-99% lower, about 15-99% lower, about 10-99% lower, about 10-30% lower, about 20-90% lower, about 20-80% lower, about 15-60% lower, about 10-60% lower, or about 10-40% lower than the mean plasma $C_{max}$ of testosterone at steady state provided by an immediate release oral dosage form having an identical amount of the steroidal compound (e.g., a testosterone alkyl ester, such as testosterone undecanoate) as is present in the delayed release oral dosage form.

In some embodiments, the delayed release oral dosage form provides a fluctuation index of testosterone at steady state that is at least 20% lower, at least 15% lower, at least 10% lower, at least 5% lower, about 20-95% lower, about 15-99% lower, about 10-99% lower, about 20-99% lower, about 15-99% lower, about 10-99% lower, about 5-99% lower, about 20-90% lower, about 20-80% lower, about 15-60% lower, about 10-60% lower, or about 5-40% lower than a fluctuation index of testosterone at steady state of an immediate release oral dosage form having an identical amount of the steroidal compound (e.g., a testosterone alkyl ester, such as testosterone undecanoate) as is present in the delayed release oral dosage form. In certain embodiments, the delayed release oral dosage form provides a fluctuation index of testosterone alkyl ester at steady state that is at least 20% lower, at least 15% lower, at least 10% lower, at least 5% lower, about 20-95% lower, about 15-99% lower, about 10-99% lower, about 20-99% lower, about 15-99% lower, about 10-99% lower, about 5-99% lower, about 20-90% lower, about 20-80% lower, about 15-60% lower, about 10-60% lower, or about 5-40% lower than a fluctuation index of testosterone alkyl ester at steady state of an immediate release oral dosage form having an identical amount of the testosterone alkyl ester as is present in the delayed release oral dosage form. In some embodiments, a pharmaceutical composition or oral dosage form provided herein that does not comprise oleate provides a fluctuation index of testosterone at steady state that is at least 20% lower, at least 15% lower, at least 10% lower, at least 5%, about 20-95% lower, about 15-99% lower, about 10-99% lower, about 20-99% lower, about 15-99% lower, about 10-99% lower, about 5-99% lower, about 20-90% lower, about 20-80% lower, about 15-60% lower, about 10-60% lower, or about 5-40% lower than a fluctuation index of testosterone at steady state provided by an oleate-containing oral dosage form having an identical amount of the steroidal compound (e.g., a testosterone alkyl ester, such as testosterone undecanoate). In certain embodiments, a pharmaceutical composition or oral dosage form provided herein that does not contain castor oil (unmodified by polyoxylation or hydrogenation) provides a fluctuation index of testosterone alkyl ester at steady state that is at least 20% lower, at least 15% lower, at least 10% lower, at least 5% lower, about 20-95% lower, about 15-99% lower, about 10-99% lower, about 20-99% lower, about 15-99% lower, about 10-99% lower, about 5-99% lower, about 20-90% lower, about 20-80% lower, about 15-60% lower, about 10-60% lower, or about 5-40% lower than a fluctuation index of testosterone alkyl ester at steady state of an castor oil-containing oral dosage form having an identical amount of the steroidal compound (e.g., a testosterone alkyl ester, such as testosterone undecanoate). As utilized herein, the fluctuation index is the difference between the mean plasma $C_{max}$ and mean plasma $C_{min}$ values that are achieved after administration of an dosage form.

In some embodiments, provided herein is a delayed oral dosage form that is formulated such that it provides, following a single oral administration, a mean plasma $AUC_{0-\infty}$ concentration of testosterone of that is at least 40%, at least 50% or at least 60% of the mean plasma $AUC_{0-\infty}$ concentration of testosterone provided by an immediate release dosage form.

Methods

In certain embodiments, provided herein are methods of treating an individual in need of an androgen therapy with any pharmaceutical composition or oral dosage form described herein. In some embodiments, provided are methods of treating androdeficiency in an individual in need thereof by administering to the individual any pharmaceutical composition or dosage form described herein, wherein the pharmaceutical composition or dosage form described herein comprises a therapeutically effective amount of a steroidal compound (e.g., one or more testosterone alkyl ester, such as testosterone undecanoate). In some embodiments, individuals are androdeficient (e.g., hypogonadal, andropausal, or otherwise androdeficient) adult male humans, young male humans who are suffering from delayed puberty (e.g., as a result of being hypogonadal), androdeficient (e.g., postmenopausal or otherwise androdeficient) adult female humans.

In specific embodiments, provided herein are methods of treating testosterone deficiency in male humans by administering to the male human any pharmaceutical composition or dosage form described herein, wherein the pharmaceutical composition or dosage form described herein comprises a therapeutically effective amount of one or more testosterone alkyl ester (e.g., testosterone undecanoate). In more specific embodiments, provided herein are methods of treating testosterone deficiency in hypogonadal male humans (e.g., adult or prepubescent male humans) by administering to the hypogonadal male human any pharmaceutical composition or dosage form described herein, wherein the pharmaceutical composition or dosage form described herein comprises a therapeutically effective amount of one or more testosterone alkyl ester (e.g., testosterone undecanoate). Symptoms of testosterone deficiency may include, by way of non-limiting example, one or more of depression, reduced libido, low energy, anemia, osteoporosis, debilitating muscle weakness, or the like. Therefore, in some embodiments, such symptoms, when caused by or suspected of being caused by andro- or testosterone deficiency, are also treated, either individually or collectively, by administering to a male human in need thereof a pharmaceutical composition or oral dosage form described herein. In some embodiments, provided herein are methods of treating testosterone deficiency in male humans by administering to the male human any pharmaceutical composition or dosage form described herein, wherein the pharmaceutical composition or dosage form described herein comprises a therapeutically effective amount of one or more testosterone alkyl ester (e.g., testosterone undecanoate) co-admnistered with a 5-alpha reductase enzyme inhibitor (e.g dutasteride, finesteride, isotertinoin, gallic acid, L-tysine, epigallocatechin gallate, saw palmetto, phytosterol complex, beta sitosterol, green tea extract, polyphenols etc.). In more specific embodiments, the enzyme inhibitor can be co-administered as a separate composition or be a part of the same testsosterone alkyl ester-conating composition.

In some embodiments, provided herein are methods of treating sexual dysfunction in an individual in need thereof by administering the individual any pharmaceutical composition or dosage form described herein, wherein the pharmaceutical composition or dosage form described herein comprises a therapeutically effective amount of a steroidal compound (e.g., one or more testosterone alkyl ester, such as testosterone undecanoate). In certain embodiments, the individual is a male adult human. In some embodiments, the individual is a female adult human.

In specific embodiments, provided herein are methods of treating andro-deficiency in female humans (e.g., adult female humans) by administering to the female human any pharmaceutical composition or dosage form described herein, wherein the pharmaceutical composition or dosage form described herein comprises a therapeutically effective amount of one or more testosterone alkyl ester (e.g., testosterone undecanoate). In some embodiments, provided herein are methods of maintaining muscle and/or bone mass in female humans (e.g., adult female humans) by administering to the female human any pharmaceutical composition or dosage form described herein, wherein the pharmaceutical composition or dosage form described herein comprises a therapeutically effective amount of one or more testosterone alkyl ester (e.g., testosterone undecanoate).

Provided in various embodiments of the methods described herein, administered are pharmaceutical compositions comprising therapeutically effective amounts of one or more steroidal compound (e.g., one or more testosterone alkyl ester, such as testosterone undecanoate). In some embodiments, a therapeutically effective amount is between about 1 mg and about 1 g, or about 10 mg to about 200 mg of one or more steroidal compound (e.g., one or more testosterone alkyl ester, such as testosterone undecanoate). In specific embodiments, a therapeutically effective amount is about 10 mg to about 50 mg, about 15 mg to about 40 mg, about 20 mg, to about 30 mg, or about 25 mg of one or more steroidal compound (e.g., one or more testosterone alkyl ester, such as testosterone undecanoate). In other embodiments, a therapeutically effective amount is about 70 mg to about 150 mg, about 80 mg to about 140 mg, about 90 mg to about 140 mg, about 100 mg to about 130 mg, about 110 mg to about 130 mg, or about 120 mg of one or more steroidal compound (e.g., one or more testosterone alkyl ester, such as testosterone undecanoate). In some embodiments, a therapeutically effective amount is about 0.1 mg to about 5 mg per kg of an individual to whom the oral dosage form is administered. In certain embodiments, a therapeutically effective amount is about 1 mg to about 1 g, about 5 mg to about 500 mg, about 10 mg to about 300 mg, or about 20 to about 250 mg of a steroidal compound (e.g., a testosterone alkyl ester, such as testosterone undecanoate) per day.

In certain embodiments, the methods described herein a plasma $C_{max}$ of testosterone that is less than 1500 ng/dL, about 100 ng/dL to about 1500 ng/dL, or about 500 ng/dL to about 1500 ng/dL in at least 85% of a population of individuals (following administration of a single dose and/or in the steady state). In some embodiments the methods described herein provide a plasma $C_{max}$ of testosterone that is less than 1800 ng/dL, about 100 ng/dL to about 1800 ng/dL, or about 500 ng/dL to about 1800 ng/dL in at least 95% of a population of individuals (following administration of a single dose and/or in the steady state). In some embodiments, the methods described herein provide a plasma $C_{max}$ of testosterone that is less than 2500 ng/dL, or about 100 ng/dL to 2500 ng/dL in all individuals (following administration of a single dose and/or in the steady state). In certain embodiments, the methods described herein provide a plasma concentration of testosterone at steady state that is between about 200 ng/dL and 1300 ng/dL in at least 75%, at least 80%, at least 85%, at least 90%, at least 95%, or at least 99% of a population of individuals. In some embodiments, the methods described herein provide a plasma concentration of testosterone at steady state that is between about 200 ng/dL and 1100 ng/dL in at least 75%, at least 80%, at least 85%, at least 90%, at least 95%, or at least 99% of a population of individuals. In certain embodiments, the methods described herein provide a plasma concentration of testosterone at steady state that is between about 300 ng/dL and 1000 ng/dL in at least 50%, at least 60%, at least 70%, at least 75%, at least 80%, at least 85%, at least 90%, at least 95%, or at least 99% of a population of individuals. Similarly, in various embodiments, the methods described herein provide any of the pharmacokinetic or pharmacodynamic profiles described for the pharmaceutical compositions or dosage forms described herein.

In various embodiments, the pharmaceutical compositions or dosage forms described herein are administered orally. In some embodiments, pharmaceutical compositions described herein comprise or are divided into one or more oral dosage forms described herein. Thus, in some embodiments, methods described herein comprise and/or pharmacokinetic or pharmacodynamic profiles described herein are achieved by administration of a plurality of oral dosage forms simultaneously, sequentially or in a substantially simultaneous manner. Furthermore, administration of pharmaceutical compositions or oral dosage forms described herein is achieved in any therapeutically effective manner. In some embodiments, the pharmaceutical composition or oral dosage form is administered once a day, twice a day, three times a day, four times a day, or the like. In some embodiments, a pharmaceutical composition or oral dosage form described herein is administered in the fed state. In certain embodiments, a pharmaceutical composition or oral dosage form described herein is administered with a meal, within 30 minutes of a meal, within 1 hour of a meal, or within 2 hours of a meal. In more specific embodiments, a pharmaceutical composition or oral dosage form described herein is administered with a meal, within 30 minutes after a meal, within 1 hour after a meal, or within 2 hours after a meal. In some embodiments, provided herein is a reduced food effect pharmaceutical composition or dosage form, the pharmaceutical composition or dosage form comprising the components as set forth in any embodiment described herein. In some embodiments, the reduced food effect pharmaceutical composition or dosage form provides, when orally administered in the fasted state, a maximum plasma concentration ($C_{max}$) of testosterone that is at least 90%, at least 80%, at least 70%, at least 60%, at least 50%, at least 40%, at least 30%, at least 20%, at least 15%, at least 10%, or at least 5% of the maximum plasma concentration ($C_{max}$) of testosterone provided when the same or identical pharmaceutical composition or dosage form is administered in the fed state. In certain embodiments, the reduced food effect pharmaceutical composition or dosage form provides, when orally administered in the fasted state, a maximum plasma concentration ($C_{max}$) of testosterone alkyl ester that is at least 90%, at least 80%, at least 70%, at least 60%, at least 50%, at least 40%, at least 30%, at least 20%, at least 15%, at least 10%, or at least 5% of the maximum plasma concentration ($C_{max}$) of testosterone alkyl ester provided when the same or identical pharmaceutical composition or dosage form is administered in the fed state. In some embodiments, the reduced food effect pharmaceutical composition or dosage form provides, when orally administered in the fasted state, a maximum plasma concentration ($C_{max}$) of dihydrotestosterone that is at least 90%, at least 80%, at least 70%, at least 60%, at least 50%, at least 40%, at least 30%, at least 20%, at least 15%, at least 10%, or at least 5% of the maximum plasma concentration ($C_{max}$) of dihydrotestosterone provided when the same or identical pharmaceutical composition or dosage form is administered in the fed state.

In certain embodiments, provided herein is a method of treating androgen deficiency in an individual, or a disorder associated therewith, the method comprising administering to an individual in need thereof a therapeutically effective amount of any composition described herein. In some embodiments, a composition adminstered according to a method described herein is formulated so as to provide any pharmacokinetic and/or pharmacodynamic effect described herein. In certain embodiments, methods provided herein comprise the administration of a sufficient amount of a composition described herein so as to provide any pharmacokinetic or pharmacodynamic effect described herein. In various embodiments, any protocol described herein for the administration of compositions is optionally utilized in any methods described herein.

Carriers

Provided herein are pharmaceutical compositions comprising a steroidal compound (e.g., one or more testosterone alkyl ester, such as testosterone undecanoate) and at least one pharmaceutically acceptable carrier. In certain embodiments, the at least one pharmaceutically acceptable carrier comprises at least one hydrophilic carrier (e.g., hydrophilic surfactant or additive), at least one lipophilic carrier (e.g., lipophilic surfactant or additive), and/or at least one viscosity enhancer or solidifying agent. In specific embodiments, the at least one pharmaceutically acceptable carrier is a hydrophilic carrier. In more specific embodiments, the at least one pharmaceutically acceptable carrier comprises or further comprises a lipophilic carrier. In further embodiments, the at least one pharmaceutically acceptable carrier comprises at least one hydrophilic carrier, at least one lipidic and/or lipophilic carrier, and at least one viscosity enhancer or solidifying agent.

In certain embodiments, hydrophilic carriers include, by way of non-limiting example, a hydrophilic surfactant. In various instances, hydrophilic surfactants are used to provide any one or more of several advantageous characteristics to the compositions, including, by way of non-limiting example: increased solubility of the active ingredient in at least one of the fractions of the carrier that is a solid carrier; improved dissolution of the active ingredient; improved dispersion and/or dissolution of the lipidic carrier; improved solubilization of the active ingredient upon dissolution; enhanced absorption and/or bioavailability of the active ingredient, particularly a hydrophilic, hydrophobic, or lipophilic active ingredient; and improved stability, both physical and chemical, of the active ingredient. In various embodiments, the hydrophilic surfactant includes either a single hydrophilic surfactant or a mixture of hydrophilic surfactants. Hydrophilic surfactants also include both ionic or non-ionic surfactants.

In some embodiments, lipophilic carriers include or further include, by way of non-limiting example, one or more lipophilic surfactant, including one or more lipophilic surfactant, one or more mono-, di-, or triglyceride, or mixtures thereof. In various instances, lipophilic surfactants provide any one or more of the advantageous characteristics listed above for hydrophilic surfactants, and/or enhance the function of other (e.g., hydrophilic) surfactants present in the pharmaceutical composition.

The terms "hydrophilic" and "lipophilic" are relative terms. Hydrophilicity and/or lipophilicity are determined in any manner suitable. In one instances, an empirical parameter is used to characterize the relative hydrophilicity and lipophilicity of the carriers described herein. For example, in one manner, the hydrophilicity and/or lipophilicity non-ionic amphiphilic compounds is the hydrophilic-lipophilic balance (the "HLB" value). Carriers or surfactants with lower HLB values are more lipophilic, and have greater solubility in oils, whereas surfactants with higher HLB values are more hydrophilic, and have greater solubility in aqueous mediums. This measure is suitable for the surfactants described herein because, generally, surfactants are amphiphilic as they comprise both a polar moiety (e.g., a polar non-charged or charged moiety) and a lipophilic moiety (e.g., an aliphatic group).

Using HLB values as a rough guide, hydrophilic surfactants are generally considered to be those compounds having an HLB value greater than about 10, as well as non-ionic, anionic, cationic, or zwitterionic compounds for which the HLB scale is not generally applicable. Similarly, lipophilic surfactants are compounds having an HLB value less than about 10.

It should be appreciated that the HLB value of a surfactant is merely a rough guide generally used to enable formulation of industrial, pharmaceutical and cosmetic emulsions. For many important surfactants, including several polyethoxylated surfactants, it has been reported that HLB values can differ by as much as about 8 HLB units, depending upon the empirical method chosen to determine the HLB value (Schott, *J Pharm. Sciences,* 79(1), 87-88 (1990)). Likewise, for certain polypropylene oxide containing block copolymers (poloxamers, available commercially as PLURONIC® surfactants, BASF Corp.), the HLB values are not always authoritative indicators of the true physical chemical nature of the compounds. Finally, commercial surfactant products are generally not pure compounds, but are often complex mixtures of compounds, and the HLB value reported for a particular compound may more accurately be characteristic of the commercial product of which the compound is a major component. Different commercial products having the same primary surfactant component can, and typically do, have different HLB values. In addition, a certain amount of lot-to-lot variability is expected even for a single commercial surfactant product. Thus, keeping these considerations involved, a person of ordinary skill in the art is able to utilize HLB values and the identity of a given product to determine surfactants for suitable lipophilicity and/or hydrophilicity for use in the pharmaceutical compositions described herein.

As used herein, useful surfactants include any surfactant that is pharmaceutically acceptable and is suitable for use in a pharmaceutical composition. Suitable surfactants include anionic, cationic, zwitterionic and non-ionic surfactants. Provided herein (e.g., in the Tables) are several general classes of surfactants. The HLB values given in the Tables below generally represent the HLB value as reported by the manufacturer of the corresponding commercial product. In cases where more than one commercial product is listed, the HLB value in the Tables is the value as reported for one of the commercial products, a rough average of the reported values, or a value that, in the judgment of the present inventors, is more reliable.

Surfactants described in the Tables are illustrative and are provided as non-limiting examples. For example, refined, distilled or fractionated surfactants, purified fractions thereof, or re-esterified fractions, are also within the scope of surfactants described herein, although they are not specifically listed in the Tables.

In some embodiments, surfactants described herein include polyoxylated fatty acids, such as polyethoxylated fatty acids (i.e., PEG-fatty acid esters). Provided in Table 1 is a list of illustrative and non-limiting examples of polyethoxylated fatty acid monoester surfactants.

TABLE 1

PEG-Fatty Acid Monoester Surfactants

| COMPOUND | COMMERCIAL PRODUCT (Supplier) | HLB |
| --- | --- | --- |
| PEG 4-100 monolaurate | Crodet L series (Croda) | >9 |
| PEG 4-100 monooleate | Crodet O series (Croda) | >8 |
| PEG 4-100 monostearate | Crodet S series (Croda), Myrj Series (Atlas/ICI) | >6 |
| PEG 400 distearate | Cithrol 4DS series (Croda) | >10 |
| PEG 100, 200, 300 monolaurate | Cithrol ML series (Croda) | >10 |
| PEG 100, 200, 300 monooleate | Cithrol MO series (Croda) | >10 |
| PEG 400 dioleate | Cithrol 4DO series (Croda) | >10 |
| PEG 400-1000 monostearate | Cithrol MS series (Croda) | >10 |
| PEG-1 stearate | Nikkol MYS-IEX (Nikko), Coster KI (Condea) | 2 |
| PEG-2 stearate | Nikkol MYS-2 (Nikko) | 4 |
| PEG-2 oleate | Nikkol MYO-2 (Nikko) | 4.5 |
| PEG-4 laurate | Mapeg ® 200 ML (PPG), Kessco ® PEG 200ML (Stepan), LIPOPEG 2L (LIPO Chem.) | 9.3 |
| PEG-4 oleate | Mapeg. ® 200 MO (PPG), Kessco. ® PEG200 MO (Stepan) | 8.3 |
| PEG-4 stearate | Kessco ® PEG 200 MS (Stepan), Hodag 20 S (Calgene), Nikkol MYS-4 (Nikko) | 6.5 |
| PEG-5 stearate | Nikkol TMGS-5 (Nikko) | 9.5 |
| PEG-5 oleate | Nikkol TMGO-5 (Nikko) | 9.5 |
| PEG-6 oleate | Algon OL 60 (Auschem SpA), Kessco ® PEG 300 MO (Stepan), Nikkol MYO-6 (Nikko), Emulgante A6 (Condea) | 8.5 |
| PEG-7 oleate | Algon OL 70 (Auschem SpA) | 10.4 |
| PEG-6 laurate | Kessco ® PEG300 ML (Stepan) | 11.4 |
| PEG-7 laurate | Lauridac 7 (Condea) | 13 |
| PEG-6 stearate | Kessco ® PEG300 MS (Stepan) | 9.7 |
| PEG-8 laurate | Mapeg ® 400 ML (PPG), LIPOPEG 4DL(Lipo Chem.) | 13 |
| PEG-8 oleate | Mapeg ® 400 MO (PPG), Emulgante A8 (Condea); Kessco PEG 400 MO (Stepan) | 12 |

TABLE 1-continued

PEG-Fatty Acid Monoester Surfactants

| COMPOUND | COMMERCIAL PRODUCT (Supplier) | HLB |
|---|---|---|
| PEG-8 stearate | Mapeg ® 400 MS (PPG), Myrj 45 | 12 |
| PEG-9 oleate | Emulgante A9 (Condea) | >10 |
| PEG-9 stearate | Cremophor 59 (BASF) | >10 |
| PEG-10 laurate | Nikkol MYL-10 (Nikko), Lauridac 10 (Croda) | 13 |
| PEG-10 oleate | Nikkol MYO-10 (Nikko) | 11 |
| PEG-10 stearate | Nikkol MYS-10 (Nikko), Coster K100 (Condea) | 11 |
| PEG-12 laurate | Kessco ® PEG 600ML (Stepan) | 15 |
| PEG-12 oleate | Kessco ® PEG 600MO (Stepan) | 14 |
| PEG-12 ricinoleate | (CAS #9004-97-1) | >10 |
| PEG-12 stearate | Mapeg ® 600 MS (PPG), Kessco ® PEG 600MS (Stepan) | 14 |
| PEG-15 stearate | Nikkol TMGS-15 (Nikko), Koster K15 (Condea) | 14 |
| PEG-15 oleate | Nikkol TMGO-15 (Nikko) | 15 |
| PEG-20 laurate | Kessco ® PEG 1000 ML (Stepan) | 17 |
| PEG-20 oleate | Kessco ® PEG 1000 MO (Stepan) | 15 |
| PEG-20 stearate | Mapeg ® 1000 MS (PPG), Kessco ® PEG 1000 MS (Stepan), Myrj 49 | 16 |
| PEG-25 stearate | Nikkol MYS-25 (Nikko) | 15 |
| PEG-32 laurate | Kessco ® PEG 1540 ML (Stepan) | 16 |
| PEG-32 oleate | Kessco ® PEG 1540 MO (Stepan) | 17 |
| PEG-32 stearate | Kessco ® PEG 1540 MS (Stepan) | 17 |
| PEG-30 stearate | Myrj 51 | >10 |
| PEG-40 laurate | Crodet L40 (Croda) | 17.9 |
| PEG-40 oleate | Crodet O40 (Croda) | 17.4 |
| PEG-40 stearate | Myrj 52, Emerest ® 2715 (Henkel), Nikkol MYS-40 (Nikko) | >10 |
| PEG-45 stearate | Nikkol MYS-45 (Nikko) | 18 |
| PEG-50 stearate | Myrj 53 | >10 |
| PEG-55 stearate | Nikkol MYS-55 (Nikko) | 18 |
| PEG-100 oleate | Crodet 0-100 (Croda) | 18.8 |
| PEG-100 stearate | Myrj 59, Arlacel 165 (ICI) | 19 |
| PEG-200 oleate | Albunol 200 MO (Taiwan Surf.) | >10 |
| PEG-400 oleate | LACTOMUL (Henkel), Albunol 400 MO (Taiwan Surf.) | >10 |
| PEG-600 oleate | Albunol 600 MO (Taiwan Surf) | >10 |

Furthermore, in some embodiments, surfactants described herein include, by way of non-limiting example, polyethylene glycol (PEG) fatty acid diesters. Illustrative and non-limiting examples of PEG-fatty acid diesters are shown in Table 2.

TABLE 2

PEG-Fatty Acid Diester Surfactants

| COMPOUND | COMMERCIAL PRODUCT (Supplier) | HLB |
|---|---|---|
| PEG-4 dilaurate | Mapeg ® 200 DL (PPG), Kessco ® PEG 200 DL (Stepan), LIPOPEG 2-DL (Lipo Chem.) | 7 / 6 |
| PEG-4 dioleate | Mapeg ® 200 DO (PPG) | 6 |
| PEG-4 distearate | Kessco ® 200 DS (Stepan) | 5 |
| PEG-6 dilaurate | Kessco ® PEG 300 DL (Stepan) | 9.8 |
| PEG-6 dioleate | Kessco ® PEG 300 DO (Stepan) | 7.2 |
| PEG-6 distearate | Kessco ® PEG 300 DS (Stepan) | 6.5 |
| PEG-8 dilaurate | Mapeg ® 400 DL (PPG), Kessco ® PEG 400 DL (Stepan), LIPOPEG 4 DL (Lipo Chem.) | 11 |
| PEG-8 dioleate | Mapeg ® 400 DO (PPG), Kessco ® PEG 400 DO (Stepan), LIPOPEG 4 DO(Lipo Chem.) | 8.8 |
| PEG-8 distearate | Mapeg ® 400 DS (PPG), CDS 400 (Nikkol) | 11 |
| PEG-10 dipalmitate | Polyaldo 2PKFG | >10 |
| PEG-12 dilaurate | Kessco ® PEG 600 DL (Stepan) | 11.7 |
| PEG-12 distearate | Kessco ® PEG 600 DS (Stepan) | 10.7 |
| PEG-12 dioleate | Mapeg ® 600 DO (PPG), Kessco ® 600 DO(Stepan) | 10 |
| PEG-20 dilaurate | Kessco ® PEG 1000 DL (Stepan) | 15 |
| PEG-20 dioleate | Kessco ® PEG 1000 DO (Stepan) | 13 |
| PEG-20 distearate | Kessco ® PEG 1000 DS (Stepan) | 12 |
| PEG-32 dilaurate | Kessco ® PEG 1540 DL (Stepan) | 16 |
| PEG-32 dioleate | Kessco ® PEG 1540 DO (Stepan) | 15 |
| PEG-32 distearate | Kessco ® PEG 1540 DS (Stepan) | 15 |
| PEG-400 dioleate | Cithrol 4DO series (Croda) | >10 |
| PEG-400 distearate | Cithrol 4DS series (Croda) | >10 |

As discussed above, in some embodiments, pharmaceutical compositions described herein comprise mixtures of surfactants, including, e.g., mixtures of two or more commercial surfactant products. Several PEG-fatty acid esters are marketed commercially as mixtures or mono- and diesters. Illustrative and non-limiting examples of surfactant mixtures are shown in Table 3.

TABLE 3

PEG-Fatty Acid Mono-and Diester Mixtures

| COMPOUND | COMMERCIAL PRODUCT (Supplier) | HLB |
|---|---|---|
| PEG 4-150 mono, dilaurate | Kessco ® PEG 200-6000 mono, dilaurate (Stepan) | |
| PEG 4-150 mono, dioleate | Kessco ® PEG 200-6000 mono, dioteate (Stepan) | |
| PEG 4-150 mono, distearate | Kessco ® 200-6000 mono, distearate (Stepan) | |

In some embodiments, surfactants described herein include, by way of non-limiting example, polyethylene glycol glycerol fatty acid esters (PEG glycerol fatty acid esters). Illustrative and non-limiting examples of PEG glycerol fatty acid esters are shown in Table 4.

TABLE 4

PEG Glycerol Fatty Acid Esters

| COMPOUND | COMMERCIAL PRODUCT (Supplier) | HLB |
|---|---|---|
| PEG-20 glyceryl laurate | Tagat ® L (Goldschmidt) | 16 |
| PEG-30 glyceryl laurate | Tagat ® L2 (Goldschmidt) | 16 |
| PEG-15 glyceryl laurate | Glycerox L series (Croda) | 15 |
| PEG-40 glyceryl laurate | Glycerox L series (Croda) | 15 |
| PEG-20 glyceryl stearate | Capmul ® EMG (ABITEC), Aldo ® MS-20 KFG (Lonza) | 13 |
| PEG-20 glyceryl oleate | Tagat ® O (Goldschmidt) | >10 |
| PEG-30 glyceryl oleate | Tagat ® O2 (Goldschmidt) | >10 |

In certain embodiments, surfactants of different degrees of lipophilicity or hydrophilicity are prepared by reaction of alcohols or polyalcohols with a variety of natural and/or hydrogenated oils. In some embodiments, the oils used are castor oil or hydrogenated castor oil or an edible vegetable oil such as corn oil, olive oil, peanut oil, palm kernel oil, apricot kernel oil, or almond oil. In specific embodiments, alcohols include glycerol, propylene glycol, ethylene glycol, polyethylene glycol, sorbitol, and pentaerythritol. In certain embodiments, such surfactants are utilized in the pharmaceutical compositions described herein. Illustrative and non-limiting examples of surfactants of this class suitable for use in the pharmaceutical compositions described herein are shown in Table 5.

TABLE 5

Transesterification Products of Oils and Alcohols

| COMPOUND | COMMERCIAL PRODUCT (Supplier) | HLB |
|---|---|---|
| PEG-3 castor oil | Nikkol CO-3 (Nikko) | 3 |
| PEG-5, 9, and 16 castor oil | ACCONON CA series (ABITEC) | 6-7 |
| PEG-20 castor oil | Emalex C-20 (Nihon Emulsion), Nikkol CO-20 TX (Nikko) | 11 |
| PEG-23 castor oil | Emulgante EL23 | >10 |
| PEG-30 castor oil | Emalex C-30 (Nihon Emulsion), Alkamuls ® EL 620 (Rhone-Poulenc), Incrocas 30 (Croda) | 11 |
| PEG-35 castor oil | Cremophor EL and EL-P (BASF), Emulphor EL, Incrocas-35 (Croda), Emulgin RO 35 (Henkel) | |
| PEG-38 castor oil | Emulgante EL 65 (Condea) | |
| PEG-40 castor oil | Emalex C-40 (Nihon Emulsion), Alkamuls ® EL 719 (Rhone-Poulenc) | 13 |
| PEG-50 castor oil | Emalex C-50 (Nihon Emulsion) | 14 |
| PEG-56 castor oil | Eumulgin ® PRT 56 (Pulcra SA) | >10 |
| PEG-60 castor oil | Nikkol CO-60TX (Nikko) | 14 |
| PEG-100 castor oil | Thornley | >10 |
| PEG-200 castor oil | Eumulgin ® PRT 200 (Pulcra SA) | >10 |
| PEG-5 hydrogenated castor oil | Nikkol HCO-5 (Nikko) | 6 |
| PEG-7 hydrogenated castor oil | Simusol ® 989 (Seppic), Cremophor WO7 (BASF) | 6 |
| PEG-10 hydrogenated castor oil | Nikkol HCO-10 (Nikko) | 6.5 |
| PEG-20 hydrogenated castor oil | Nikkol HCO-20 (Nikko) | 11 |
| PEG-25 hydrogenated castor oil | Simulsol ® 1292 (Seppic), Cerex ELS 250 (Auschem SpA) | 11 |
| PEG-30 hydrogenated castor oil | Nikkol HCO-30 (Nikko) | 11 |
| PEG-40 hydrogenated castor oil | Cremophor RH 40 (BASF), Croduret (Croda), Emulgin HRE 40 (Henkel) | 13 |
| PEG-45 hydrogenated castor oil | Cerex ELS 450 (Auschem Spa) | 14 |
| PEG-50 hydrogenated castor oil | Emalex HC-50 (Nihon Emulsion) | 14 |
| PEG-60 hydrogenated castor oil | Nikkol HCO-60 (Nikko); Cremophor RH 60 (BASF) | 15 |
| PEG-80 hydrogenated castor oil | Nikkol HCO-80 (Nikko) | 15 |
| PEG-100 hydrogenated castor oil | Nikkol HCO-100 (Nikko) | 17 |
| PEG-6 corn oil | Labrafil ® M 2125 CS (Gattefosse) | 4 |
| PEG-6 almond oil | Labrafil ® M 1966 CS (Gattefosse) | 4 |
| PEG-6 apricot kernel oil | Labrafil ® M 1944 CS (Gattefosse) | 4 |
| PEG-6 olive oil | Labrafil ® M 1980 CS (Gattefosse) | 4 |
| PEG-6 peanut oil | Labrafil ® M 1969 CS (Gattefosse) | 4 |
| PEG-6 hydrogenated palm kernel oil | Labrafil ® M 2130 BS (Gattefosse) | 4 |
| PEG-6 palm kernel oil | Labrafil ® M 2130 CS (Gattefosse) | 4 |
| PEG-6 triolein | Labrafil ® M 2735 CS (Gattefosse) | 4 |
| PEG-8 corn oil | Labrafil ® WL 2609 BS (Gattefosse) | 6-7 |
| PEG-20 corn glycerides | Crovol M40 (Croda) | 10 |
| PEG-20 almond glycerides | Crovol A40 (Croda) | 10 |
| PEG-25 trioleate | TAGAT ® TO (Goldschmidt) | 11 |
| PEG-40 palm kernel oil | Crovol PK-70 | >10 |
| PEG-60 corn glycerides | Crovol M70(Croda) | 15 |
| PEG-60 almond glycerides | Crovol A70 (Croda) | 15 |
| PEG-4 caprylic/capric triglyceride | Labrafac ® Hydro (Gattefosse), | 4-5 |
| PEG-8 caprylic/capric glycerides | Labrasol (Gattefosse), Labrafac CM 10 (Gattefosse) | >10 |
| PEG-6 caprylic/capric glycerides | SOFTIGEN ® 767 (Hüls), Glycerox 767 (Croda) | 19 |
| Lauroyl macrogol-32 glyceride | GELUCIRE 44/14 (Gattefosse) | 14 |
| Stearoyl macrogol glyceride | GELUCIRE 50/13 (Gattefosse) | 13 |
| Mono, di, tri, tetra esters of vegetable oils and sorbitol | SorbitoGlyceride (Gattefosse) | <10 |
| Pentaerythrityl tetraisostearate | Crodamol PTIS (Croda) | <10 |
| Pentaerythrityl distearate | Albunol DS (Taiwan Surf.) | <10 |
| Pentaerythrityl tetraoleate | Liponate PO-4 (Lipo Chem.) | <10 |
| Pentaerythrityl tetrastearate | Liponate PS-4 (Lipo Chem.) | <10 |

TABLE 5-continued

Transesterification Products of Oils and Alcohols

| COMPOUND | COMMERCIAL PRODUCT (Supplier) | HLB |
|---|---|---|
| Pentaerythrityl tetracaprylate/ tetracaprate | Liponate PE-810 (Lipo Chem.), Crodamol PTC (Croda) | <10 |
| Pentaerythrityl tetraoctanoate | Nikkol Pentarate 408 (Nikko) | |

In some embodiments, surfactants utilized in the pharmaceutical compositions described herein include, by way of non-limiting example, polyglycerized fatty acids. Illustrative and non-limiting examples of suitable polyglyceryl esters are shown in Table 6.

TABLE 6

Polyglycerized Fatty Acids

| COMPOUND | COMMERCIAL PRODUCT (Supplier) | HLB |
|---|---|---|
| Polyglyceryl-2 stearate | Nikkol DGMS (Nikko) | 5-7 |
| Polyglyceryl-2 oleate | Nikkol DGMO (Nikko) | 5-7 |
| Polyglyceryl-2 isostearate | Nikkol DGMIS (Nikko) | 5-7 |
| Polyglyceryl-3 oleate | Caprol ® 3G0 (ABITEC), Drewpol 3-1-O (Stepan) | 6.5 |
| Polyglyceryl-4 oleate | Nikkol Tetraglyn 1-O (Nikko) | 5-7 |
| Polyglyceryl-4 stearate | Nikkol Tetraglyn 1-S (Nikko) | 5-6 |
| Polyglyceryl-6 oleate | Drewpol 6-1-O (Stepan), Nikkol Hexaglyn 1-O (Nikko) | 9 |
| Polyglyceryl-10 laurate | Nikkol Decaglyn 1-L (Nikko) | 15 |
| Polyglyceryl-10 oleate | Nikkol Decaglyn 1-O (Nikko) | 14 |
| Polyglyceryl-10 stearate | Nikkol Decaglyn 1-S (Nikko) | 12 |
| Polyglyceryl-6 ricinoleate | Nikkol Hexaglyn PR-15 (Nikko) | |
| Polyglyceryl-10 linoleate | Nikkol Decaglyn I-LN (Nikko) | 12 |
| Polyglyceryl-6 pentaoleate | Nikkol Hexaglyn S-O (Nikko) | <10 |
| Polyglyceryl-3 dioleate | Cremophor G032 (BASF) | <10 |
| Polyglyceryl-3 distearate | Cremophor GS32 (BASF) | <10 |
| Polyglyceryl-4 pentaoleate | Nikkol Tetraglyn 5-O (Nikko) | <10 |
| Polyglyceryl-6 dioleate | Caprol ® 6G20 (ABITEC); Hodag PGO-62 (Calgene), PLUROL OLEIQUE CC 497 (Gattefosse) | 8.5 |
| Polyglyceryl-2 dioleate | Nikkol DGDO (Nikko) | 7 |
| Polyglyceryl-10 trioleate | Nikkol Decaglyn 3-O (Nikko) | 7 |
| Polyglyceryl-10 pentaoleate | Nikkol Decaglyn 5-O (Nikko) | 3.5 |
| Polyglyceryl-10 septaoleate | Nikkol Decagtyn 7-O (Nikko) | 3 |
| Polyglyceryl-10 tetraoleate | Caprol ® 10G40 (ABITEC); Hodag PGO-62 (CALGENE), Drewpol 10-4-O (Stepan) | 6.2 |
| Polyglyceryl-10 decaisostearate | Nikkol Decaglyn 10-IS (Nikko) | <10 |
| Polyglyceryl-10 decaoleate | Drewpol 10-10-O (Stepan), Caprol 10G10O (ABITEC), Nikkol Decaglyn 10-O | 3.5 |
| Polyglyceryl-10 mono, dioleate | Caprol ® PGE 860 (ABITEC) | 11 |
| Polyglyceryl polyricinoleate | Polymuls (Henkel) | 3-20 |

In some embodiments, surfactants utilized in the pharmaceutical compositions described herein include, by way of non-limiting example esters of propylene glycol and fatty acids. Illustrative and non-limiting examples of surfactants of this class are given in Table 7.

TABLE 7

Propylene Glycol Fatty Acid Esters

| COMPOUND | COMMERCIAL PRODUCT (Supplier) | HLB |
|---|---|---|
| Propylene glycol monocaprylate | Capryol 90 (Gattefosse), Nikkol Sefsol 218 (Nikko) | <10 |
| Propylene glycol monolaurate | Lauroglycol 90 (Gattefosse), Lauroglycol FCC (Gattefosse) | <10 |
| Propylene glycol oleate | Lutrol OP2000 (BASF) | <10 |
| Propylene glycol myristate | Mirpyl | <10 |
| Propylene glycol monostearate | ADM PGME-03 (ADM), LIPO PGMS (Lipo Chem.), Aldo ® PGHMS (Lonza) | 3-4 |
| Propylene glycol hydroxy stearate | | <10 |
| Propylene glycol ricinoleate | PROPYMULS (Henkel) | <10 |
| Propylene glycol isostearate | | <10 |
| Propylene glycol monooleate | Myverol P-06 (Eastman) | <10 |
| Propylene dicaprylate/dicaprate | glycol Captex ® 200 (ABITEC), Miglyol ® 840 (Huls), Neobee ® M-20 (Stepan) | >6 |
| Propylene glycol dioctanoate | Captex ® 800 (ABITEC) | |
| Propylene caprylate/caprate | glycol LABRAFAC PG (Gattefosse) | >6 |
| Propylene glycol dilaurate | | >6 |
| Propylene glycol distearate | Kessco ® PGDS (Stepan) | >6 |
| Propylene glycol dicaprylate | Nikkol Sefsol 228 (Nikko) | >6 |
| Propylene glycol dicaprate | Nikkol PDD (Nikko) | >6 |

As discussed above, mixtures of surfactants are also used, in some embodiments, in the pharmaceutical compositions described herein. Mixtures of surfactants include, by way of non-limiting example, mixtures of propylene glycol fatty acid esters and glycerol fatty acid esters are suitable and are commercially available. Illustrative and non-limiting examples of such mixtures of surfactants include, by way of non-limiting example, those shown in Table 8.

TABLE 8

Glycerol/Propylene Glycol Fatty Acid Esters

| COMPOUND | COMMERCIAL PRODUCT (Supplier) | HLB |
|---|---|---|
| Oleic | ATMOS 300, ARLACEL 186 (ICI) | 3-4 |
| Stearic | ATMOS 150 | 3-4 |

In certain embodiments, an important class of surfactants includes the class of mono- and diglycerides. These surfactants are generally lipophilic. Illustrative and non-limiting examples of these surfactants are given in Table 9.

TABLE 9

Mono- and Diglyceride Surfactants

| COMPOUND | COMMERCIAL PRODUCT (Supplier) | HLB |
|---|---|---|
| Monopalmitolein (C16:1) | (Larodan) | <10 |
| Monoelaidin (C18:1) | (Larodan) | <10 |
| Monocaproin (C6) | (Larodan) | <10 |
| Monocaprylin | (Larodan) | <10 |
| Monocaprin | (Larodan) | <10 |
| Monolaurin | (Larodan) | <10 |
| Glyceryl monomyristate (C14) | Nikkol MGM (Nikko) | 3-4 |
| Glyceryl monooleate (C18:1) | PECEOL (Gattefosse), Hodag GMO-D, Nikkol MGO (Nikko) | 3-4 |

TABLE 9-continued

Mono- and Diglyceride Surfactants

| COMPOUND | COMMERCIAL PRODUCT (Supplier) | HLB |
|---|---|---|
| Glyceryl monooleate | RYLO series (Danisco), DIMODAN series (Danisco), EMULDAN (Danisco), ALDO ® MO FG (Lonza), Kessco GMO (Stepan), MONOMULS ® series (Henkel), TEGIN O, DREWMULSE GMO (Stepan), Atlas G-695 (ICI), GMOrphic 80 (Eastman), ADM DMG-40, 70, and 100 (ADM), Myverol (Eastman) | 3-4 |
| Glycerol monooleate/linoleate | OLICINE (Gattefosse) | 3-4 |
| Glycerol monolinoleate | Maisine (Gattefosse), MYVEROL 18-92, Myverol 18-06 (Eastman) | 3-4 |
| Glyceryl ricinoleate | Softigen ® 701 (Huls), HODAG GMR-D (Calgene), ALDO ® MR (Lonza) | 6 |
| Glyceryl monolaurate | ALDO ® MLD (Lonza), Hodag GML (Calgene) | 6.8 |
| Glycerol monopalmitate | Emalex GMS-P (Nihon) | 4 |
| Glycerol monostearate | Capmul ® GMS. (ABITEC), Myvaplex (Eastman), IMWITOR ® 191 (Hüls), CUTINA GMS, Aldo ® MS (Lonza), Nikkol MGS series (Nikko) | 5-9 |
| Glyceryl mono-, dioleate | Capmul ® GMO-K (ABITEC) | <10 |
| Glyceryl palmitic/stearic | CUTINA MD-A, ESTAGEL-G18 | <10 |
| Glyceryl acetate | Lamegin ® EE (Grünau GmbH) | <10 |
| Glyceryl laurate | Inwitor ® 312 (Hüls), Monomuls ® 90-45 (Grünau GmbH), Aldo ® MLD (Lonza) | 4 |
| Glyceryl citrate/lactate/oleate/linoieate | Imwitor ® 375 (Hüls) | <10 |
| Glyceryl caprylate | Imwitor ® 308 (Hüls), Capmul ® MCMC8 (ABITEC) | 5-6 |
| Glyceryl caprylate/caprate | Capmul ® MCM (ABITEC) | 5-6 |
| Caprylic acid mono, diglycerides | Imwitor ® 988 (Hüls) | 5-6 |
| Caprylic/capric glycerides | Imwitor ® 742 (Hüls) | <10 |
| Mono-and diacetylated monoglycerides | Myvacet ® 9-45, Myvacet ® 9-40, Myvacet ® 9-08 (Eastman), Lamegin ® (Grünau) | 3.8-4 |
| Glyceryl monostearate | Aldo ® MS, Arlacel 129 (ICI), LIPO, GMS (Lipo Chem.), Imwitor ® 191 (Hüls), Myvaplex (Eastman) | 4.4 |
| Lactic acid esters of mono, diglycerides | LAMEGIN GLP (Henkel) | <10 |
| Dicaproin (C6) | (Larodan) | <10 |
| Dicaprin (C10) | (Larodan) | <10 |
| Dioctanoin (C8) | (Larodan) | <10 |
| Dimyristin (C14) | (Larodan) | <10 |
| Dipalmitin (C16) | (Larodan) | <10 |
| Distearin | (Larodan) | <10 |
| Glyceryl dilaurate (C12) | Capmul ® GDL (ABITEC) | 3-4 |
| Glyceryl dioleate | Capmul ® GDO (ABITEC) | 3-4 |
| Glycerol esters of fatty acids | GELUCIRE 39/01 (Gattefosse), | 1 |
|  | GELUCIRE 43/01 (Gattefosse) | 6 |
|  | GELUCIRE 37/06 (Gattefosse) |  |
| Dipalmitolein (C16:1) | (Larodan) |  |
| 1,2 and 1,3-diolein (C18:1) | (Larodan) | <10 |
| Dielaidin (C18:1) | (Larodan) | <10 |
| Dilinolein (C18:2) | (Larodan) | <10 |

In some embodiments, surfactants utilized in the pharmaceutical compositions described herein include sterols and derivatives of sterols. In various embodiments, these surfactants are hydrophilic or lipophilic. Illustrative and non-limiting examples of surfactants of this class are shown in Table 10.

TABLE 10

Sterol and Sterol Derivative Surfactants

| COMPOUND | COMMERCIAL PRODUCT (Supplier) | HLB |
|---|---|---|
| Cholesterol, sitosterol, lanosterol |  | <10 |
| PEG-24 cholesterol ether | Solulan C-24 (Amerchol) | >10 |
| PEG-30 cholestanol | Nikkol DHC (Nikko) | >10 |
| Phytosterol | GENEROL series (Henkel) | <10 |
| PEG-25 phyto sterol | Nikkol BPSH-25 (Nikko) | >10 |
| PEG-5 soya sterol | Nikkol BPS-S (Nikko) | <10 |
| PEG-10 soya sterol | Nikkol BPS-10 (Nikko) | <10 |
| PEG-20 soya sterol | Nikkol BPS-20 (Nikko) | <10 |
| PEG-30 soya sterol | Nikkol BPS-30 (Nikko) | >10 |

In some embodiments, surfactants useful in the pharmaceutical compositions described herein include a variety of PEG-sorbitan fatty acid esters. In general, these surfactants are hydrophilic, although several lipophilic surfactants of this class can be used. Illustrative and non-limiting examples of these surfactants are shown in Table 11.

TABLE 11

PEG-Sorbitan Fatty Acid Esters

| COMPOUND | COMMERCIAL PRODUCT (Supplier) | HLB |
|---|---|---|
| PEG-10 sorbitan laurate | Liposorb L-10 (Lipo Chem.) | >10 |
| PEG-20 sorbitan monolaurate | Tween-20 (Atlas/ICI), Crillet 1 (Croda), DACOL MLS 20 (Condea) | 17 |
| PEG-4 sorbitan monolaurate | Tween-21 (Atlas/ICI), Crillet 11 (Croda) | 13 |
| PEG-80 sorbitan monolaurate | Hodag PSML-80 (Calgene); T-Maz 28 | >10 |
| PEG-6 sorbitan monolaurate | Nikkol GL-1 (Nikko) | 16 |
| PEG-20 sorbitan monopalmitate | Tween-40 (Atlas/ICI), Crillet 2 (Croda) | 16 |
| PEG-20 sorbitan monostearate | Tween-60 (Atlas/ICI), Crillet 3 (Croda) | 15 |
| PEG-4 sorbitan monostearate | Tween-61 (Atlas/ICI), Crillet 31 (Croda) | 9.6 |
| PEG-8 sorbitan monostearate | DACOL MSS (Condea) | >10 |
| PBG-6 sorbitan monostearate | Nikkol TS106 (Nikko) | 11 |
| PEG-20 sorbitan tristearate | Tween-65 (Atlas/ICI), Crillet 35 (Croda) | 11 |
| PEG-6 sorbitan tetrastearate | Nikkol GS-6 (Nikko) | 3 |
| PEG-60 sorbitan tetrastearate | Nikkol GS-460 (Nikko) | 13 |
| PEG-5 sorbitan monooleate | Tween-81 (Atlas/ICI), Crillet 41 (Croda) | 10 |

TABLE 11-continued

PEG-Sorbitan Fatty Acid Esters

| COMPOUND | COMMERCIAL PRODUCT (Supplier) | HLB |
|---|---|---|
| PEG-6 sorbitan monooleate | Nikkol TO-106 (Nikko) | 10 |
| PEG-20 sorbitan monooleate | Tween-80 (Atlas/ICI), Crillet 4 (Croda) | 15 |
| PEG-40 sorbitan oleate | Emalex ET 8040 (Nihon Emulsion) | 18 |
| PEG-20 sorbitan trioleate | Tween-85 (Atlas/ICI), Crillet 45 (Croda) | 11 |
| PEG-6 sorbitan tetraoleate | Nikkol GO-4 (Nikko) | 8.5 |
| PEG-30 sorbitan tetraoleate | Nikkol GO-430 (Nikko) | 12 |
| PEG-40 sorbitan tetraoleate | Nikkol GO-440 (Nikko) | 13 |
| PEG-20 monoisostearate | sorbitan Tween-120 (Atlas/ICI), Crillet 6 (Croda) | >10 |
| PEG sorbitol hexaoleate | Atlas G-1086 (ICI) | 10 |
| PEG-6 sorbitol hexastearate | Nikkol GS-6 (Nikko) | 3 |

In some embodiments, surfactants utilized herein include ethers of polyethylene glycol and alkyl alcohols. Illustrative and non-limiting examples of these surfactants are shown in Table 12.

TABLE 12

Polyethylene Glycol Alkyl Ethers

| COMPOUND | COMMERCIAL PRODUCT (Supplier) | HLB |
|---|---|---|
| PEG-2 oleyl ether, oleth-2 | Brij 92/93 (Atlas/ICI) | 4.9 |
| PEG-3 oleyl ether, oleth-3 | Volpo 3 (Croda) | <10 |
| PEG-5 oleyl ether, oleth-5 | Volpo 5 (Croda) | <10 |
| PEG-10 oleyl ether, oleth-10 | Volpo 10 (Croda), Brij 96/97 (Atlas/ICI) | 12 |
| PEG-20 oleyl ether, oleth-20 | Volpo 20 (Croda), Brij 98/99 (Atlas/ICI) | 15 |
| PEG-4 lauryl ether, laureth-4 | Brij 30 (Atlas/ICI) | 9.7 |
| PEG-9 lauryl ether | | >10 |
| PEG-23 lauryl ether, laureth-23 | Brij 35 (Atlas/ICI) | 17 |
| PEG-2 cetyl ether | Brij 52 (ICI) | 5.3 |
| PEG-10 cetyl ether | Brij 56 (ICI) | 13 |
| PEG-20 cetyl ether | Brij 58 (ICI) | 16 |
| PEG-2 stearyl ether | Brij 72 (ICI) | 4.9 |
| PEG-10 stearyl ether | Brij 76 (ICI) | 12 |
| PEG-20 stearyl ether | Brij 78 (ICI) | 15 |
| PEG-100 stearyl ether | Brij 700 (ICI) | >10 |

In certain embodiments, surfactants utilized in the pharmaceutical compositions described herein include esters of sugars. Illustrative and non-limiting examples of such surfactants are shown in Table 13.

TABLE 13

Sugar Ester Surfactants

| COMPOUND | COMMERCIAL PRODUCT (Supplier) | HLB |
|---|---|---|
| Sucrose distearate | SUCRO ESTER 7 (Gattefosse), Crodesta F-10 (Croda) | 3 |
| Sucrose distearate/ monostearate | SUCRO ESTER 11 (Gattefosse), Crodesta F-110 (Croda) | 12 |
| Sucrose dipalmitate | | 7.4 |
| Sucrose monostearate | Crodesta F-160 (Croda) | 15 |
| Sucrose monopalmitate | SUCRO ESTER 15 (Gattefosse) | >10 |
| Sucrose monolaurate | Saccharose monolaurate 1695 (Mitsubishi-Kasei) | 15 |

In some embodiments, surfactants utilized in the pharmaceutical compositions described herein include polyethylene glycol alkyl phenols, e.g., hydrophilic PEG-alkyl phenol surfactants. Illustrative and non-limiting examples of these surfactants are shown in Table 14.

TABLE 14

Polyethylene Glycol Alkyl Phenol Surfactants

| COMPOUND | COMMERCIAL PRODUCT (Supplier) | HLB |
|---|---|---|
| PEG-10-100 nonyl phenol | Triton X series (Rohm & Haas), Igepal CA series (GAF, USA), Antarox CA series (GAF, UK) | >10 |
| PEG-15-100 octyl phenol ether | Triton N-series (Rohm & Haas), Igepal CO series (GAF, USA), Antarox CO series (GAF, UK) | >10 |

In certain embodiments, surfactants utilized in pharmaceutical compositions described herein include polyoxyethylene-polyoxypropylene block copolymers. POE-POP block copolymers are a unique class of polymeric surfactants. The unique structure of the surfactants, with hydrophilic POE and lipophilic POP moieties in well-defined ratios and positions, provides a wide variety of surfactants suitable for use in the present invention. These surfactants are available under various trade names, including Synperonic PE series (ICI); Pluronic® series (BASF), Emkalyx, Lutrol (BASF), Supronic, Monolan, Pluracare, and Plurodac. The generic term for these polymers is "poloxamer" (CAS 9003-11-6). These polymers have the formula: $HO(C_2H_4O)_a(C_3H_6O)_b(C_2H_4O)_aH$; wherein the terms "a" and "b" denote the number of polyoxyethylene and polyoxypropylene units, respectively.

Illustrative and non-limiting examples of suitable surfactants of this class are shown in Table 15. Since the compounds are widely available, commercial sources are not listed in the Table. The compounds are listed by generic name, with the corresponding "a" and "b" values.

TABLE 15

POE-POP Block Copolymers

| COMPOUND | a, b values in $HO(C_2H_4O)_a(C_3H_6O)_b(C_2H_4O)_aH$ | HLB |
|---|---|---|
| Poloxamer 105 | a = 11; b = 16 | 8 |
| Poloxamer 108 | a = 46; b = 16 | >10 |
| Poloxamer 122 | a = 5; b = 21 | 3 |
| Poloxamer 123 | a = 7; b = 21 | 7 |
| Poloxamer 124 | a = 11; b = 21 | >7 |
| Poloxamer 181 | a = 3; b = 30 | |
| Poloxamer 182 | a = 8; b = 30 | 2 |
| Poloxamer 183 | a = 10; b = 30 | |
| Poloxamer 184 | a = 13; b = 30 | |
| Poloxamer 185 | a = 19; b = 30 | |
| Poloxamer 188 | a = 75; b = 30 | 29 |
| Poloxamer 212 | a = 8; b = 35 | |
| Poloxamer 215 | a = 24; b = 35 | |
| Poloxamer 217 | a = 52; b = 35 | |
| Poloxamer 231 | a = 16; b = 39 | |
| Poloxamer 234 | a = 22; b = 39 | |
| Poloxamer 235 | a = 27; b = 39 | |
| Poloxamer 237 | a = 62; b = 39 | 24 |
| Poloxamer 238 | a = 97; b = 39 | |
| Poloxamer 282 | a = 10; b = 47 | |
| Poloxamer 284 | a = 21; b = 47 | |
| Poloxamer 288 | a = 122; b = 47 | >10 |
| Poloxamer 331 | a = 7; b = 54 | 0.5 |
| Poloxamer 333 | a = 20; b = 54 | |
| Poloxamer 334 | a = 31; b = 54 | |
| Poloxamer 335 | a = 38; b = 54 | |
| Poloxamer 338 | a = 128; b = 54 | |
| Poloxamer 401 | a = 6; b = 67 | |

TABLE 15-continued

POE-POP Block Copolymers

| COMPOUND | a, b values in $HO(C_2H_4O)_a(C_3H_6O)_b(C_2H_4O)_aH$ | HLB |
|---|---|---|
| Poloxamer 402 | a = 13; b = 67 | |
| Poloxamer 403 | a = 21; b = 67 | |
| Poloxamer 407 | a = 98; b = 67 | |

In some embodiments surfactants utilized in pharmaceutical compositions described herein include sorbitan esters of fatty acids. Illustrative and non-limiting examples of such surfactants are shown in Table 16.

TABLE 16

Sorbitan Fatty Acid Ester Surfactants

| COMPOUND | COMMERCIAL PRODUCT (Supplier) | HLB |
|---|---|---|
| Sorbitan monolaurate | Span-20 (Atlas/ICI), Crill 1 (Croda), Arlacel 20 (ICI) | 8.6 |
| Sorbitan monopalmitate | Span-40 (Atlas/ICI), Crill 2 (Croda), Nikkol SP-10 (Nikko) | 6.7 |
| Sorbitan monooleate | Span-80 (Atlas/ICI), Crill 4 (Croda), Crill 50 (Croda) | 4.3 |
| Sorbitan monostearate | Span-60 (Atlas/ICI), Crill 3 (Croda), Nikkol SS-10 (Nikko) | 4.7 |
| Sorbitan trioleate | Span-85 (Atlas/ICI), Crill 45 (Croda), Nikkol SO-30 (Nikko) | 4.3 |
| Sorbitan sesquioleate | Arlacel-C (ICI), Crill 43 (Croda), Nikkol SO-15 (Nikko) | 3.7 |
| Sorbitan tristearate | Span-65 (Atlas/ICI) Crill 35 (Croda), Nikkol SS-30 (Nikko) | 2.1 |
| Sorbitan monoisostearate | Crill 6 (Croda), Nikkol SI-10 (Nikko) | 4.7 |
| Sorbitan sesquistearate | Nikkol SS-15 (Nikko) | 4.2 |

In certain embodiments, surfactants utilized in pharmaceutical compositions described herein include esters of lower alcohols ($C_2$ to $C_4$) and fatty acids ($C_8$ to $C_{18}$). Illustrative and non-limiting examples of these surfactants are shown in Table 17.

TABLE 17

Lower Alcohol Fatty Acid Ester Surfactants

| COMPOUND | COMMERCIAL PRODUCT (Supplier) | HLB |
|---|---|---|
| Ethyl oleate | Crodamol EO (Croda), Nikkol EOO (Nikko) | <10 |
| Isopropyl myristate | Crodamol IPM (Croda) | <10 |
| Isopropyl palmitate | Crodamol IPP (Croda) | <10 |
| Ethyl linoleate | Nikkol VF-E (Nikko) | <10 |
| Isopropyl linoleate | Nikkol VF-IP (Nikko) | <10 |

In some embodiments, hydrophilic surfactants utilized in pharmaceutical compositions described herein include ionic surfactants (e.g., cationic, anionic and zwitterionic surfactants). In specific embodiments, anionic surfactants include fatty acid salts and bile acid salts. In certain specific embodiments, cationic surfactants include carnitines. In some specific embodiments, ionic surfactants include, by way of non-limiting example, sodium oleate, sodium lauryl sulfate, sodium lauryl sarcosinate, sodium dioctyl sulfosuccinate, sodium cholate, sodium taurocholate; lauroyl carnitine; palmitoyl carnitine; and myristoyl carnitine. Illustrative and non-limiting examples of such surfactants are shown in Table 18. For simplicity, exemplary counterions are shown in the entries in the Table. In various embodiments, such counterions are optionally substituted with any suitable counterion. For example, although the fatty acids are shown as sodium salts, other cation counterions are optionally used, such as alkali metal cations or ammonium. Unlike certain non-ionic surfactants, these ionic surfactants are generally available as pure compounds, rather than commercial (proprietary) mixtures. Because these compounds are readily available from a variety of commercial suppliers, such as Aldrich, Sigma, and the like, commercial sources are not generally listed in the Table.

TABLE 18

Ionic Surfactants

| COMPOUND | HLB |
|---|---|
| FATTY ACID SALTS | >10 |
| Sodium caproate | |
| Sodium caprylate | |
| Sodium caprate | |
| Sodium laurate | |
| Sodium myristate | |
| Sodium myristolate | |
| Sodium palmitate | |
| Sodium palmitoleate | |
| Sodium oleate | 18 |
| Sodium ricinoleate | |
| Sodium linoleate | |
| Sodium linolenate | |
| Sodium stearate | |
| Sodium lauryl sulfate (dodecyl) | 40 |
| Sodium tetradecyl sulfate | |
| Sodium lauryl sarcosinate | |
| Sodium dioctyl sulfosuccinate [sodium docusate (Cytec)] | |
| BILE SALTS | >10 |
| Sodium cholate | |
| Sodium taurocholate | |
| Sodium glycocholate | |
| Sodium deoxycholate | |
| Sodium taurodeoxycholate | |
| Sodium glycodeoxycholate | |
| Sodium ursodeoxycholate | |
| Sodium chenodeoxycholate | |
| Sodium taurochenodeoxycholate | |
| Sodium glyco cheno deoxycholate | |
| Sodium cholylsarcosinate | |
| Sodium N-methyl taurocholate | |
| Sodium lithocholate | |
| PHOSPHOLIPIDS | |
| Egg/Soy lecithin [Epikuron ™ (Lucas Meyer), Ovothin ™ (Lucas Meyer)] | |
| Lyso egg/soy lecithin | |
| Hydroxylated lecithin | |
| Lysophosphatidylcholine | |
| Cardiolipin | |
| Sphingomyelin | |
| Phosphatidylcholine | |
| Phosphatidyl ethanolamine | |
| Phosphatidic acid | |
| Phosphatidyl glycerol | |
| Phosphatidyl serine | |
| PHOSPHORIC ACID ESTERS | |
| Diethanolammonium polyoxyethylene-10 oleyl ether phosphate | |
| Esterification products of fatty alcohols or fatty alcohol ethoxylates with phosphoric acid or anhydride | |
| CARBOXYLATES | |
| Ether carboxylates (by oxidation of terminal OH group of fatty alcohol ethoxylates) | |
| Succinylated monoglycerides [LAMEGIN ZE (Henkel)] | |
| Sodium stearyl fumarate | |
| Stearoyl propylene glycol hydrogen succinate | |
| Mono/diacetylated tartaric acid esters of mono- and diglycerides | |
| Citric acid esters of mono-, diglycerides | |
| Glyceryl-lacto esters of fatty acids (CFR ref. 172.852) | |

TABLE 18-continued

Ionic Surfactants

| COMPOUND | HLB |
|---|---|
| Acyl lactylates: | |
| lactylic esters of fatty acids | |
| calcium/sodium stearoyl-2-lactylate | |
| calcium/sodium stearoyl lactylate | |
| Alginate salts | |
| Propylene glycol alginate | |
| SULFATES AND SULFONATES | |
| Ethoxylated alkyl sulfates | |
| Alkyl benzene sulfones | |
| α-olefin sulfonates | |
| Acyl isethionates | |
| Acyl taurates | |
| Alkyl glyceryl ether sulfonates | |
| Octyl sulfosuccinate disodium | |
| Disodium undecylenamideo-MEA-sulfosuccinate | |
| CATIONIC Surfactants | >10 |
| Lauroyl carnitine | |
| Palmitoyl carnitine | |
| Myristoyl carnitine | |
| Hexadecyl triammonium bromide | |
| Decyl trimethyl ammonium bromide | |
| Cetyl trimethyl ammonium bromide | |
| Dodecyl ammonium chloride | |
| Alkyl benzyldimethylammonium salts | |
| Diisobutyl phenoxyethoxydimethyl benzylammonium salts | |
| Alkylpyridinium salts | |
| Betaines (trialkylglycine): | |
| Lauryl betaine (N-lauryl,N,N-dimethylglycine) | |
| Ethoxylated amines: | |
| Polyoxyethylene-15 coconut amine | |

In some embodiments, surfactants utilized in pharmaceutical compositions described herein include ionizable surfactants. In certain embodiments, ionizable surfactants, when present in their unionized (neutral, non-salt) form, are lipophilic surfactants suitable for use in the compositions of the present invention. Particular examples of such surfactants include free fatty acids, particularly $C_6$-$C_{22}$ fatty acids, and bile acids. More specifically, suitable unionized ionizable surfactants include the free fatty acid and bile acid forms of any of the fatty acid salts and bile salts shown in Table 18.

In some instances, derivatives of oil-soluble vitamins, such as vitamins A, D, E, K, etc., are also useful surfactants for use in the pharmaceutical compositions described herein. An example of such a derivative is tocopheryl PEG-1000 succinate (TPGS, available from Eastman).

In specific embodiments, surfactants or mixtures of surfactants that solidify (e.g., form a solid, a semi-solid, a gel, a jelly, a paste, or the like) at ambient room temperature are utilized in the pharmaceutical compositions described herein. In certain specific embodiments, surfactants or mixtures of surfactants utilized in the pharmaceutical compositions described herein solidify (e.g., form a solid, a semi-solid, a gel, a jelly, a paste, or the like) at ambient room temperature when combined with additional agents (e.g., particular lipophilic components, such as triglycerides, vitamins (e.g., Vitamin E), or the like, viscosity modifiers, stabilizers, solidifying agents, binders, thickeners, or the like). Such additional agents are optionally utilized in the pharmaceutical compositions described herein. In certain embodiments, pharmaceutical compositions described herein comprise a hydrophilic carrier (e.g., a hydrophilic surfactant), a lipophilic carrier, and/or a viscosity modifier or solidifying agent.

In some specific embodiments, non-ionic hydrophilic surfactants include alkylglucosides; alkylmaltosides; alkylthioglucosides; lauryl macrogolglycerides; polyoxyethylene alkyl ethers; polyoxyethylene alkylphenols; polyethylene glycol fatty acids esters; polyethylene glycol glycerol fatty acid esters; polyoxyethylene sorbitan fatty acid esters; polyoxyethylene-polyoxypropylene block copolymers; polyglycerol fatty acid esters; polyoxyethylene glycerides; polyoxyethylene sterols, derivatives, and analogues thereof; polyoxyethylene vegetable oils; polyoxyethylene hydrogenated vegetable oils; reaction mixtures of polyols with fatty acids, glycerides, vegetable oils, hydrogenated vegetable oils, and sterols; sugar esters, sugar ethers; sucroglycerides; polyethoxylated fat-soluble vitamins or derivatives; and mixtures thereof In certain specific embodiments, the non-ionic hydrophilic surfactant is selected from, by way of non-limiting example, polyoxyethylene alkylethers; polyethylene glycol fatty acids esters; polyethylene glycol glycerol fatty acid esters; polyoxyethylene sorbitan fatty acid esters; polyoxyethylene-polyoxypropylene block copolymers; polyglyceryl fatty acid esters; polyoxyethylene glycerides; polyoxyethylene vegetable oils; and polyoxyethylene hydrogenated vegetable oils. In various embodiments, the glyceride is a monoglyceride, diglyceride, triglyceride, or a mixture thereof.

In some specific embodiments, non-ionic hydrophilic surfactants are the products of reaction mixtures of polyols and fatty acids, glycerides, vegetable oils, hydrogenated vegetable oils or sterols. These reaction mixtures are largely composed of the transesterification products of the reaction, along with often complex mixtures of other reaction products. In more specific embodiments, the polyol is glycerol, ethylene glycol, polyethylene glycol, sorbitol, propylene glycol, pentaerythritol, or a saccharide.

In certain specific embodiments, the hydrophilic surfactant is or includes an ionic surfactant. Specific ionic surfactants include alkyl ammonium salts; bile acids and salts, analogues, and derivatives thereof; fusidic acid and derivatives thereof; fatty acid derivatives of amino acids, oligopeptides, and polypeptides; glyceride derivatives of amino acids, oligopeptides, and polypeptides; acyl lactylates; mono-,diacetylated tartaric acid esters of mono-,diglycerides; succinylated monoglycerides; citric acid esters of mono-,diglycerides; alginate salts; propylene glycol alginate; lecithins and hydrogenated lecithins; lysolecithin and hydrogenated lysolecithins; lysophospholipids and derivatives thereof; phospholipids and derivatives thereof; salts of alkylsulfates; salts of fatty acids; sodium docusate; carnitines; and mixtures thereof.

In some specific embodiments, ionic surfactants include bile acids and salts, analogues, and derivatives thereof; lecithins, lysolecithin, phospholipids, lysophospholipids and derivatives thereof; salts of alkylsulfates; salts of fatty acids; sodium docusate; acyl lactylates; mono-,diacetylated tartaric acid esters of mono-,diglycerides; succinylated monoglycerides; citric acid esters of mono-diglycerides; carnitines; and mixtures thereof. In more specific embodiments, ionic surfactants include, by way of non-limiting example, lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholate, taurocholate, glycocholate, deoxycholate, taurodeoxycholate, chenodeoxycholate, glycodeoxycholate, glycochenodeoxycholate, taurochenodeoxycholate, ursodeoxycholate, tauroursodeoxycholate, glycoursodeoxycholate, cholylsarcosine, N-methyl taurocholate, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof. In more specific embodiments, ionic surfactants are selected from lecithin, lysolecithin, phosphatidylcholine, phosphatidylethanolamine, phosphatidylglycerol, lysophosphatidylcholine, PEG-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholate, taurocholate, glycocholate, deoxycholate, taurodeoxycholate, glycodeoxycholate, cholylsarcosine, caproate, caprylate, caprate, laurate, oleate, lauryl sulfate, docusate, and salts and mixtures thereof, with the most preferred ionic surfactants being lecithin, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, taurocholate, caprylate, caprate, oleate, lauryl sulfate, docusate, and salts and mixtures thereof.

In various embodiments, lipophilic surfactants are selected from, by way of non-limiting example, alcohols; polyoxyethylene alkylethers; fatty acids; glycerol fatty acid esters; acetylated glycerol fatty acid esters; lower alcohol fatty acids esters; polyethylene glycol fatty acids esters; polyethylene glycol glycerol fatty acid esters; polypropylene glycol fatty acid esters; polyoxyethylene glycerides; lactic acid derivatives of mono/diglycerides; propylene glycol diglycerides; sorbitan fatty acid esters; polyoxyethylene sorbitan fatty acid esters; polyoxyethylene-polyoxypropylene block copolymers; transesterified vegetable oils; sterols; sterol derivatives; sugar esters; sugar ethers; sucroglycerides; polyoxyethylene vegetable oils; and polyoxyethylene hydrogenated vegetable oils. As with the hydrophilic surfactants, lipophilic surfactants are optionally the products of reaction mixtures of polyols and fatty acids, glycerides, vegetable oils, hydrogenated vegetable oils, and sterols. In specific embodiments, lipophilic surfactants are selected from fatty acids; lower alcohol fatty acid esters; polyethylene glycol glycerol fatty acid esters; polypropylene glycol fatty acid esters; polyoxyethylene glycerides; glycerol fatty acid esters; acetylated glycerol fatty acid esters; lactic acid derivatives of mono/diglycerides; sorbitan fatty acid esters; polyoxyethylene sorbitan fatty acid esters; polyoxyethylene-polyoxypropylene block copolymers; polyoxyethylene vegetable oils; polyoxyethylene hydrogenated vegetable oils; and reaction mixtures of polyols and fatty acids, glycerides, vegetable oils, hydrogenated vegetable oils, and sterols. In certain specific embodiments, lipophilic surfactants are selected from lower alcohol fatty acids esters; polypropylene glycol fatty acid esters; propylene glycol fatty acid esters; glycerol fatty acid esters; acetylated glycerol fatty acid esters; lactic acid derivatives of mono/diglycerides; sorbitan fatty acid esters; polyoxyethylene vegetable oils; and mixtures thereof, with glycerol fatty acid esters and acetylated glycerol fatty acid esters being most preferred. Among the glycerol fatty acid esters, the esters are, e.g., mono- or diglycerides, or mixtures of mono- and diglycerides, where the fatty acid moiety is a $C_6$ to $C_{22}$ fatty acid. In some specific embodiments, lipophilic surfactants are selected from the products of reaction mixture of polyols and fatty acids, glycerides, vegetable oils, hydrogenated vegetable oils, and sterols. In more specific embodiments, polyols are polyethylene glycol, sorbitol, propylene glycol, and pentaerythritol.

In certain embodiments, pharmaceutical compositions described herein include a lipophilic component or carrier. In some embodiments, the lipophilic carrier is selected from lipophilic surfactants, triglycerides, and Vitamin E compounds (e.g., d,1-α-tocopherol). In specific embodiments, triglycerides utilized in the pharmaceutical compositions described herein are those that solidify (e.g., form a solid, a semi-solid, a gel, a jelly, a paste, or the like) at ambient room temperature, with or without addition of appropriate additives, or those which in combination with particular surfactants and/or active ingredients solidify at room temperature. Illustrative and non-limiting examples examples of triglycerides suitable for use in the pharmaceutical compositions described herein are shown in Table 19. In general, these triglycerides are readily available from commercial sources. For several triglycerides, representative commercial products and/or commercial suppliers are listed.

TABLE 19

| Triglycerides | |
| --- | --- |
| Triglyceride | Commercial Source |
| Aceituno oil | |
| Almond oil | Super Refined Almond Oil (Croda) |
| Araehis oil | |
| Babassu oil | |
| Beeswax | |
| Blackcurrant seed oil | |
| Borage oil | |
| Buffalo ground oil | |
| Candlenut oil | |
| Canola oil | Lipex 108 (Abitec) |
| Castor oil | |
| Chinese vegetable tallow oil | |
| Cocoa butter | |
| Coconut oil | Pureco 76 (Abitec) |
| Coffee seed oil | |
| Corn oil | Super Refined Corn Oil (Croda) |
| Cottonseed oil | Super Refined Cottonseed Oil (Croda) |
| Crambe oil | |
| Cuphea species oil | |
| Evening primrose oil | |
| Grapeseed oil | |
| Groundnut oil | |
| Hemp seed oil | |
| Illipe butter | |
| Kapok seed oil | |
| Linseed oil | |
| Menhaden oil | Super Refined Menhaden Oil (Croda) |
| Mowrah butter | |
| Mustard seed oil | |
| Oiticica oil | |
| Olive oil | Super Refined Olive Oil (Croda) |
| Palm oil | |
| Palm kernel oil | |
| Peanut oil | Super Refined Peanut Oil (Croda) |
| Poppy seed oil | |
| Rapeseed oil | |
| Rice bran oil | |

TABLE 19-continued

Triglycerides

| Triglyceride | Commercial Source |
|---|---|
| Safflower oil | Super Refined Safflower Oil (Croda) |
| Sal fat | |
| Sesame oil | Super Refined Sesame Oil (Croda) |
| Shark liver oil | Super Refined Shark Liver Oil (Croda) |
| Shea nut oil | |
| Soybean oil | Super Refined Soybean Oil (Croda) |
| Stillingia oil | |
| Sunflower oil | |
| Tall oil | |
| Tea seed oil | |
| Tobacco seed oil | |
| Tung oil (China wood oil) | |
| Ucuhuba | |
| Vernonia oil | |
| Wheat germ oil | Super Refined Wheat Germ Oil (Croda) |
| Hydrogenated castor oil | Castorwax |
| Hydrogenated coconut oil | Pureco 100 (Abitec) |
| Hydrogenated cottonseed oil | Dritex C (Abitec) |
| Hydrogenated palm oil | Dritex PST (Abitec); Softisan 154 (Huls) |
| Hydrogenated soybean oil | Sterotex HM NF (Abitec); Dritex S (Abitec) |
| Hydrogenated vegetable oil | Sterotex NF (Abitec); Hydrokote M (Abitec) |
| Hydrogenated cottonseed and castor oil | Sterotex K (Abitec) |
| Partially hydrogenated soybean oil | Hydrokote AP5 (Abitec) |
| Partiaily hydrogenated soy and cottonseed oil | Apex B (Abitec) |
| Glyceryl mono-, di-, tri-behenate | Compritol 888 |
| Glycerol tributyrate | (Sigma) |
| Glyceryl tricaproate | (Sigma) |
| Glyceryl tricaprylate | (Sigma) |
| Glyceryl tricaprate | Captex 1000 (Abitec) |
| Glyceryl triundecanoate | Captex 8227 (Abitec) |
| Glyceryl trilaurate | (Sigma) |
| Glyceryl trimyristate | Dynasan 114 (Hüls) |
| Glyceryl tripalmitate | Dynasan 116 (Hüls) |
| Glyceryl tristearate | Dynasan 118 (Hüls) |
| Glyceryl triarchidate | (Sigma) |
| Glyceryl trimyristoleate | (Sigma) |
| Glyceryl tripalmitoleate | (Sigma) |
| Glyceryl trioleate | (Sigma) |
| Glyceryl trilinoleate | (Sigma) |
| Giyceryl trilinolenate | (Sigma) |
| Glyceryl tricaprylate/caprate | Captex 300 (Abitec); Captex 355 (Abitec); Miglyol 810 (Hüls); Miglyol 812 (Hüls) |
| Glyceryl tricaprylate/caprate/laurate | Captex 350 (Abitec) |
| Glyceryl tricaprylate/caprate/linoleate | Captex 810 (Abitec); Miglyol 818 (Hüls) |
| Glyceryl tricaprylate/caprate/stearate | Softisan 378 (Hüls); (Larodan) |
| Glyceryl tricaprylate/laurate/stearate | (Larodan) |
| Glyceryl 1,2-caprylate-3-linoleate | (Larodan) |
| Glyceryl 1,2-caprate-3-stearate | (Larodan) |
| Glyceryl 1,2-laurate-3-myristate | (Larodan) |
| Glyceryl 1,2-myristate-3-laurate | (Larodan) |
| Glyceryl 1,3-palmitate-2-butyrate | (Larodan) |
| Glyceryl 1,3-stearate-2-caprate | (Larodan) |
| Glyceryl 1,2-linoleate-3-caprylate | (Larodan) |

In certain embodiments, the triglycerides utilized in the pharmaceutical compositions described herein include fractionated triglycerides, modified triglycerides, synthetic triglycerides, and mixtures of triglycerides are also within the scope of the invention. In specific embodiments, triglycerides include, by way of non-limiting example, vegetable oils, fish oils, animal fats, hydrogenated vegetable oils, partially hydrogenated vegetable oils, medium and long-chain triglycerides, and structured triglycerides. It should be appreciated that several commercial surfactant compositions contain small to moderate amounts of triglycerides, typically as a result of incomplete reaction of a triglyceride starting material in, for example, a transesterification reaction. Such commercial surfactant compositions, while nominally referred to as "surfactants", may be suitable to provide all or part of the triglyceride component for the compositions of the present invention. Examples of commercial surfactant compositions containing triglycerides include some members of the surfactant families Gelucires (Gattefosse), Maisines (Gattefosse), and Imwitors (Hüls). Specific examples of these compositions are: Gelucire 44/14 (saturated polyglycolized glycerides); Gelucire 50/13 (saturated polyglycolized glycerides); Gelucire 53/10 (saturated polyglycolized glycerides); Gelucire 33/01 (semi-synthetic triglycerides of $C_8$-$C_{18}$ saturated fatty acids); Gelucire 39/01 (semi-synthetic glycerides); other Gelucires, such as 37/06, 43/01, 35/10, 37/02, 46/07, 48/09, 50/02, 62/05, or the like; Maisine 35-I (linoleic glycerides); and Imwitor 742 (capiylic/capric glycerides).

Additional Agents

The pharmaceutical compositions described herein optionally include one or more additional agents or additives. In certain instances, suitable additives include those that facilitate formulating a pharmaceutical composition described herein as an oral dosage form and include, e.g., coatings and capsule components. Further additives include, by way of non-limiting example, solubilizers, enzyme inhibitors, anti-foaming agents, antioxidants, binders, buffering agents, chleating agents, diluents, disintegrants, flavoring agents, preservatives, sweeteners, thickeners, or the like.

In some embodiments, pharmaceutical compositions provided herein optionally include one or more solubilizers, i.e., additives to increase the solubility of the pharmaceutical active ingredient or other composition components in the solid carrier. Suitable solubilizers for use in the compositions of the present invention include: alcohols, polyols, ethers of polyethylene glycols, amides, esters or the like. Alcohols and polyols include, by way of non-limiting example, ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives. Ethers of polyethylene glycols include those having an average molecular weight of about 200 to about 6000, such as, by way of non-limiting example, tetrahydrofurfuryl alcohol PEG ether (glycofurol, available commercially from BASF under the trade name Tetraglycol) and methoxy PEG (Union Carbide). Amides include, by way of non-limiting example, 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide, and polyvinylpyrrolidone. Esters include, by way of non-limiting example, ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof. Other solubilizers include, by way of non-limiting example, dimethyl acetamide, dimethyl isosorbide (Arlasolve DMI (ICI)), N-methyl pyrrolidones (Pharmasolve (ISP)), monooctanoin, diethylene glycol monoethyl ether (available from Gattefosse under the trade name Transcutol), and water. Mixtures of solubilizers are also within the scope of the present disclosure. Except as indicated, these compounds are readily available from standard commercial sources. In specific embodiments, solubilizers include, by way of non-limiting example, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-600, glycofurol, transcutol, propylene glycol, and dimethyl isosorbide. In certain specific embodiments, solubilizers include sorbitol, glycerol, triacetin, ethyl alcohol, PEG-400, glycofurol and propylene glycol. The amount of solubilizer included in the pharmaceutical compositions described herein is any suitable amount.

Anti-adherents (anti-sticking agents, glidants, flow promoters, lubricants) include, by way of non-limiting example, talc, magnesium stearate, fumed silica (Carbosil, Aerosil), micronized silica (Syloid No. FP 244, Grace U.S.A.), polyethylene glycols, surfactants, waxes, stearic acid, stearic acid salts, stearic acid derivatives, starch, hydrogenated vegetable oils, sodium benzoate, sodium acetate, leucine, PEG-4000 and magnesium lauryl sulfate. Antioxidants include, by way of non-limiting example, BHT, BHA, gallic acid, propyl gallate, ascorbic acid, ascorbyl palmitate, 4-hydroxymethyl-2,6-di-tert-butyl phenol, and tocopherol. Binders (adhesives), i.e., agents that impart cohesive properties to powdered materials through particle-particle bonding, include, by way of non-limiting example, matrix binders (dry starch, dry sugars), film binders (PVP, starch paste, celluloses, bentonite, sucrose), and chemical binders (polymeric cellulose derivatives, such as carboxy methyl cellulose, HPC and HPMC; sugar syrups; corn syrup; water soluble polysaccharides such as acacia, tragacanth, guar and alginates; gelatin; gelatin hydrolysate; agar; sucrose; dextrose; and non-cellulosic binders, such as PVP, PEG, vinyl pyrrolidone copolymers, pregelatinized starch, sorbitol, and glucose). Buffering agents, include an acid and a base, wherein the acid is a pharmaceutically acceptable acid, such as hydrochloric acid, hydrobromic acid, hydriodic acid, sulfuric acid, nitric acid, boric acid, phosphoric acid, acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid, and the base is a pharmaceutically acceptable base, such as an amino acid, an amino acid ester, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide, diisopropylethylamine, ethanolamine, ethylenediamine, triethanolamine, triethylamine, triisopropanolamine, or a salt of a pharmaceutically acceptable cation and acetic acid, acrylic acid, adipic acid, alginic acid, alkanesulfonic acid, an amino acid, ascorbic acid, benzoic acid, boric acid, butyric acid, carbonic acid, citric acid, a fatty acid, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, and uric acid. Chelating agents include, by way of non-limiting example, EDTA and EDTA salts. Colorants or opaquants include, by way of non-limiting example, titanium dioxide, food dyes, lakes, natural vegetable colorants, iron oxides, silicates, sulfates, magnesium hydroxide and aluminum hydroxide. Diluents or fillers include, by way of non-limiting example, lactose, mannitol, talc, magnesium stearate, sodium chloride, potassium chloride, citric acid, spray-dried lactose, hydrolyzed starches, directly compressible starch, microcrystalline cellulose, cellulosics, sorbitol, sucrose, sucrose-based materials, calcium sulfate, dibasic calcium phosphate and dextrose. Disintegrants and super disintegrants include, by way of non-limiting example, croscarmellose sodium, starch, starch derivatives, clays, gums, cellulose, cellulose derivatives, alginates, crosslinked polyvinypyrrolidone, sodium starch glycolate and microcrystalline cellulose. Flavorants or desensitizers include, by way of non-limiting example, spray-dried flavors, essential oils and ethyl vanillin. Plasticizers include, by way of non-limiting example, polyethylene glycol, citrate esters (e.g., triethyl citrate, acetyl triethyl citrate, acetyltributyl citrate), acetylated monoglycerides, glycerin, triacetin, propylene glycol, phthalate esters (e.g., diethyl phthalate, dibutyl phthalate), castor oil, sorbitol and dibutyl seccate. Preservatives include, by way of non-limiting example, ascorbic acid, boric acid, sorbic acid, benzoic acid, and salts thereof, parabens, phenols, benzyl alcohol, and quaternary ammonium compounds. Solvents include, by way of non-limiting example, alcohols, ketones, esters, chlorinated hydrocarbons and water. Sweeteners include, by way of non-limiting example, natural sweeteners such as maltose, sucrose, glucose, sorbitol, glycerin and dextrins, and artificial sweeteners, such as aspartame, saccharine and saccharine salts. Thickeners (viscosity modifiers, thickening agents) include, by way of non-limiting example, sugars, polyvinylpyrrolidone, cellulosics, polymers, high molecular weight polyethylene glycols (e.g., PEG 8000), and alginates. Additives also include, by way of non-limiting example, proteins (e.g., collagen, gelatin, Zein, gluten, mussel protein, lipoprotein); carbohydrates (e.g., alginates, carrageenan, cellulose derivatives, pectin, starch, chitosan); gums (e.g., xanthan gum, gum arabic); spermaceti; natural or synthetic waxes; carnuaba wax; fatty acids (e.g., stearic acid, hydroxystearic acid); fatty alcohols; sugars; shellacs, such as those based on sugars (e.g., lactose, sucrose, dextrose) or starches; polysaccharide-based shellacs (e.g., maltodextrin and maltodextrin derivatives, dextrates, cyclodextrin and cyclodextrin derivatives); cellulosic-based shellacs (e.g., microcrystalline cellulose, sodium carboxymethyl cellulose, hydroxypropylmethyl cellulose, ethyl cellulose, hydroxypropyl cellulose, cellulose acetate, cellulose nitrate, cellulose acetate butyrate, cellulose acetate trimellitate, carboxymethylethyl cellulose, hydroxypropylmethyl cellulose phthalate); inorganics, such as dicalcium phosphate, hydroxyapitite, tricalcium phosphate, talc and titania; polyols, such as mannitol, xylitol and sorbitol; polyethylene glycol esters; and polymers, such as alginates, poly(lactide coglycolide), gelatin, crosslinked gelatin, and agar-agar.

It should be appreciated that there is considerable overlap between the above-listed additives in common usage, since a given additive is often classified differently by different practitioners in the field, or is commonly used for any of several different functions. Thus, the above-listed additives should be taken as merely exemplary, and not limiting, of the types of additives that can be included in compositions of the present invention. The amounts of such additives can be readily determined by one skilled in the art, according to the particular properties desired.

Dosage Forms

In various embodiments, pharmaceutical compositions described herein are formulated as oral dosage forms. Oral dosage forms are prepared by any suitable process including one or more steps of, by way of non-limiting example, agglomeration, air suspension chilling, air suspension drying, balling, coacervation, comminution, compression, pelletization, cryopelletization, encapsulation, extrusion, granulation, homogenization, inclusion complexation, lyophilization, nanoencapsulation, melting, mixing, molding, pan coating, solvent dehydration, sonication, spheronization, spray chilling, spray congealing, spray drying, or the like.

In some embodiments, a pharmaceutical composition described herein is formulated with a substrate to form an oral dosage form. In various embodiments, substrates useful for formulating pharmaceutical compositions described herein as oral dosage forms include or comprise, by way of non-limiting example, a powder or a multiparticulate (e.g., one or more granule, one or more pellet, one or more bead, one or more spherule, one or more beadlet, one or more microcapsule, one or more millisphere, one or more mini capsule, one or more microcapsule, one or more nanocapsule, one or more nanosphere, one or more microsphere, one or more minitablet, one or more tablet, one or more capsule, or one or more combinations thereof). In certain instances, a powder constitutes a finely divided (milled, micronized, nanosized, precipitated) form of an active ingredient or additive molecular aggregates or a compound aggregate of multiple components or a physical mixture of aggregates of an active ingredient and/or additives.

Substrates are prepared from any suitable material including, by way of non-limiting example, sugars, such as lactose, sucrose or dextrose; polysaccharides, such as maltodextrin or dextrates; starches; cellulosics, such as microcrystalline cellulose or microcrystalline cellulose/sodium carboxymethyl cellulose; inorganics, such as dicalcium phosphate, hydroxyapitite, tricalcium phosphate, talc, or titania; and polyols, such as mannitol, xylitol, sorbitol or cyclodextrin. Furthermore, the substrate is optionally composed of active ingredients, surfactants, triglycerides or additives described herein. In one particular embodiment, the substrate is a solid form of an additive, an active ingredient, a surfactant, or a triglyceride; a complex of an additive, surfactant or triglyceride and an active ingredient; a coprecipitate of an additive, surfactant or triglyceride and an active ingredient, or a mixture thereof.

In various embodiments, pharmaceutical compositions and substrates described herein provide or are formulated to provide an oral dosage from selected from, by way of non-limiting example, a minicapsule, a capsule, a tablet, an implant, a troche, a lozenge (minitablet), a temporary or permanent suspension, a wafer, a chewable tablet, a quick or fast dissolving tablet, an effervescent tablet, a buccal or sublingual solid, a granule, a film, a sprinkle, a pellet, a bead, a pill, a powder, a triturate, a strip or a sachet.

In specific embodiments, the oral dosage form described herein is a capsule. Suitable capsule forms include, by way of non-limiting example, hard or soft gelatin capsules, starch capsules, and cellulosic capsules. In more specific embodiments, oral dosage forms described herein are in the form of hard or soft gelatin capsules. In some embodiments, the oral dosage form is a capsule comprising a jelly, solid, semi-solid, glassy or paste-like composition, wherein the testosterone alkyl ester is formulated into the composition.

In specific embodiments, a pharmaceutical composition described herein is formulated as an oral dosage form by (i) heating a pharmaceutical compositions described herein until pharmaceutical composition has an ability to flow (e.g., it is a homogeneous solution, an emulsion, a slurry or the like); and (ii) depositing the pharmaceutical composition with an ability to flow on a substrate. In more specific embodiments, the pharmaceutical composition that has an ability to flow is a homogeneous solution. In further or alternative embodiments, the substrate is one or more capsule, one or more microcapsule, or one or more nanocapsule. In more specific embodiments, the substrate is a hard gelatin capsule or a soft gelatin capsule. In still more specific embodiments, the substrate is a hard gelatin capsule.

EXAMPLES

Example 1

In certain instances, oral dosage forms are prepared in the following manner:

Step 1: transfer the selected amounts of carriers and additives into a clean container and heat the combination until a molten solution is obtained;

Step 2: transfer the selected amount of steroidal compound (e.g., testosterone undecanoate) to the molten solution obtained in Step 1 and homogonize;

Step 3: maintain the mixture of Step 2 at an elevated temperature until used in Step 4; and Step 4: encapsulation of the mixture of Step 3 (e.g., in a hard gelatin capsule).

Using the preceding process, the following capsules are prepared:

TABLE 20

| Capsule 1 | |
| --- | --- |
| Component | % w/w |
| Testosterone undecanoate | 15 |
| Polyoxyl 40 Hydrogenated Castor Oil, NF | 16 |
| Glyceryl Monolinoleate, NF (Maisine 35-1) | 63 |
| Polyethylene Glycol 8000, USP | 6 |
| Total | 100 |

TABLE 21

| Capsule 2 | |
| --- | --- |
| Component | % w/w |
| Testosterone undecanoate | 25 |
| Polyoxyl 35 Castor Oil, NF | 21 |
| Vitamin E, USP (d,l-α-tocopherol) | 48 |
| Polyethylene Glycol 8000, USP | 6 |
| Total | 100 |

TABLE 22

Capsule 3

| Component | % w/w |
|---|---|
| Testosterone undecanoate | 22 |
| Vitamin E Polyethylene Glycol Succinate, NF | 22 |
| Vitamin E, USP (d,l-tocopherol) | 34 |
| Polyethylene Glycol 8000, USP | 4 |
| Hypromellose (100 cP, K100 Premium LV) | 18 |
| Total | 100 |

TABLE 23

Capsule 4

| Component | % w/w |
|---|---|
| Testosterone undecanoate | 22 |
| Vitamin E Polyethylene Glycol Succinate, NF | 22 |
| Vitamin E, USP (d,l-tocopherol) | 34 |
| Polyethylene Glycol 8000, USP | 4 |
| Hypromellose (4,000 cP, K4M) | 18 |
| Total | 100 |

Example 2

Capsules 1-4 are subjected to USP Type-II (paddle) apparatus conditions at 37±0.5° C., at 100 rpm (i.e., deposited in 1 L of DI water having 8% w/v of Triton X-100). FIG. 1 illustrates the release profiles of Capsules 1-4.

Example 3

Clinical Trial Protocol

Study Population: Healthy volunteers (N=24) with a BMI of 18-30 kg/m² and having a pre-trial screening total T concentration of less than 1.3 ng/mL (4.5 mmol/L). Healthy volunteers include post-menopausal women aged 45 or greater.

Study Design: Phase-I, single center, randomized, open-label, study of Capsules 1-4 and 3× an immediate release oral dosage form comprising 40 mg of testosterone undecanoate (so as to provide the same 120 mg dose as Capsules 1-4) formulated in a mixture of castor oil and propylene glycol laurate available under the tradename Andriol®.

Mode of administration: Orally with 240 mL of water about 30 minutes after starting a standardized, high fat, high calorie breakfast preceded by a 10 hour fast. Duration between treatments: minimum of 7 days between the start of each treatment period.

FIG. 2 illustrates the mean plasma testosterone concentrations following administration of Capsules 1-4 and 3× a 40 mg immediate release oral dosage form (for a total of a 120 mg immediate release dose). FIG. 3 illustrates the mean plasma testosterone undecanoate concentrations following administration of Capsules 1-4 and 3× a 40 mg immediate release oral dosage form (for a total of a 120 mg immediate release dose). FIG. 4 illustrates the mean plasma dihydrotestosterone concentrations following administration of Capsules 1-4 and 3× a 40 mg immediate release oral dosage form (for a total of a 120 mg immediate release dose).

Tables 24-26 illustrate the concentration levels of single administration and simulated steady state levels of testosterone, testosterone undecanoate, and dihydrotestosterone obtained.

TABLE 24

Mean Plasma Testosterone Levels

| | Capsule 1 | Capsule 2 | Capsule 3 | Capsule 4 | IR |
|---|---|---|---|---|---|
| Mean $C_{max}$ (ng/mL) single dose | 18.2 | 13.6 | 7.5 | 8.8 | 19.7 |
| Mean $C_{max}$ (ng/mL) steady state | 17.0 | 13.1 | 6.7 | 8.6 | 15.7 |
| Mean $C_{min}$ (ng/mL) steady state | 0.35 | 2.3 | 1.0 | 1.4 | 3.4 |

TABLE 25

Mean Plasma Testosterone Undecanoate Levels

| | Capsule 1 | Capsule 2 | Capsule 3 | Capsule 4 | IR |
|---|---|---|---|---|---|
| Mean $C_{max}$ (ng/mL) single dose | 384.8 | 264.0 | 126.9 | 156.1 | 407.8 |
| Mean $C_{max}$ (ng/mL) steady state | 260.1 | 187.1 | 78.7 | 111.5 | 240.8 |
| Mean $C_{min}$ (ng/mL) steady state | 15.0 | 8.9 | 1.1 | 1.8 | 9.6 |

TABLE 26

Mean Plasma Dihydrotestosterone Levels

| | Capsule 1 | Capsule 2 | Capsule 3 | Capsule 4 | IR |
|---|---|---|---|---|---|
| Mean $C_{max}$ (ng/mL) single dose | 4.4 | 3.6 | 2.3 | 2.4 | 3.9 |
| Mean $C_{max}$ (ng/mL) steady state | 4.6 | 4.0 | 2.3 | 2.3 | 4.1 |
| Mean $C_{min}$ (ng/mL) steady state | 2.2 | 1.6 | 0.9 | 1.0 | 2.2 |

What is claimed is:

1. An oral pharmaceutical composition comprising: (i) testosterone undecanoate at about 15 weight/weight percent (w/w %) of said pharmaceutical composition; (ii) a lipophilic carrier comprising glyceryl monolinoleate said lipophilic carrier present at 50-70 w/w % of the pharmaceutical composition; (iii) 10-20 w/w % of polyoxl 40 hydrogenated castor oil; and (iv) a solidifying agent; wherein said pharmaceutical composition is a jelly, solid, semi-solid or paste-like.

2. The oral pharmaceutical composition of claim 1, providing a plasma testosterone concentration in the range of about 250 ng/dL to about 1200 ng/dL at steady state when orally administered as one or multiple unit dosage forms, twice daily with a meal to a hypogonadal male.

* * * * *